US008426585B2

(12) United States Patent
Xi

(10) Patent No.: US 8,426,585 B2
(45) Date of Patent: Apr. 23, 2013

(54) COMPOUNDS COMPRISING A SPIRO-RING

(75) Inventor: Ning Xi, Newbury Park, CA (US)

(73) Assignees: Ning Xi, Newbury Park, CA (US); Sunshine Lake Pharma Co., Ltd., Northern Industrial Area, Songshan Lake, Dongguan, Guangdong (CN)

(*) Notice: Subject to any disclaimer, the term of this patent is extended or adjusted under 35 U.S.C. 154(b) by 0 days.

(21) Appl. No.: 13/587,936

(22) Filed: Aug. 17, 2012

(65) Prior Publication Data
US 2012/0315247 A1 Dec. 13, 2012

Related U.S. Application Data

(62) Division of application No. 12/576,375, filed on Oct. 9, 2009, now Pat. No. 8,293, 897.

(60) Provisional application No. 61/105,414, filed on Oct. 14, 2008.

(51) Int. Cl.
A61P 35/04 (2006.01)
C07D 403/14 (2006.01)
C07D 413/14 (2006.01)
C07D 471/04 (2006.01)

(52) U.S. Cl.
USPC ............. 544/128; 546/15; 546/113; 546/153

(58) Field of Classification Search ........................ None
See application file for complete search history.

(56) References Cited

U.S. PATENT DOCUMENTS

| 6,143,764 | A | 11/2000 | Kubo et al. |
|---|---|---|---|
| 6,630,489 | B1 | 10/2003 | Crawley |
| 6,797,823 | B1 | 9/2004 | Kubo et al. |
| 6,900,208 | B2 | 5/2005 | Salvati et al. |
| 6,995,171 | B2 | 2/2006 | Autry et al. |
| 7,074,800 | B1 | 7/2006 | Stokes et al. |
| 7,087,622 | B2 | 8/2006 | Li |
| 7,208,500 | B2 | 4/2007 | Lou et al. |
| 7,235,559 | B1 | 6/2007 | Mortlock et al. |
| 7,265,131 | B2 | 9/2007 | Johnson et al. |
| 7,425,564 | B2 | 9/2008 | Fujiwara et al. |
| 7,435,823 | B2 | 10/2008 | Potashman et al. |
| 7,459,562 | B2 | 12/2008 | Borzilleri et al. |
| 7,495,104 | B2 | 2/2009 | Miwa et al. |
| 7,560,558 | B2 | 7/2009 | Shimizu et al. |
| 7,566,784 | B2 | 7/2009 | Borzilleri et al. |
| 7,576,074 | B2 | 8/2009 | Rice et al. |
| 7,579,473 | B2 | 8/2009 | Bannen et al. |
| 2004/0053908 | A1 | 3/2004 | Funahashi et al. |
| 2004/0242603 | A1 | 12/2004 | Fujiwarn et al. |
| 2005/0245547 | A1 | 11/2005 | Kim et al. |
| 2006/0052396 | A1 | 3/2006 | Berg et al. |
| 2006/0074056 | A1 | 4/2006 | Vaisburg et al. |
| 2006/0183911 | A1 | 8/2006 | Charrier et al. |
| 2006/0241104 | A1 | 10/2006 | Borziller et al. |
| 2006/0252777 | A1 | 11/2006 | Kim et al. |
| 2007/0004675 | A1 | 1/2007 | Saavedra et al. |
| 2007/0117802 | A1 | 5/2007 | Borzilleri et al. |
| 2007/0129389 | A1 | 6/2007 | Bibe |
| 2007/0161651 | A1 | 7/2007 | Ibrahim et al. |
| 2007/0179130 | A1 | 8/2007 | Bannen |
| 2007/0244116 | A1 | 10/2007 | Bannen et al. |
| 2008/0161305 | A1 | 7/2008 | Forsyth et al. |
| 2008/0227811 | A1 | 9/2008 | Chen |
| 2008/0312232 | A1 | 12/2008 | Kim et al. |
| 2009/0034420 | A1 | 2/2009 | Boeckle et al. |
| 2009/0069316 | A1 | 3/2009 | Hong et al. |
| 2009/0264440 | A1 | 10/2009 | Claridge et al. |
| 2009/0306103 | A1 | 12/2009 | Boyer et al. |

FOREIGN PATENT DOCUMENTS

| EP | 1889836 | 2/2008 |
|---|---|---|
| JP | 2010178651 | 8/2010 |
| WO | WO2004092196 | 10/2004 |
| WO | WO2005030140 | 4/2005 |
| WO | WO 2005030140 A2 * | 4/2005 |
| WO | WO2005121125 | 12/2005 |
| WO | WO2006116713 | 11/2006 |
| WO | WO2007059257 | 5/2007 |
| WO | WO2007084875 | 7/2007 |
| WO | WO2008049855 | 5/2008 |
| WO | WO2008102870 | 8/2008 |
| WO | WO2009033084 | 3/2009 |
| WO | WO2009042646 | 4/2009 |
| WO | WO2009049028 | 4/2009 |
| WO | WO2009087381 | 7/2009 |
| WO | WO2009093049 | 7/2009 |
| WO | WO2009094417 | 7/2009 |
| WO | WO2009096435 | 8/2009 |
| WO | WO2009125597 | 10/2009 |
| WO | WO2010011538 | 1/2010 |
| WO | WO2010036831 | 4/2010 |
| WO | WO2010044543 | 4/2010 |
| WO | WO2010051373 | 5/2010 |
| WO | WO2010056960 | 5/2010 |
| WO | WO2010111063 | 9/2010 |
| WO | WO2010144909 | 12/2010 |
| WO | WO2010151710 | 12/2010 |
| WO | WO2011017142 | 2/2011 |
| WO | WO2011017639 | 2/2011 |
| WO | WO2011023081 | 3/2011 |
| WO | WO2011029001 | 3/2011 |

OTHER PUBLICATIONS

EP search report, Oct. 2, 2012, EPO.
EP Search Report, Jun. 15, 2012, EPO.
Liu et al., J Med. Chem., Jun. 14, 2008, vol. 51, No. 13, p. 3688-3691.

* cited by examiner

Primary Examiner — Janet L. Andres
Assistant Examiner — Timothy R Rozof
(74) Attorney, Agent, or Firm — Squire Sanders; Kam W. Law

(57) ABSTRACT

The present invention provides novel compounds useful in modulating the protein tyrosine kinase activity, and in modulating inter- and/or intra-cellular signaling. The invention also provides pharmaceutically acceptable compositions comprising such compounds and methods of using the compositions in the treatment of hyperproliferative disorders in mammals, especially humans.

21 Claims, No Drawings

COMPOUNDS COMPRISING A SPIRO-RING

CROSS-REFERENCE TO RELATED APPLICATIONS

This application is a divisional application of U.S. non-provisional application Ser. No. 12/573,375 which claims the benefit of U.S. provisional application No. 61/105,414, filed Oct. 14, 2008, all of which are hereby incorporated by reference in their entirety.

FIELD OF THE INVENTION

Provided herein are novel compounds that are useful in the treatment of hyperproliferative diseases, such as cancers, in mammals. In particular, the invention relates to compounds that inhibit the protein tyrosine kinase activity, resulting in the inhibition of inter- and/or intra-cellular signaling. Provided also herein are methods of using such compounds in the treatment of hyperproliferative diseases in mammals, especially humans, and pharmaceutical compositions containing such compounds.

BACKGROUND OF THE INVENTION

Protein kinases represent a large family of proteins, which play a pivotal role in the regulation of a wide variety of cellular processes, maintaining control over cellular function. Protein tyrosine kinases may be classified as growth factor receptor (e.g. VEGFR, EGFR, PDGFR, FGFR and erbB2) or non-receptor (e.g. c-src and bcr-abl) kinases. The receptor type tyrosine kinases make up about 20 different subfamilies. The non-receptor type tyrosine kinases make up numerous subfamilies. Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Aberrant or inappropriate protein kinase activity can contribute to the rise of disease states associated with such aberrant kinase activity.

A partial list of such kinases include abl, AATK, ALK, Akt, axl, bmx, bcr-abl, Blk, Brk, Btk, csk, c-kit, c-Met, c-src, c-fins, CDK1, CDK2, CDK3, CDK4, CDK5, CDK6, CDK7, CDK8, CDK9, CDK10, CRaf1, CSF1R, CSK, DDR1, DDR2, EPHA, EPHB, EGFR, ErbB2, ErbB3, ErbB4, Erk, Fak, fes, FER, FGFR1, FGFR2, FGFR3, FGFR4, FGFR5, Fgr, flt-1, Fps, Frk, Fyn, GSG2, GSK, Hck, ILK, INSRR, IRAK4, ITK, IGF-1R, INS-R, Jak, KSR1, KDR, LMTK2, LMTK3, LTK, Lck, Lyn, MATK, MERTK, MLTK, MST1R, MUSK, NPR1, NTRK, MEK, PLK4, PTK, p38, PDGFR, PIK, PKC, PYK2, RET, ROR1, ROR2, RYK, ros, Ron, SGK493, SRC, SRMS, STYK1, SYK, TEC, TEK, TEX14, TNK1, TNK2, TNNI3K, TXK, TYK2, TYRO3, tie, tie2, TRK, Yes, and Zap70. Inhibition of such kinases has become an important therapeutic target. Certain diseases are known to be associated with deregulated angiogenesis, for example, ocular neovascularisation, such as retinopathies (including diabetic retinopathy); age-related macular degeneration; psoriasis; hemangioblastoma; hemangioma; arteriosclerosis; inflammatory diseases, such as a rheumatoid or rheumatic inflammatory disease, especially arthritis (including rheumatoid arthritis); or other chronic inflammatory disorders, such as chronic asthma; arterial or post-transplantational atherosclerosis; endometriosis; and neoplastic diseases, for example so-called solid tumors and liquid tumors (such as leukemias).

Angiogenesis is an important component of certain normal physiological processes such as embryogenesis and wound healing, but aberrant angiogenesis contributes to some pathological disorders and in particular to tumor growth. VEGF-A (vascular endothelial growth factor A) is a key factor promoting neovascularization (angiogenesis) of tumors. VEGF induces endothelial cell proliferation and migration by signaling through two high affinity receptors, the fms-like tyrosine kinase receptor, flt-1, and the kinase insert domain-containing receptor, KDR. These signaling responses are critically dependent upon receptor dimerization and activation of intrinsic receptor tyrosine kinase (RTK) activity. The binding of VEGF as a disulfide-linked homodimer stimulates receptor dimerization and activation of the RTK domain. The kinase activity autophosphorylates cytoplasmic receptor tyrosine residues, which then serve as binding sites for molecules involved in the propagation of a signaling cascade.

Disruption of VEGF receptor signaling is a highly attractive therapeutic target in cancer, as angiogenesis is a prerequisite for all solid tumor growth, and that the mature endothelium remains relatively quiescent (with the exception of the female reproductive system and wound healing). A number of experiment approaches to inhibiting VEGF signaling have been examined, including use of neutralizing antibodies receptor antagonists, small molecule antagonists, antisense constructs and dominant-negative strategies ("Molecular basis for sunitinib efficacy and future clinical development." *Nature Review Drug Discovery*, 2007, 6, 734; Angiogenesis: "an organizing principle for drug discovery?" *Nature Review Drug Discovery*, 2007, 6, 273).

Hepatocyte growth factor (HGF), also known as scatter factor, is a multifunctional growth factor that enhances transformation and tumor development by inducing mitogenesis and cell motility. In order to produce cellular effects, HGF must bind to its receptor, c-Met, a receptor tyrosine kinase. c-Met is overexpressed in a significant percentage of various types of human cancers and is often amplified during the transition between primary tumors and metastasis. c-Met is also implicated in atherosclerosis and lung fibrosis ("Molecular cancer therapy: can our expectation be MET." *Euro. J. Cancer*, 2008, 44, 641-651). Invasive growth of certain cancer cells is drastically enhanced by tumor-stromal interactions involving the HGF/c-Met (HGF receptor) pathway. Binding of HGF to c-Met leads to receptor phosphorylation and activation of Ras/mitogen-activated protein kinase (MAPK) signaling pathway, thereby enhancing malignant behaviors of cancer cells. Moreover, stimulation of the HGF/c-Met pathway itself can lead to the induction of VEGF expression, itself contributing directly to angiogenic activity ("From Tpr-Met to Met, tumorigenesis and tubes." *Oncogene.* 2007, 26, 1276; "Targeting the c-Met Signaling Pathway in Cancer." *Clin. Cancer Res.* 2006, 12, 3657; "Drug development of MET inhibitors: targeting oncogene addiction and expedience." *Nature Review Drug Discovery*, 2008, 7, 504).

Insulin-like growth factor 1 receptor (IGF1R) is an integral membrane tyrosine kinase receptor that binds insulin-like growth factor (IGF) with high affinity. IGF1R plays a critical role in transformation events and human cancer. It is highly over-expressed in most malignant tissues where it functions as an anti-apototic agent by enhancing cell survival through the PI3K pathway, and also the p53 pathway. IGF1R has been linked to various disease states, such as breast and ovarian cancer, metastatic uveal melanoma, macular degeneration, and intrauterine growth retardation and poor postnatal growth, among others ("IGF1R signaling and its inhibition."

Endocrine-Related Cancer, 2006, 13, S33-S43; "The new kid on the block(ade) of the IGF-1 receptor." Cancer Cell, 2004, 5, 201.).

Anti-tumor approaches that target VEGF/VEGFR, HGF/c-Met and/or IGF/IGF1R signaling may circumvent the ability of tumor cells to overcome VEGFR, HGFR or IGF1R inhibition alone and may represent improved cancer therapeutics. Here we describe small molecules that are potent inhibitors of protein tyrosine kinase activity, such as that of, for example, the VEGF receptor KDR, the HGF receptor c-Met, and/or the IGF receptor IGF1R, among others.

SUMMARY OF THE INVENTION

Provided herein are new compounds and methods for treating cell proliferative diseases. The compounds disclosed herein may be inhibitors of protein tyrosine kinase activity. In some embodiments, the compounds disclosed herein are multiple function inhibitors, capable of inhibiting, for example, VEGF, HGF and/or IGF receptor signaling. Accordingly, provided herein are new inhibitors of protein tyrosine kinase receptor signaling, such as for example, VEGF receptor signaling, HGF receptor signaling, and/or IGF receptor signaling, including the VEGF receptor KDR, the HGF receptor c-Met, and/or IGF1R.

Specifically, it has been found that compounds disclosed herein, and pharmaceutically acceptable compositions thereof, are effective as inhibitors of receptor tyrosine kinases, especially c-Met, KDR and/or IGF1R. In one aspect, provided herein are compounds having Formula (I) as shown below:

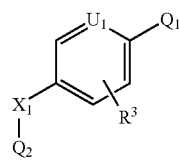

(I)

or a stereoisomer, a geometric isomer, a tautomer, an N-oxide, a hydrate, a solvate, a metabolite, a pharmaceutically acceptable salt or a prodrug thereof, wherein each of $R^3$, $U_1$, $X_1$, $Q_1$ and $Q_2$ is as defined herein.

In another aspect, provided herein are compounds having Formula (IV) as shown below:

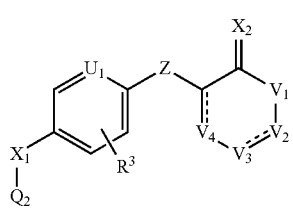

(IV)

or a stereoisomer, a geometric isomer, a tautomer, an N-oxide, a hydrate, a solvate, a metabolite, a pharmaceutically acceptable salt or a prodrug thereof, wherein each of $R^3$, $U_1$, $V_1$, $V_2$, $V_3$, $V_4$, $X_1$, $X_2$, Z, and $Q_2$ is as defined herein.

In another aspect, provided herein are compounds having Formula (V) as shown below:

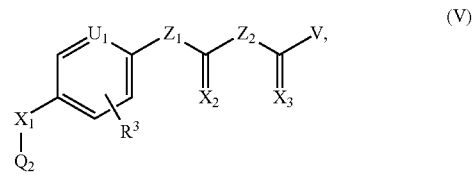

(V)

or a stereoisomer, a geometric isomer, a tautomer, an N-oxide, a hydrate, a solvate, a metabolite, a pharmaceutically acceptable salt or a prodrug thereof, wherein each of $R^3$, $U_1$, V, $X_1$, $X_2$, $X_3$, $Z_1$, $Z_2$ and $Q_2$ is as defined herein.

In certain embodiments, $Q_1$ of formula (I) has Formula (IIa) or (IIb):

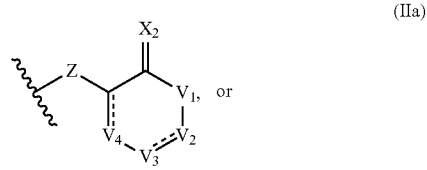

(IIa)

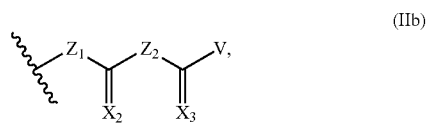

(IIb)

wherein each of V, $V_1$, $V_2$, $V_3$, $V_4$, $X_2$, $X_3$, Z, $Z_1$ and $Z_2$ is as defined herein.

In other embodiments, formula (IIa) is

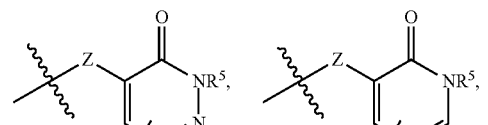

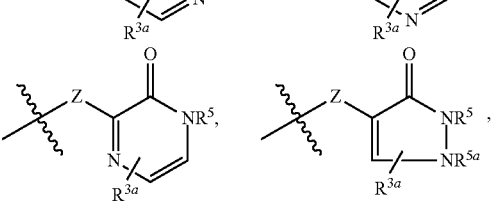

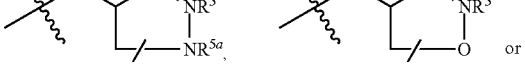

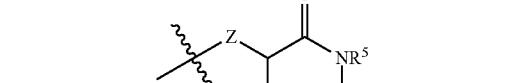

wherein each of $R^{3a}$, $R^5$, $R^{5a}$, Z is as defined herein.

In other embodiments, formula (IIb) is
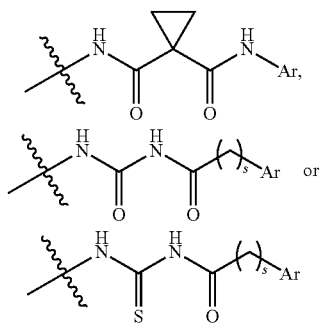
wherein Ar is substituted or unsubstituted aryl or heteroaryl; and s is 0 or 1.
In some embodiments, $Q_2$ of formula (I), (IV) or (V) has Formula (III):
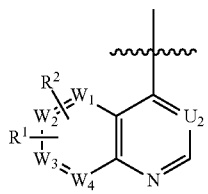
(III)
wherein each of $R^1$, $R^2$, $W_1$, $W_2$, $W_3$, $W_4$ and $U_2$ is as defined herein.
In certain embodiments, $Q_2$ of formula (I), (IV) or (V) is
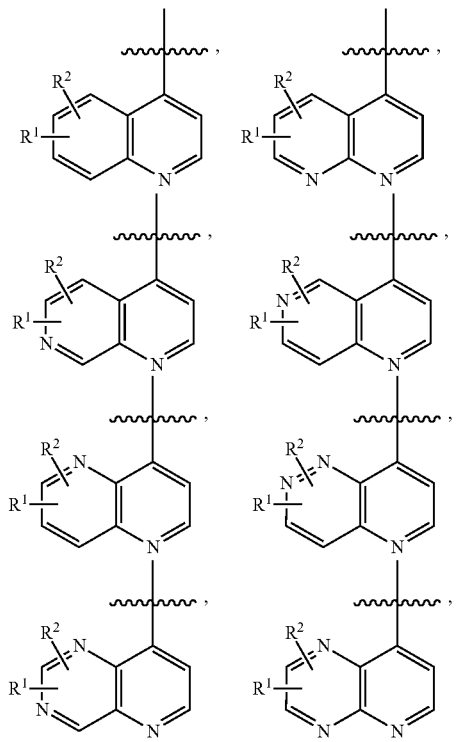
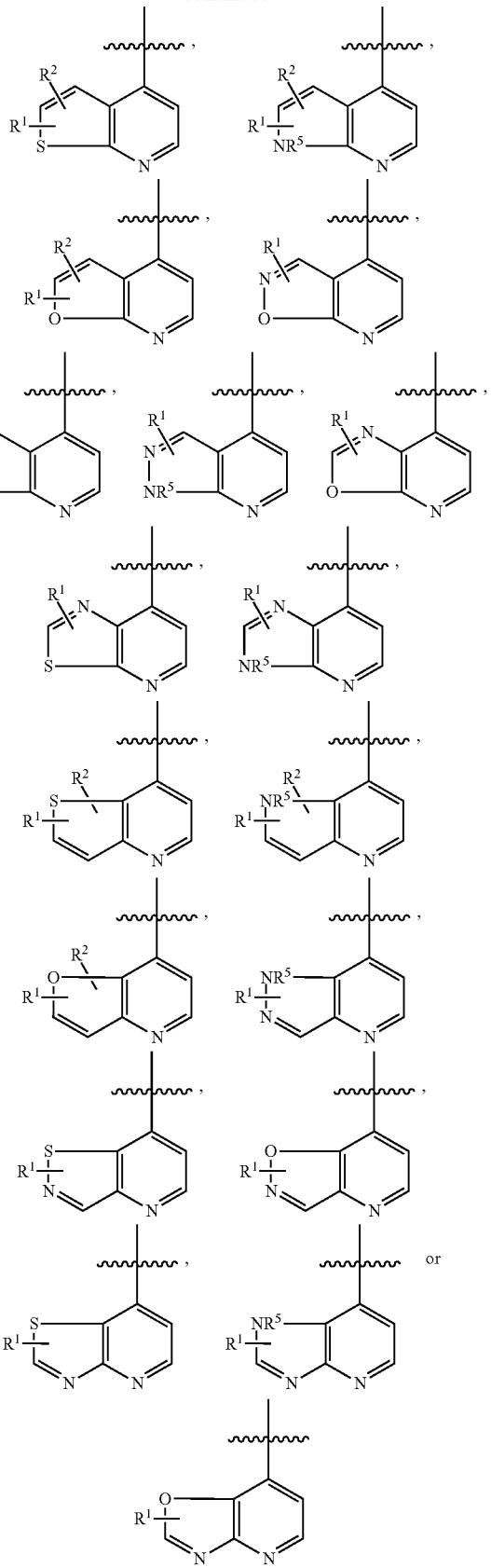
wherein each of $R^1$, $R^2$ and $R^5$ is as defined herein.

In some embodiments, each $R^1$ disclosed herein is independently $R^{5a}R^5N-$, $-OC(=O)NR^5R^{5a}$, $-OC(=O)OR^5$, $-NR^5C(=O)NR^5R^{5a}$, $-NR^5C(=O)-R^{5a}$, $R^5R^{5a}N-O_2S-$, $R^5O_2S-$, $R^5O_2SR^{5a}N-$, $R^5S(=O)$-alkyl, $R^5R^{5a}N-C(=O)-C_{1-6}$ alkyl, $R^5S(=O)$-alkoxy, $R^5R^{5a}N-C(=O)$-alkoxy, hydroxy-substituted aminoalkoxy, amino-substituted haloalkoxy, hydroxy-substituted haloalkoxy, heterocyclyl(aminoalkoxy), heteroaryl(hydroxyalkoxy), hydroxy-substituted cyclopropylalkoxy, $R^5S(=O)_2O$-substituted cyclopropylalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicycloxoalkoxy, fused heterobicycloxoalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)NR^5—, fused heterobicyclyl-C(=O)NR^5—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicycloxoalkoxy, spiro heterobicycloxoalkoxy, spiro bicyclylaminoalkoxy, spiro heterobicyclylaminoalkoxy, spiro bicyclyl—C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)NR^5—, or spiro heterobicyclyl-C(=O)NR^5—.

In other embodiments, each $R^1$ disclosed herein is independently $R^{5a}R^5N-$, $-OC(=O)NR^5R^{5a}$, $-OC(=O)OR^5$, $-NR^5C(=O)NR^5R^{5a}$, $-NR^5C(=O)-R^{5a}$, $R^5R^{5a}N-O_2S-$, $R^5O_2S-$, $R^5O_2SR^{5a}N-$, $R^5S(=O)$-alkyl, $R^5R^{5a}N-C(=O)-C_{1-6}$ alkyl, $R^5S(=O)$-alkoxy, $R^5R^{5a}N-C(=O)$-alkoxy, hydroxy-substituted $C_{1-6}$ aminoalkoxy, amino-substituted $C_{1-6}$ haloalkoxy, hydroxy-substituted $C_{1-6}$ haloalkoxy, $C_{4-10}$ heterocyclylamino $C_{1-6}$ alkoxy, $C_{1-10}$ heteroaryl(hydroxyalkoxy), hydroxy-substituted cyclopropyl $C_{1-6}$ alkoxy, $R^5S(=O)_2O$-substituted cyclopropyl $C_{1-6}$ alkoxy, $C_{5-12}$ fused bicyclyl, $C_{5-12}$ fused heterobicyclyl, $C_{5-12}$ fused bicyclyl aliphatic, $C_{5-12}$ fused heterobicyclyl aliphatic, $C_{5-12}$ fused bicycloxy, $C_{5-12}$ fused heterobicycloxy, $C_{5-12}$ fused bicyclylamino, $C_{5-12}$ fused heterobicyclylamino, $C_{5-12}$ fused bicycloxoalkoxy, $C_{5-12}$ fused heterobicycloxoC_{1-6}alkoxy, $C_{5-12}$ fused bicyclyl-C(=O)—, $C_{5-12}$ fused bicyclyl-C(=O)O—, $C_{5-12}$ fused heterobicyclyl-C(=O)—, $C_{5-12}$ fused heterobicyclyl-C(=O)O—, $C_{5-12}$ fused bicyclylamino-C(=O)—, $C_{5-12}$ fused heterobicyclylamino-C(=O)—, $C_{5-12}$ fused bicyclyl-C(=O)NR^5—, $C_{5-12}$ fused heterobicyclyl-C(=O)NR^5—, $C_{5-12}$ spiro bicyclyl, $C_{5-12}$ spiro heterobicyclyl, $C_{5-12}$ spiro bicyclyl $C_{1-6}$ aliphatic, $C_{5-12}$ spiro heterobicyclyl $C_{1-6}$ aliphatic, $C_{5-12}$ spiro heterobicycloxo $C_{1-6}$ alkoxy, $C_{5-12}$ spiro heterobicyclylamino $C_{1-6}$ alkoxy, $C_{5-12}$ spiro bicyclyl—C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)NR^5—, or $C_{5-12}$ spiro heterobicyclyl-C(=O)NR^5—.

In further embodiments, each $R^1$ disclosed herein is independently has one of the following structures:

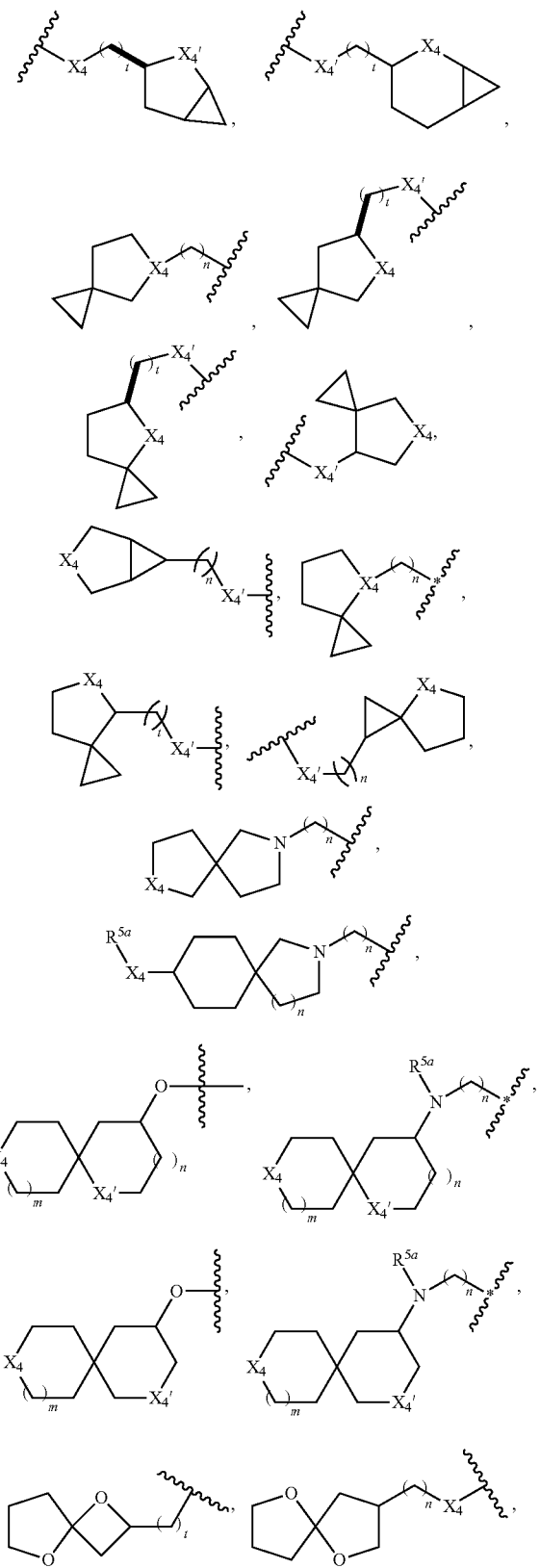

wherein each of $X_4$ and $X_4'$ is independently $(CR^4R^{4a})_m$, $NR^5$, O, S, S=O or $SO_2$; each of m and n is independently 0, 1 or 2; and t is 1, 2 or 3.

In certain embodiments, each $R^2$ disclosed herein is independently H, halo, cyano, hydroxyl, $R^{5a}R^5N$—, —C(=O)$NR^5R^{5a}$, —OC(=O)$NR^5R^{5a}$, —OC(=O)$OR^5$, —$NR^5C$(=O)$NR^5R^{5a}$, —$NR^5C$(=O)$OR^{5a}$, —$NR^5C$(=O)—$R^{5a}$, $R^5R^{5a}N$—$O_2S$—, $R^5O_2S$—, $R^5O_2SR^{5a}N$—, $R^{5a}R^5N$-alkyl, $R^5S$(=O)-alkyl, $R^5R^{5a}N$—C(=O)-alkyl, $R^{5a}R^5N$-alkoxy, $R^5S$(=O)-alkoxy, $R^5R^{5a}N$—C(=O)-alkoxy, aliphatic, alkoxy, hydroxyalkoxy, aminoalkoxy, hydroxy-substituted aminoalkoxy, haloalkoxy, amino-substituted haloalkoxy, alkylamino haloalkoxy, hydroxy-substituted haloalkoxy, alkylaminoalkoxy, alkoxyalkoxy, arylalkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, aryloxy, heterocyclyloxyalkoxy, carbocyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicycloxoalkoxy, fused heterobicycloxoalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)$NR^5$—, fused heterobicyclyl-C(=O)$NR^5$—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicycloxoalkoxy, spiro heterobicycloxoalkoxy, spiro bicyclylaminoalkoxy, spiro heterobicyclylaminoalkoxy, spiro bicyclyl —C(=O)—, spiro bicyclyl-C(=O)O—, spiro heterobicyclyl-C(=O)—, spiro heterobicyclyl-C(=O)O—, spiro bicyclylamino-C(=O)—, Spiro heterobicyclylamino-C(=O)—, spiro bicyclyl-C(=O)$NR^5$—, or spiro heterobicyclyl-C(=O)$NR^5$—, aryl, heteroaryl, arylaliphatic or heteroarylaliphatic, with the proviso that when alkoxy or alkylamino is substituted, each of alkoxy or alkylamino is independently substituted with one or more hydroxy groups, amino groups or substituted amino groups.

In other embodiments, each $R^2$ disclosed herein is independently H, halo, cyano(CN), $R^{5a}R^5N$—$C_{1-6}$ alkoxy, optionally substituted $C_{1-6}$ alkoxy, $C_{1-6}$ hydroxyalkoxy, $C_{1-6}$ aminoalkoxy, $C_{1-6}$ hydroxy-substituted aminoalkoxy, $C_{1-6}$ haloalkoxy, $C_{1-6}$ alkylamino $C_{1-6}$ alkoxy, $C_{1-6}$ alkoxy $C_{1-6}$ alkoxy, $C_{4-10}$ heterocyclyloxy $C_{1-6}$ alkoxy, $C_{5-12}$ fused bicyclyl, $C_{5-12}$ fused bicyclyl $C_{1-6}$ aliphatic, $C_{5-12}$ fused heterobicyclyl $C_{1-6}$ aliphatic, $C_{5-12}$ fused bicycloxy, $C_{5-12}$ fused bicyclylamino, $C_{5-12}$ fused bicycloxo $C_{1-6}$ alkoxy, $C_{5-12}$ fused bicyclylamino $C_{1-6}$ alkoxy, $C_{5-12}$ fused bicyclyl-C(=O)—, $C_{5-12}$ fused bicyclyl-C(=O)O—, $C_{5-12}$ fused heterobicyclyl-C(=O)—, $C_{5-12}$ fused heterobicyclyl-C(=O)O—, $C_{5-12}$ fused bicyclylamino-C(=O)—, $C_{5-12}$ fused heterobicyclylamino-C(=O)—, $C_{5-12}$ fused bicyclyl-C(=O)$NR^5$—, $C_{5-12}$ fused heterobicyclyl-C(=O)$NR^5$—, $C_{5-12}$ Spiro bicyclyl, $C_{5-12}$ Spiro bicycloxy, $C_{5-12}$ spiro bicyclylamino, $C_{5-12}$ spiro bicycloxo $C_{1-6}$ alkoxy, $C_{5-12}$ spiro bicyclylamino $C_{1-6}$ alkoxy, $C_{5-12}$ fused heterobicyclyl, $C_{5-12}$ fused heterobicycloxy, $C_{5-12}$ fused heterobicyclylamino, $C_{5-12}$ fused heterobicycloxo $C_{1-6}$ alkoxy, $C_{5-12}$ fused heterobicyclylamino $C_{1-6}$ alkoxy, $C_{5-12}$ spiro bicyclyl, $C_{5-12}$ spiro heterobicyclyl, $C_{5-12}$ spiro bicyclyl $C_{1-6}$ aliphatic, $C_{5-12}$ spiro heterobicyclyl $C_{1-6}$ aliphatic, $C_{5-12}$ spiro heterobicycloxo $C_{1-6}$ alkoxy, $C_{5-12}$ spiro heterobicyclylamino $C_{1-6}$ alkoxy, $C_{5-12}$ spiro bicyclyl —C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)NR$^5$—, or $C_{5-12}$ spiro heterobicyclyl-C(=O)NR$^5$—, $C_{6-10}$ aryl, $C_{1-10}$ heteroaryl, $C_{6-10}$ aryl $C_{1-6}$ aliphatic or $C_{1-10}$ heteroaryl $C_{1-6}$ aliphatic.

In some embodiments, each of R$^3$ and R$^{3a}$ disclosed herein is independently H, F, Cl, Br, I, —CN, hydroxyl, R$^{5a}$R$^5$N—, R$^{5a}$R$^5$N-aliphatic, hydroxyaliphatic, aliphatic, alkoxy, alkoxyaliphatic, haloalkyl, heterocyclyl, heterocyclylalkyl, cycloalkyl, cycloalkoxy aliphatic, heterocycloxy aliphatic, cycloalkylalkoxy, heterocyclylalkoxy, aryloxyalkyl, heteroaryloxy aliphatic, arylaliphatic, heteroaryl aliphatic, aryl, or heteroaryl. In other embodiments, each of R$^3$ and R$^{3a}$ disclosed herein is independently H, F, Cl, Br, —CN, R$^{5a}$R$^5$N—C$_{1-3}$aliphatic, C$_{1-3}$ aliphatic, C$_{1-3}$ alkoxy C$_{1-3}$ alkyl, C$_{1-3}$ alkoxy, C$_{1-3}$ haloalkyl, cycloalkoxy C$_{1-3}$aliphatic, or heterocycloxy C$_{1-3}$ aliphatic.

In certain embodiments, each of U$_1$ and U$_2$ disclosed herein is independently CR$^4$ or N.

In some embodiments, each V disclosed herein is independently NR$^5$R$^{5a}$, OR$^5$, aliphatic, cycloalkyl, heterocyclyl, aryl, heteroaryl, arylaliphatic, or heteroarylaliphatic. In other embodiments, each V$_1$ disclosed herein is O or NR$^5$. In further embodiments, each of V$_2$, V$_3$ and V$_4$ disclosed herein is independently CR$^4$R$^{4a}$, NR$^5$, CR$^4$ or N, with the proviso that only one of V$_2$, V$_3$, and V$_4$ is NR$^5$ or N, or V$_2$ and V$_3$ or V$_3$ and V$_4$ combine to become CR$^4$R$^{4a}$, NR$^5$, O, CR$^4$ or N, with the proviso that the resulted structure is stable.

In certain embodiments, each of W$_1$, W$_2$, W$_3$ and W$_4$ disclosed herein is independently CR$^4$R$^{4a}$, NR$^5$, CR$^4$ or N, or W$_1$ and W$_2$ or W$_3$ and W$_4$ combine to become CR$^4$R$^{4a}$, NR$^5$, O or S.

In some embodiments, each X$_1$ disclosed herein is independently (CR$^4$R$^{4a}$)$_m$, NR$^5$, O, S, S=O or SO$_2$, where m is 0, 1 or 2. In other embodiments, each X$_1$ disclosed herein is independently O or NR$^5$. In further embodiments, each of X$_2$ and X$_3$ disclosed herein is independently O, S or NR$^5$.

In certain embodiments, each Z disclosed herein is independently —NR$^5$C(=O)(CR$^4$R$^{4a}$)$_p$—, —NR$^5$C(=S)(CR$^4$R$^{4a}$)$_p$—, —NR$^{5a}$(CR$^4$R$^{4a}$)$_p$—, —NR$^5$(CR$^4$R$^{4a}$)$_p$C(=O)—, —NR$^5$(CR$^4$R$^{4a}$)$_p$C(=S)—, —NR$^5$S(=O)$_r$—, —NR$^5$S(=O), (CR$^4$R$^{4a}$)$_p$—, —C(=O)NR$^5$(CR$^4$R$^{4a}$)$_p$— or —NR$^5$(CR$^4$R$^{4a}$)$_p$S(=O)$_r$—, where p is 0, 1, 2 or 3; and r is 1 or 2.

In some embodiments, Z of formula (IIa) is —NHC(=O)—; Z$_1$ of formula (IIb) is NH; and the substructure defined by X$_1$, U$_1$ and R$^3$ of Formula I is:

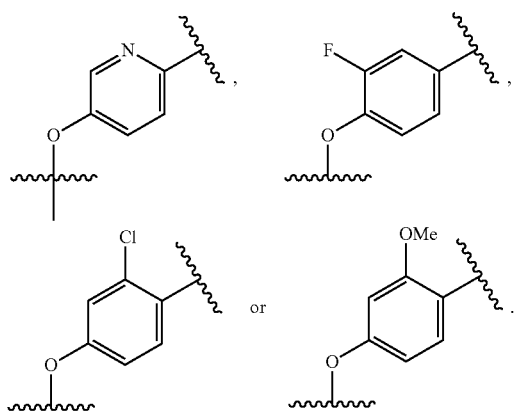

In some embodiments, each of R$^4$ and R$^{4a}$ disclosed herein is independently H, F, Cl, Br, I, —CN, hydroxyl, —NR$^{5a}$R$^5$, alkoxy, cycloalkoxy, heterocycloalkoxy, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl, with the proviso that where R$^4$ and R$^{4a}$ are bonded to the same carbon atom, R$^4$ and R$^{4a}$, together with the carbon atom they are attached to, optionally form a substituted or unsubstituted 3-8 membered carbocyclic or heterocyclic ring.

In certain embodiments, each of R$^5$ and R$^{5a}$ is independently H, R$^6$R$^{6a}$NC(=O)—, R$^6$OC(=O)—, R$^6$C(=O)—, R$^6$R$^{6a}$NS(=O)—, R$^6$OS(=O)—, R$^6$S(=O)—, R$^6$R$^{6a}$NSO$_2$—, R$^6$OSO$_2$—, R$^6$SO$_2$—, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl, with the proviso that where R$^5$ and R$^{5a}$ are bonded to the same nitrogen atom, R$^5$ and R$^{5a}$, together with the nitrogen atom they are attached to, optionally form a substituted or unsubstituted 3-8 membered ring, including spiro and fused bicyclic rings.

In certain embodiments, each of R$^6$ and R$^{6a}$ is independently H, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl, carbocyclyl.

In some embodiments, each of R$^{5a}$R$^5$N—, —C(=O)NR$^5$R$^{5a}$, —OC(=O)NR$^5$R$^{5a}$, —OC(=O)OR$^5$, —NR$^5$C(=O)NR$^5$R$^{5a}$, —NR$^5$C(=O)OR$^{5a}$, —NR$^5$C(=O)—R$^{5a}$, R$^5$R$^{5a}$N—O$_2$S—, R$^5$O$_2$S—, R$^5$O$_2$SR$^{5a}$N—, OR$^5$, NR$^5$, CR$^4$R$^{4a}$, CR$^4$, (CR$^4$R$^{4a}$)$_m$, —NR$^5$C(=O)—(CR$^4$R$^{4a}$)$_p$—, —NR$^5$C(=S)—(CR$^4$R$^{4a}$)$_p$—, —NR$^{5a}$—(CR$^4$R$^{4a}$)$_p$—, —NR$^5$—(CR$^4$R$^{4a}$)$_p$C(=O)—, —NR$^5$—(CR$^4$R$^{4a}$)$_p$C(=S)—, —NR$^5$S(=O)$_r$—, —NR$^5$S(=O)(CR$^4$R$^{4a}$)$_p$—, —C(=O)NR$^5$—(CR$^4$R$^{4a}$)$_p$— or —NR$^5$—(CR$^4$R$^{4a}$)$_p$—S(=O)$_r$, R$^{5a}$R$^5$N-alkyl, R$^5$(S(=O)$_r$-alkyl, R$^5$R$^{5a}$N—C(=O)—C$_{1-6}$alkyl, R$^{5a}$R$^5$N—C$_{1-6}$ alkoxy, R$^5$S(=O)$_r$-alkoxy, R$^5$R$^{5a}$N—C(=O)-alkoxy, R$^6$R$^{6a}$NC(=O)—, R$^6$OC(=O)—, R$^6$C(=O)—, R$^6$R$^{6a}$NS(=O)—, R$^6$OS(=O)—, R$^6$S(=O)—, R$^6$R$^{6a}$NSO$_2$—, R$^6$OSO$_2$—, R$^6$SO$_2$—, aliphatic, alkoxy, hydroxyalkoxy, aminoalkoxy, hydroxy-substituted aminoalkoxy, haloalkoxy, amino-substituted haloalkoxy, alkylamino haloalkoxy, hydroxy-substituted haloalkoxy, alkylaminoalkoxy, alkoxyalkoxy, arylalkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, aryloxy, heterocyclyloxyalkoxy, carbocyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicycloxoalkoxy, fused heterobicycloxoalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)NR$^5$—, fused heterobicyclyl-C(=O)NR$^5$—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicycloxoalkoxy, spiro heterobicycloxoalkoxy, spiro bicyclylaminoalkoxy, spiro heterobicyclylaminoalkoxy, spiro bicyclyl —C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)NR$^5$—, or spiro heterobicyclyl-C(=O)NR$^5$—, aryl, heteroaryl, arylaliphatic and heteroarylaliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocycly- loxyaliphatic, cycloalkyloxyaliphatic, arylaminoaliphatic, heterocyclylaminoaliphatic, cycloalkylaminoaliphatic, heterocyclyl and carbocyclyl disclosed herein is independently substituted or unsubstituted.

In another aspect, provided herein are pharmaceutical compositions comprising a compound disclosed herein, or a stereoisomer, geometric isomer, tautomer, solvate, metabolite, pharmaceutically acceptable salt or prodrug thereof, and an optional pharmaceutically acceptable carrier, excipient, diluent, adjuvant, vehicle or a combination thereof. In certain embodiments, the compound is an inhibitor of protein tyrosine kinase. In other embodiments, the compound is an inhibitor of VEGF receptor signaling, HGF receptor signaling and/or IGF receptor signaling.

In some embodiments, the composition disclosed herein further comprises an additional therapeutic agent. In other embodiments, the therapeutic agent is a chemotherapeutic agent, an anti-proliferative agent, an agent for treating atherosclerosis, an agent for treating lung fibrosis, and combinations thereof.

In further embodiments, the therapeutic agent is adriamycin, rapamycin, temsirolimus, everolimus, ixabepilone, gemcitabine, cyclophosphamide, dexamethasone, etoposide, fluorouracil, imatinib mesylate, dasatinib, nilotinib, erlotinib, lapatinib, iressa, sorafenib, sunitinib, an interferon, carboplatin, topotecan, taxol, vinblastine, vincristine, temozolomide, tositumomab (Bexxar), trabedectin, Avastin (bevacizumab), Herceptin (trastuzumab), Erbitux (cetuximab), Vectibix (panitumumab) or a combination thereof.

In another aspect, provided herein are methods for preventing, managing, treating or lessening the severity of a proliferative disorder in a patient infected with the proliferative disorder, which comprises administrating a pharmaceutically effective amount of a compound disclosed herein to the patient.

In another aspect, provided herein are methods for preventing, managing, treating or lessening the severity of a proliferative disorder in a patient infected with the proliferative disorder, which comprises administrating a pharmaceutically effective amount of a pharmaceutical composition disclosed herein to the patient.

In another aspect, provided herein is use of the compound disclosed herein in the manufacture of a medicament for preventing, managing, treating or lessening the severity of a proliferative disorder in a patient.

In another aspect, provided herein is use of the pharmaceutical composition disclosed herein in the manufacture of a medicament for preventing, managing, treating or lessening the severity of a proliferative disorder in a patient.

In some embodiments, the proliferative disorder is metastatic cancer. In other embodiments, the proliferative disorder is colon cancer, gastric adenocarcinoma, bladder cancer, breast cancer, kidney cancer, liver cancer, lung cancer, thyroid cancer, cancer of the head and neck, prostate cancer, pancreatic cancer, cancer of the CNS, glioblastoma, or a myeloproliferative disorder. In further embodiments, the proliferative disorder is atherosclerosis or lung fibrosis.

In another aspect, provided herein is a method of inhibiting or modulating protein kinase activity in a biological sample comprising contacting a biological sample with the compound disclosed herein.

In another aspect, provided herein is a method of inhibiting or modulating protein kinase activity in a biological sample comprising contacting a biological sample with the pharmaceutical composition disclosed herein.

In some embodiments, the protein kinases are receptor tyrosine kinases. In other embodiments, the receptor tyrosine kinases are KDR, c-Met or IGF1R.

In another aspect, provided herein is a method of inhibiting protein tyrosine kinase, the method comprises contacting the kinase with a compound disclosed herein, or with a composition disclosed herein. In other embodiments, provided herein is a method of inhibiting VEGF receptor signaling, HGF receptor signaling and/or IGF receptor signaling, the method comprises contacting the receptor with a compound disclosed herein, or with a composition disclosed herein. Inhibition of receptor protein kinase activity, in some embodiments, VEGF, HGF and/or IGF receptor signaling, can be in a cell or a multicellular organism. If in a multicellular organism, the method disclosed herein comprises administering to the organism a compound disclosed herein, or a composition disclosed herein. In some embodiments, the organism is a mammal; in other embodiments, the organism is a human. In still other embodiments, the method further comprises contacting the kinase with an additional therapeutic agent.

In another aspect, provided herein is a method of inhibiting proliferative activity of a cell, the method comprising contacting the cell with an effective proliferative inhibiting amount of a compound disclosed herein or a composition thereof. In other embodiments, the method further comprises contacting the cell with an additional therapeutic agent.

In another aspect, provided herein is a method of treating a cell proliferative disease in a patient, the method comprises administering to the patient in need of such treatment an effective therapeutic amount of a compound disclosed herein or a composition thereof. In other embodiments, the method further comprises administering an additional therapeutic agent.

In another aspect, provided herein is a method of inhibiting tumor growth in a patient, the method comprises administering to the patient in need thereof an effective therapeutic amount of a compound disclosed herein or a composition thereof. In other embodiments, the method further comprises administering an additional therapeutic agent.

In another aspect, provided herein include methods of preparing, methods of separating, and methods of purifying compounds of Formula (I), (IV) or (V).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and *the Handbook of Chemistry and Physics*, 75$^{th}$ Ed. 1994. Additionally, general principles of organic chemistry are described in "*Organic Chemistry*", Thomas Sorrell, University Science Books, Sausalito: 1999, and "*March's Advanced Organic Chemistry*" by Michael B. Smith and Jerry March, John Wiley & Sons, New York: 2007, the entire contents of which are hereby incorporated by reference.

As described herein, compounds may optionally be substituted with one or more substituents, such as are illustrated generally above, or as exemplified by particular classes, subclasses, and species disclosed herein. It will be appreciated that the phrase "optionally substituted" is used interchangeably with the phrase "substituted or unsubstituted". In general, the term "substituted" whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

The term "aliphatic" or "aliphatic group" as used herein, refers to a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups.

The term "alkyl" as used herein refers to a saturated linear or branched-chain monovalent hydrocarbon radical of one to twenty carbon atoms, wherein the alkyl radical may be optionally substituted independently with one or more substituents described below. Further examples of aliphatic groups include, but are not limited to, methyl(Me, —CH$_3$), ethyl(Et, —CH$_2$CH$_3$), 1-propyl(n-Pr, n-propyl, —CH$_2$CH$_2$CH$_3$), 2-propyl(i-Pr, i-propyl, —CH(CH$_3$)$_2$), 1-butyl(n-Bu, n-butyl, —CH$_2$CH$_2$CH$_2$CH$_3$), 2-methyl-1-propyl(i-Bu, i-butyl, —CH$_2$CH(CH$_3$)$_2$), 2-butyl(s-Bu, s-butyl, —CH(CH$_3$)CH$_2$CH$_3$), 2-methyl-2-propyl(t-Bu, t-butyl, —C(CH$_3$)$_3$), 1-pentyl(n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like. The terms "alkyl" and the prefix "alk-" as used herein, are inclusive of both straight chain and branched saturated carbon chain. The term "alkylene", as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡H), propynyl (propargyl, —CH$_2$C≡H), and the like.

The term "cycloaliphatic" (or "carbocycle", "carbocyclyl", "carbocyclic ring" and "cycloalkyl") refers to a monovalent or multivalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system. Suitable cycloaliphatic groups include, but are not limited to, cycloalkyl, cycloalkenyl, and cycloalkynyl. Further examples of cycloaliphatic groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "heterocycle", "heterocyclyl", "heterocycloaliphatic", or "heterocyclic" as used interchangeably herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. One or more ring atoms are optionally substituted independently with one or more substituents described below. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or SO$_2$, PO or PO$_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or SO$_2$, PO or PO$_2$).

The heterocyclyl may be a carbon radical or heteroatom radical. "Heterocyclyl" also includes radicals where heterocycle radicals are fused with a saturated, partially unsaturated ring, or heterocyclic ring. Examples of heterocyclic rings include, but are not limited to, pyrrolidinyl, tetrahydrofliranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 1,2,3,4-tetrahydroisoquinolinyl, 3-azabicyco[3.1.0]hexanyl, 3-azabicyclo [4.1.0]heptanyl, azabicyclo[2.2.2]hexanyl, 3H-indolyl quinolizinyl and N-pyridyl ureas. Some non-limiting examples of a heterocyclic ring include 1,1-dioxo-thiomorpholinyl and heterocyclic group wherein 2 carbon atoms on the ring are substituted with oxo (=O) moieties are pyrimidindionyl. The heterocyclic groups herein are optionally substituted independently with one or more substituents described herein.

The term "heterocyclylalkyl" refers to heterocyclic-substituted alkyl radical. The term "heterocyclylalkoxy" refers to heterocyclic-substituted alkoxy radical wherein oxygen atom serves as the attaching point to the rest of the molecule. The term "heterocyclylalkylamino" refers to heterocyclic-substituted alkylamino radical wherein nitrogen atom serves as the attaching point to the rest of the molecule. The term "heterocyclyloxy" refers to heterocyclic-substituted oxygen radical wherein oxygen atom serves as the attaching point to the rest of the molecule. The terms "heterocyclylamino" and "heterocyclylalkylamino" refers to heterocyclic-substituted nitrogen radical and heterocyclic- and alkyl-substituted nitrogen radical wherein nitrogen atom serves as the attaching point to the rest of the molecule.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to F, Cl, Br or I.

The term "unsaturated" as used herein, refers to that a moiety has one or more units of unsaturation.

The term "alkoxy" as used herein, refers to an alkyl group, as previously defined, attached to the principal carbon chain through an oxygen ("alkoxy") atom.

The terms "haloalkyl", "haloalkenyl" or "haloalkoxy" refers to alkyl, alkenyl, or alkoxy, as the case may be, substituted with one or more halogen atoms.

The term "aryl" used alone or as part of a larger moiety as in "aralkyl", "aralkoxy" or "aryloxyalkyl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings include phenyl, naphthyl, and anthracene.

The term "heteroaryl" used alone or as part of a larger moiety as in "heteroaralkyl" or "heteroarylalkoxy" refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic".

Some non-limiting examples of suitable heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl, or 4-isoquinolinyl).

The term "sulfonyl", whether used alone or linked to other terms such as alkylsulfonyl, refers to respectively divalent radicals —$SO_2$—. The term "alkylsulfonyl", refers to a sulfonyl radical substituted with an alkyl radical, forming a alkylsulfonyl (—$SO_2CH_3$).

The terms "sulfamyl", "aminosulfonyl" and "sulfonamidyl" refer to a sulfonyl radical substituted with an amine radical, forming a sulfonamide (—$SO_2NH_2$).

The term "carboxy" or "carboxyl", whether used alone or with other terms, such as "carboxyalkyl", refers to —$CO_2H$. The term "carbonyl", whether used alone or with other terms, such as "aminocarbonyl" or "carbonyloxy", refers to —(C=O)—.

The term "aralkyl" refers to aryl-substituted alkyl radicals. In some embodiments, aralkyl radicals are "lower aralkyl" radicals having aryl radicals attached to alkyl radicals having one to six carbon atoms. In other embodiments, aralkyl radicals are "phenylalkylenyl" attached to alkyl portions having one to three carbon atoms. Some non-limiting examples of such radicals include benzyl, diphenylmethyl and phenylethyl. The aryl in said aralkyl can be additionally substituted with halo, alkyl, alkoxy, haloalkyl and haloalkoxy.

The term "alkylthio" refers to radicals containing a linear or branched alkyl radical, of one to ten carbon atoms, attached to a divalent sulfur atom. In other embodiments alkylthio radicals are lower alkylthio radicals having one to three carbon atoms. Some non-limiting examples of "alkylthio" include methylthio ($CH_3S$—).

The term "haloalkylthio" refers to radicals containing a haloalkyl radical, of one to ten carbon atoms, attached to a divalent sulfur atom. In other embodiments, haloalkylthio radicals are lower haloalkylthio radicals having one to three carbon atoms. Some non-limiting examples of "haloalkylthio" include trifluoromethylthio.

The term "alkylamino" refers to "N-alkylamino" and "N,N-dialkylamino" where amino groups are independently substituted with one alkyl radical or with two alkyl radicals, respectively. In other embodiments, alkylamino radicals are "lower alkylamino" radicals having one or two alkyl radicals of one to six carbon atoms, attached to a nitrogen atom. In still other embodiments, alkylamino radicals are lower alkylamino radicals having one to three carbon atoms. Some non-limiting examples of suitable alkylamino radicals include mono or dialkylamino such as N-methylamino, N-ethylamino, N,N-dimethylamino, N,N-diethylamino, and the like.

The term "arylamino" refers to amino groups, which have been substituted with one or two aryl radicals, Some non-limiting examples of arylamino include N-phenylamino. In some embodiments, the arylamino radicals include substituted on the aryl ring portion of the radical.

The term "heteroarylamino" refers to amino groups, which have been substituted with one or two heteroaryl radicals, Some non-limiting examples of heteroarylamino include N-thienylamino. In other embodiments, the "heteroarylamino" radicals include substituted on the heteroaryl ring portion of the radical.

The term "aminoalkyl" refers to linear or branched alkyl radicals having one to about ten carbon atoms any one of which includes substituted with one or more amino radicals. In some embodiments, aminoalkyl radicals are "lower aminoalkyl" radicals having one to six carbon atoms and one or more amino radicals. Some non-limiting examples of such radicals include aminomethyl, aminoethyl, aminopropyl, aminobutyl or aminohexyl.

The term "alkylaminoalkyl" refers to alkyl radicals substituted with alkylamino radicals. In some embodiments, alkylaminoalkyl radicals are "lower alkylaminoalkyl" radicals having alkyl radicals of one to six carbon atoms. In other embodiments, alkylaminoalkyl radicals are lower alkylaminoalkyl radicals having alkyl radicals of one to three carbon atoms. Some non-limiting examples of suitable alkylaminoalkyl radicals include mono or dialkyl substituted, such as N-methylaminomethyl, N,N-dimethyl-aminoethyl, N,N-diethylaminomethyl, and the like.

The term "alkylaminoalkoxy" refers to alkoxy radicals substituted with alkylamino radicals. Some non-limiting examples of suitable alkylaminoalkoxy radicals include mono or dialkyl substituted, such as N-methylaminoethoxy, N,N-dimethylaminoethoxy, N,N-diethylaminoethoxy, and the like.

The term "alkylaminoalkoxyalkoxy" refers to alkoxy radicals substituted with alkylaminoalkoxy radicals. Some non-limiting examples of suitable alkylaminoalkoxyalkoxy radicals include mono or dialkyl substituted, such as N-methylaminomethoxyethoxy, N-methylaminoethoxyethoxy, N,N-dimethylaminoethoxyethoxy, N,N-diethylaminomethoxymethoxy, and the like.

The term "carboxyalkyl" refers to linear or branched alkyl radicals having one to about ten carbon atoms any one of which maybe substituted with one or more carboxy radicals. Some non-limiting examples of such radicals include carboxymethyl, carboxypropyl, and the like.

The term "aryloxy" refers to optionally substituted aryl radicals, as defined above, attached to an oxygen atom. Some non-limiting examples of such radicals include phenoxy.

The term "heteroaryloxy" refers to optionally substituted heteroaryl radicals, as defined above, attached to an oxygen atom.

The term "heteroarylalkoxy" refers to oxy-containing heteroarylalkyl radicals attached through an oxygen atom to other radicals.

The term "cycloalkylalkyl" refers to cycloalkyl-substituted alkyl radicals. Some non-limiting examples of such radicals include cyclohexylmethyl. The cycloalkyl in the radicals may be additionally substituted with halo, alkyl, alkoxy or hydroxy.

The terms "fused bicyclic", "fused cyclic", "fused bicyclyl" and "fused cyclyl" refer to saturated bridged ring system, which refers to a bicyclic ring system that is not aromatic. Such a system may contain isolated or conjugated unsaturation, but not aromatic or heteroaromatic rings in its core structure (but may have aromatic substitution thereon). Each cyclic ring in a fused bicyclyl can be either a carbocyclic or a heteroalicyclic. Some non-limiting examples of fused bicyclic ring system include hexahydro-furo[3,2-b]furan, 2,3,3a,4,7,7a-hexahydro-1H-indene, 7-azabicyclo[2.2.1]heptane, and 1,2,3,4,4a,5,8,8a-octahydro-naphthalene.

The terms "spirocyclyl", "spirocyclic", "spiro bicyclyl" or "spiro bicyclic" refer to a ring originating from a particular annular carbon of another ring. For example, as depicted below, a saturated bridged ring system (ring B and B') is termed as "fused bicyclic", whereas ring A and ring B share an atom between the two saturated ring system, which terms as a "spirocyclyl" or "spiro bicyclyl". Each cyclic ring in a spirocyclyl can be either a carbocyclic or a heteroalicyclic.

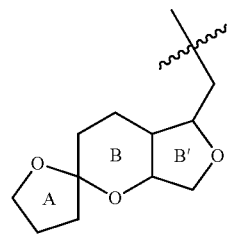

As described herein, a bond drawn from a substituent to the center of one ring within a ring system (as shown below) represents substitution of the substituent at any substitutable position on the rings to which it is attached. For example, Figure a represents possible substitution in any of the positions on the B ring shown in Figure b.

Figure a

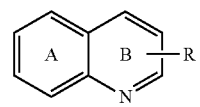

Figure b

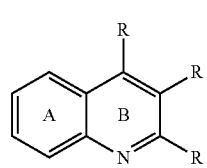

As described herein, a dot line drawn together with a bond within a ring system (as shown in Figure c) represents either a double bond or a single bond. For example, structure in Figure c represents any structures selected from Figure d.

Figure c

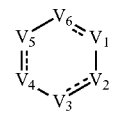

Figure d

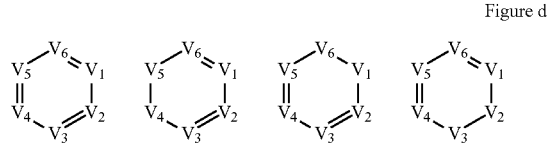

-continued

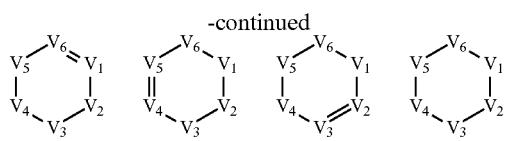

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" as used herein, represents a compound that is transformed in vivo into a compound of Formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, J. Rautio et al, Prodrugs: Design and Clinical Applications, *Nature Review Drug Discovery*, 2008, 7, 255-270, and S. J. Hecker et al, Prodrugs of Phosphates and Phosphonates, *Journal of Medicinal Chemistry*, 2008, 51, 2328-2345, each of which is incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salt" as used herein, refers to organic or inorganic salts of a compound disclosed herein. Pharmaceutically acceptable salts are well known in the art. For example, S. M. Berge et al., describe pharmaceutically acceptable salts in detail in J. *Pharmaceutical Sciences*, 66: 1-19, 1977, which is incorporated herein by reference. Examples of pharmaceutically acceptable, nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, methanesulfonate, 2-naphthalenesulfonate, nicotinate, nitrate, oleate, palmitate, pamoate, pectinate, persulfate, 3-phenylpropionate, phosphate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (Boc), benzyloxycarbonyl (Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting groups include —$CH_2CH_2SO_2Ph$, cyanoethyl, 2-(trimethylsilyl)ethyl, 2-(trimethylsilyl)ethoxy methyl, 2-(p-toluenesulfonyl)ethyl, 2-(p-nitrophenylsulfonyl)ethyl, 2-(diphenyl phosphino)-ethyl, nitroethyl, and the like. For a general description of protecting groups and their use, see T. W. Greene, *Protective Groups in Organic Synthesis*, John Wiley & Sons, New York, 1991; and P. J. Kocienski, *Protecting Groups*, Thieme, Stuttgart, 2005.

Description of Compounds of the Invention

Disclosed herein are heterocyclic compounds, and pharmaceutical formulations thereof, that are potentially useful in the treatment of diseases, conditions and/or disorders modulated by protein kinases, especially KDR, c-Met receptor and/or IGF receptor. More specifically, provided herein include compounds of Formula (I):

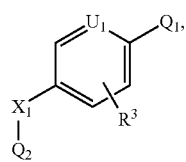
(I)

or a stereoisomer, a geometric isomer, a tautomer, an N-oxide, a hydrate, a solvate, a metabolite, a pharmaceutically acceptable salt or a prodrug thereof, wherein each of $R^3$, $U_1$, $X_1$, $Q_1$ and $Q_2$ is as defined herein.

In certain embodiments, $Q_1$ is Formula (IIa) or (IIb):

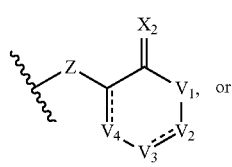
(IIa)

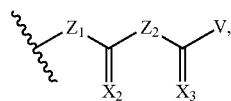
(IIb)

wherein each of V, $V_1$, $V_2$, $V_3$, $V_4$, $X_2$, $X_3$, Z, $Z_1$, and $Z_2$ is as defined herein; and $Q_2$ is Formula (III):

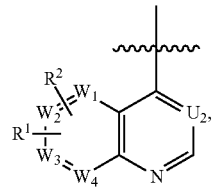
(III)

wherein each of $R^1$, $R^2$, $W_1$, $W_2$, $W_3$, $W_4$ and $U_2$ is as defined herein.

In some embodiments, the compounds have Formula (IV) or (V):

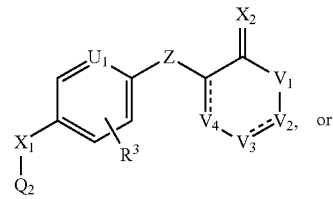
(IV)

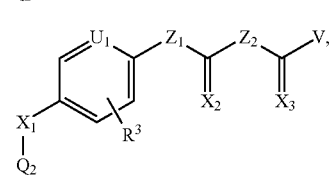
(V)

or a stereoisomer, a geometric isomer, a tautomer, an N-oxide, a hydrate, a solvate, a metabolite, a pharmaceutically acceptable salt or a prodrug thereof, wherein each of $R^3$, $U_1$, V, $V_1$, $V_2$, $V_3$, $V_4$, $X_1$, $X_2$, $X_3$, Z, $Z_1$, $Z_2$ and $Q_2$ is as defined herein, wherein:

each of $R^1$ and $R^2$ is independently H, halo, cyano(CN), hydroxyl, $R^{5a}R^5N$—, —C(=O)$NR^5R^{5a}$, —OC(=O)$NR^5R^{5a}$, —OC(=O)$OR^5$, —$NR^5C$(=O)$NR^5R^{5a}$, —$NR^5C$(=O)$OR^{5a}$, —$NR^5C$(=O)$R^{5a}$, $R^5R^{5a}N$—$O_2S$—, $R^5O_2S$—, $R^5O_2S$—$R^{5a}N$—, $R^{5a}R^5N$-alkyl, $R^5S(=O)_r$-alkyl, $R^5R^{5a}N$—C(=O)alkyl, $R^{5a}R^5N$-alkoxy, $R^5S(=O)_r$-alkoxy, $R^5R^{5a}N$—C(=O)-alkoxy, aliphatic, alkoxy, hydroxyalkoxy, aminoalkoxy, hydroxy-substituted aminoalkoxy, haloalkoxy, amino-substituted haloalkoxy, alkylamino haloalkoxy, hydroxy-substituted haloalkoxy, alkylaminoalkoxy, alkoxyalkoxy, arylalkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, aryloxy, heterocyclyloxyalkoxy, carbocyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)NR$^5$—, fused heterobicyclyl-C(=O)NR$^5$—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicycloxoalkoxy, spiro heterobicycloxoalkoxy, spiro bicyclylaminoalkoxy, spiro heterobicyclylaminoalkoxy, spiro bicyclyl —C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)NR$^5$—, or spiro heterobicyclyl-C(=O)NR$^5$—, aryl, heteroaryl, arylaliphatic, heteroarylaliphatic; and each of alkoxy and alkylamino moiety is independently substituted with one or more hydroxy groups, amino groups or substituted amino groups;

each of R$^3$ and R$^{3a}$ is one or more substituents independently H, F, Cl, Br, I, —CN, hydroxyl, R$^{5a}$R$^5$N—, R$^{5a}$R$^5$N-aliphatic, hydroxyaliphatic, aliphatic, alkoxy, alkoxyaliphatic, haloalkyl, heterocyclyl, heterocyclylalkyl, cycloalkyl, cycloalkoxy aliphatic, heterocycloxy aliphatic, cycloalkylalkoxy, heterocyclylalkoxy, aryloxyalkyl, heteroaryloxy aliphatic, arylaliphatic, heteroaryl aliphatic, aryl, or heteroaryl.

each of U$_1$ and U$_2$ is independently CR$^4$ or N;

V is NR$^5$R$^{5a}$, OR$^5$, aliphatic, cycloalkyl, heterocyclyl, aryl, heteroaryl, arylaliphatic or heteroarylaliphatic;

V$_1$ is O or NR$^5$;

each of V$_2$, V$_3$, V$_4$ is independently CR$^4$R$^{4a}$, NR$^5$, CR$^4$ or N, with the proviso that only one of V$_2$, V$_3$ and V$_4$ is NR$^5$ or N; V$_2$ and V$_3$ or V$_3$ and V$_4$ may combine to become CR$^4$R$^{4a}$, NR$^5$, O, CR$^4$ or N, with the proviso that the resulted structures are stable;

each of W$_1$, W$_2$, W$_3$, W$_4$ is independently CR$^4$R$^{4a}$, NR$^5$, CR$^4$ or N; W$_1$ and W$_2$ or W$_3$ and W$_4$ may combine to become CR$^4$R$^{4a}$, NR$^5$, O or S;

X$_1$ is (CR$^4$R$^{4a}$)$_m$, NR$^5$, O, S, S=O or SO$_2$; m is 0, 1, or 2;

each of X$_2$ and X$_3$ is independently O, S or NR$^5$;

Z is —NR$^5$C(=O)(CR$^4$R$^{4a}$)$_p$—, —NR$^5$C(=S)(CR$^4$R$^{4a}$)$_p$—, —NR$^{5a}$(CR$^4$R$^{4a}$)$_p$—, —NR$^5$(CR$^4$R$^{4a}$)$_p$C(=O)—, —NR$^5$(CR$^4$R$^{4a}$)$_p$C(=S)—, —NR$^5$S(=O)$_r$—, —NR$^5$S(=O)$_r$(CR$^4$R$^{4a}$)$_p$—, —C(=O)NR$^5$(CR$^4$R$^{4a}$)$_p$— or —NR$^5$(CR$^4$R$^{4a}$)$_p$S(=O)$_r$—, where p is 0, 1, 2 or 3; and r is 1, or 2;

each of Z$_1$ and Z$_2$ is independently NR$^5$ or CR$^4$R$^{4a}$;

each of R$^4$ and R$^{4a}$ is independently H, F, Cl, Br, I, —CN, hydroxyl, —NR$^{5a}$R$^5$, alkoxy, cycloalkoxy, heterocycloalkoxy, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl, with the proviso that where R$^4$ and R$^{4a}$ are bonded to the same carbon atom, R$^4$ and R$^{4a}$, together with the carbon atom they are attached to, optionally form a substituted or unsubstituted 3-8 membered carbocyclic or heterocyclic ring;

each of R$^5$ and R$^{5a}$ is independently H, R$^6$R$^{6a}$NC(=O)—, R$^6$OC(=O)—, R$^6$C(=O)—, R$^6$R$^{6a}$NS(=O)—, R$^6$OS(=O)—, R$^6$S(=O)—, R$^6$R$^{6a}$NSO$_2$—, R$^6$OSO$_2$—, R$^6$SO$_2$—, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl, with the proviso that where R$^5$ and R$^{5a}$ are bonded to the same nitrogen atom, R$^5$ and R$^{5a}$, together with the nitrogen atom they are attached to, optionally form a substituted or unsubstituted 3-8 membered ring, including spiro and fused bicyclic rings; and each of R$^6$ and R$^{6a}$ is independently H, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl, carbocyclyl.

In some embodiments, each of R$^{5a}$R$^5$N—, —C(=O)NR$^5$R$^{5a}$, —OC(=O)NR$^5$R$^{5a}$, —OC(=O)OR$^5$, —NR$^5$C(=O)NR$^5$R$^{5a}$, —NR$^5$C(=O)OR$^{5a}$, —NR$^5$C(=O)—R$^{5a}$, R$^5$R$^{5a}$N—O$_2$S—, R$^5$O$_2$S—, R$^5$O$_2$SR$^{5a}$N—, OR$^5$, NR$^5$, CR$^4$R$^{4a}$, CR$^4$, (CR$^4$R$^{4a}$)$_m$, —NR$^5$C(=O)—(CR$^4$R$^{4a}$)$_p$—, —NR$^5$C(=S)—(CR$^4$R$^{4a}$)$_p$—, —NR$^{5a}$—(CR$^4$R$^{4a}$)$_p$—, —NR$^5$—(CR$^4$R$^{4a}$)$_p$C(=O)—, —NR$^5$—(CR$^4$R$^{4a}$)$_p$C(=S)—, —NR$^5$S(=O)$_r$—, —NR$^5$S(=O)$_r$(CR$^4$R$^{4a}$)$_p$—, —C(=O)NR$^5$—(CR$^4$R$^{4a}$)$_p$— or —NR$^5$—(CR$^4$R$^{4a}$)$_p$—S(=O)$_r$, R$^{5a}$R$^5$N-alkyl, R$^5$S(=O)$_r$-alkyl, R$^5$R$^{5a}$N—C(=O)-alkyl, R$^{5a}$R$^5$N-alkoxy, R$^5$S(=O)$_r$-alkoxy, R$^5$R$^{5a}$N—C(=O)-alkoxy, R$^6$R$^{6a}$NC(=O)—, R$^6$OC(=O)—, R$^6$C(=O)—, R$^6$R$^{6a}$NS(=O)—, R$^6$OS(=O)—, R$^6$S(=O)—, R$^6$R$^{6a}$NSO$_2$—, R$^6$OSO$_2$—, R$^6$SO$_2$—, aliphatic, alkoxy, hydroxyalkoxy, aminoalkoxy, hydroxy-substituted aminoalkoxy, haloalkoxy, amino-substituted haloalkoxy, alkylamino haloalkoxy, hydroxy-substituted haloalkoxy, alkylaminoalkoxy, alkoxyalkoxy, arylalkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, aryloxy, heterocyclyloxyalkoxy, carbocyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicycloxoalkoxy, fused heterobicycloxoalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)NR$^5$—, fused heterobicyclyl-C(=O)NR$^5$—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicycloxoalkoxy, spiro heterobicycloxoalkoxy, spiro bicyclylaminoalkoxy, spiro heterobicyclylaminoalkoxy, spiro bicyclyl —C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)NR$^5$—, or spiro heterobicyclyl-C(=O)NR$^5$—, aryl, heteroaryl, arylaliphatic and heteroarylaliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, heterocyclyl and carbocyclyl is independently substituted or unsubstituted.

In another embodiment, each of R$^1$ and R$^2$ is independently H, halo, cyano(CN), hydroxyl, R$^{5a}$R$^5$N—, —C(=O)NR$^5$R$^{5a}$, —OC(=O)NR$^5$R$^{5a}$, —OC(=O)OR$^5$, —NR$^5$C (=O)NR⁵R⁵ᵃ, —NR⁵C(=O)OR⁵ᵃ, —NR⁵C(=O)—R⁵ᵃ, R⁵R⁵ᵃN—O₂S—, R⁵O₂S—, R⁵O₂SR⁵ᵃN—, R⁵ᵃR⁵N—C₁₋₆ alkyl, R⁵S(=O)ₙ—C₁₋₆alkyl, R⁵R⁵ᵃN—C(=O)—C₁₋₆ alkyl, R⁵ᵃR⁵N—C₁₋₆ alkoxy, R⁵S(=O)ᵣ-alkoxy, R⁵R⁵ᵃN—C(=O)-alkoxy, optionally substituted C₁₋₆ aliphatic, optionally substituted C₁₋₆ alkylamino-C₁₋₆ alkyl, C₁₋₆ alkoxy-C₁₋₆ alkyl, optionally substituted C₃₋₁₀ heterocyclyl-C₁₋₆ alkyl, C₁₋₆ alkoxy-C₁₋₆ alkoxy, C₁₋₆ alkylthio-C₁₋₃alkoxy, —C₁₋₆ alkoxy-NR⁵ᵃ—C(=O)—OR⁵, —C₁₋₃ alkoxy-NR⁵ᵃ—C(=O)—R⁵, —C₁₋₃ alkoxy-C(=O)—C₁₋₃ alkyl, C₁₋₆ alkoxy, hydroxy-C₁₋₆ alkoxy, amino-C₁₋₆ alkoxy, hydroxy-substituted amino-C₁₋₆ alkoxy, C₁₋₆ haloalkoxy, amino-substituted-C₁₋₆ haloalkoxy, C₁₋₆ alkylamino-C₁₋₆ haloalkoxy, hydroxy-substituted-C₁₋₆ haloalkoxy, C₁₋₆ alkylamino-C₁₋₆ alkoxy, aryl-C₁₋₆ alkoxy, optionally substituted C₄₋₁₀ heterocyclyl-C₁₋₆ alkoxy, optionally substituted C₄₋₁₀ cycloalkyl-C₁₋₆ alkoxy, optionally substituted C₄₋₁₀ heterocyclyl(hydroxy-C₁₋₆ alkoxy), optionally substituted C₃₋₁₀ cycloalkyl(hydroxy-C₁₋₆ alkoxy), aryl(hydroxy-C₁₋₆ alkoxy), aryloxy-C₁₋₆ alkoxy, optionally substituted C₄₋₁₀ heterocyclyloxy-C₁₋₆ alkoxy, optionally substituted C₃₋₁₀ cycloalkyloxy-C₁₋₆ alkoxy, optionally substituted C₆₋₁₀ aryloxy, optionally substituted C₄₋₁₀ heterocyclyloxy, optionally substituted C₃₋₁₀ cycloalkyloxy, optionally substituted C₄₋₁₀ (heterocyclo)hydroxy-C₁₋₆ alkoxy, halo-C₁₋₆ alkoxy, azido-C₁₋₆ alkoxy, optionally substituted aryl-C₁₋₆ alkoxy, optionally substituted C₁₋₆-alkoxy, optionally substituted C₃₋₇ cycloalkoxy, optionally substituted C₄₋₁₀ heterocycloalkoxy, optionally substituted C₆₋₁₀ heteroarylalkoxy, optionally substituted C₅₋₁₂ fused bicyclyl, optionally substituted C₅₋₁₂ fused heterobicyclyl, optionally substituted C₅₋₁₂ fused bicyclyl C₁₋₃ aliphatic, optionally substituted C₅₋₁₂ fused heterobicyclyl C₁₋₃ aliphatic, optionally substituted C₅₋₁₂ fused bicycloxy, optionally substituted C₅₋₁₂ fused bicyclylamino, optionally substituted C₅₋₁₂ fused bicycloxo C₁₋₆-alkoxy, optionally substituted C₅₋₁₂ fused bicyclylamino C₁₋₆ alkoxy, optionally substituted C₅₋₁₂ fused bicyclyl-C(=O)—, optionally substituted C₅₋₁₂ fused bicyclyl-C(=O)O—, optionally substituted C₅₋₁₂ fused heterobicyclyl-C(=O)—, optionally substituted C₅₋₁₂ fused heterobicyclyl-C(=O)O—, optionally substituted C₅₋₁₂ fused bicyclylamino-C(=O)—, optionally substituted C₅₋₁₂ fused heterobicyclylamino-C(=O)—, optionally substituted C₅₋₁₂ fused bicyclyl-C(=O)NR⁵—, optionally substituted C₅₋₁₂ fused heterobicyclyl-C(=O)NR⁵—, optionally substituted C₅₋₁₂ spiro bicyclyl, optionally substituted C₅₋₁₂ spiro heterobicyclyl, optionally substituted C₅₋₁₂ spiro bicyclyl C₁₋₃ aliphatic, optionally substituted C₅₋₁₂ spiro heterobicyclyl C₁₋₃ aliphatic, optionally substituted C₅₋₁₂ spiro bicycloxo C₁₋₆ alkoxy, optionally substituted C₅₋₁₂ spiro bicyclylamino C₁₋₆ alkoxy, optionally substituted C₅₋₁₂ spiro bicycloxy, optionally substituted C₅₋₁₂ spiro bicyclylamino, optionally substituted C₅₋₁₂ fused heterobicycloxy, optionally substituted C₅₋₁₂ fused heterobicyclylamino, optionally substituted C₅₋₁₂ fused heterobicycloxo C₁₋₆ alkoxy, optionally substituted C₅₋₁₂ fused heterobicyclylamino C₁₋₆ alkoxy, optionally substituted C₅₋₁₂ spiro heterobicycloxo C₁₋₆ alkoxy, optionally substituted C₅₋₁₂ spiro heterobicyclylamino C₁₋₆ alkoxy, optionally substituted C₅₋₁₂ spiro heterobicycloxy, optionally substituted C₅₋₁₂ spiro heterobicyclylamino, optionally substituted C₅₋₁₂ spiro bicyclyl-C(=O)—, optionally substituted C₅₋₁₂ spiro bicyclyl-C(=O)O—, optionally substituted C₅₋₁₂ spiro heterobicyclyl-C(=O)—, optionally substituted C₅₋₁₂ spiro heterobicyclyl-C(=O)O—, optionally substituted C₅₋₁₂ spiro bicyclylamino-C(=O)—, optionally substituted C₅₋₁₂ spiro heterobicyclylamino-C(=O)—, optionally substituted C₅₋₁₂ spiro bicyclyl-C(=O)NR⁵—, or optionally substituted C₅₋₁₂ spiro heterobicyclyl-C(=O)NR⁵—, optionally substituted C₆₋₁₀ aryl, optionally substituted C₁₋₁₀ heteroaryl, optionally substituted C₆₋₁₀ aryl C₁₋₆ aliphatic or optionally substituted C₁₋₁₀ heteroaryl C₁₋₆ aliphatic; and each of the above-mentioned alkoxy and alkylamino moiety maybe independently substituted with one or more hydroxy groups, amino groups or substituted amino groups;

each of R³ and R³ᵃ is independently H, F, Cl, Br, I, —CN, hydroxyl, R⁵ᵃR⁵N—, R⁵ᵃR⁵N—C₁₋₃aliphatic, hydroxy C₁₋₃aliphatic, C₁₋₃aliphatic, C₁₋₃alkoxy, C₁₋₃alkoxy C₁₋₃aliphatic, C₁₋₃haloalkyl, C₃₋₆heterocyclyl, C₃₋₆heterocyclyl C₁₋₃alkyl, C₃₋₆cycloalkyl, C₃₋₆cycloalkoxy C₁₋₃aliphatic, C₃₋₆heterocycloxy C₁₋₃aliphatic, C₁₋₃cycloalkyl C₁₋₃alkoxy, C₃₋₆heterocyclyl C₁₋₃alkoxy, C₆₋₁₀aryloxy C₁₋₃alkyl, C₁₋₁₀heteroaryloxy C₁₋₃aliphatic, aryl C₁₋₃aliphatic, C₁₋₁₀heteroaryl C₁₋₃aliphatic, C₆₋₁₀aryl, or C₁₋₁₀heteroaryl;

each of U₁ and U₂ is independently CR⁴, or N; and

V is NR⁵R⁵ᵃ, optionally substituted C₁₋₆ aliphatic, optionally substituted C₆₋₁₀aryl, optionally substituted C₆₋₁₀ heteroaryl, optionally substituted C₆₋₁₀ aryl C₁₋₆ aliphatic, or optionally substituted C₆₋₁₀ heteroaryl C₁₋₆ aliphatic.

In another embodiment, formula (IIa) is

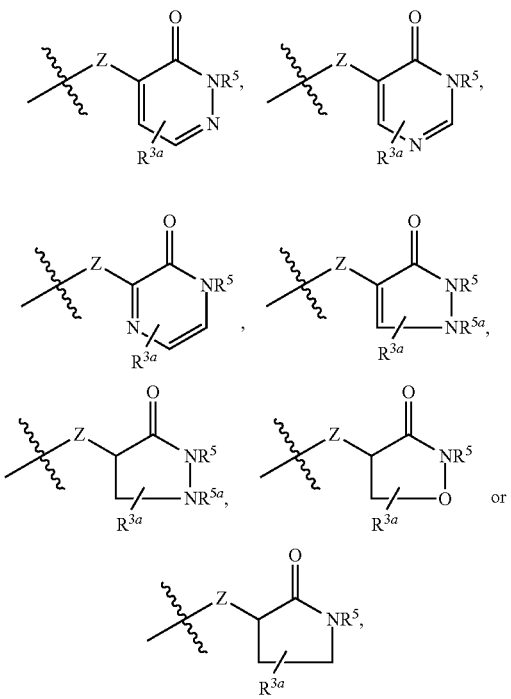

wherein R³ᵃ, R⁵, and R⁵ᵃ are as defined herein.

In another embodiment, Q₂ is:

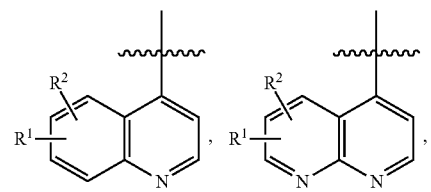

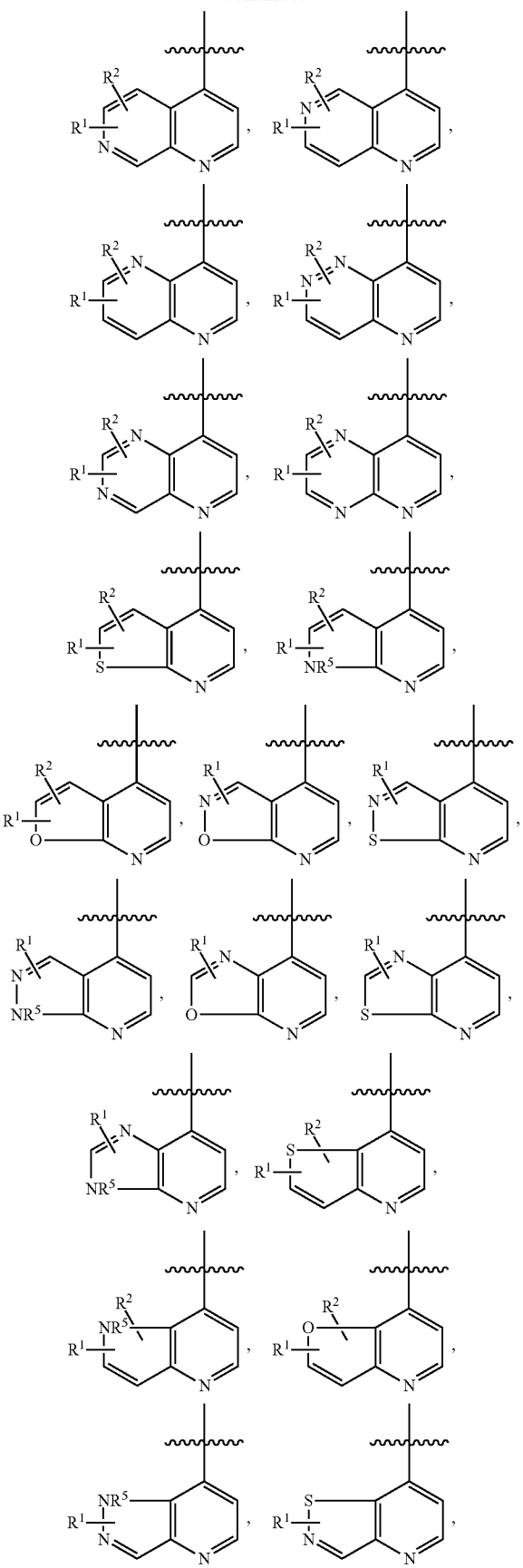

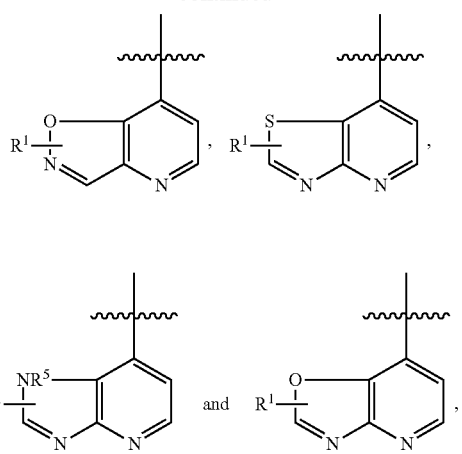

wherein $R^1$, $R^2$ and $R^5$ are as defined herein.

In another embodiment, $X_1$ is O, or $NR^5$;

Z is —NH—C(=O)—; and each of $Z_1$ and $Z_2$ is independently $NR^5$ or $CR^4R^{4a}$; with the proviso that $R^4$ and $R^{4a}$, together with the carbon atom they are attached to, may optionally form a substituted or unsubstituted 3-8 membered carobcyclic or heterocyclic ring.

In another embodiment, the substructure defined by $X_1$, Z, $U_1$ and $R_3$ is one of the following formulae:

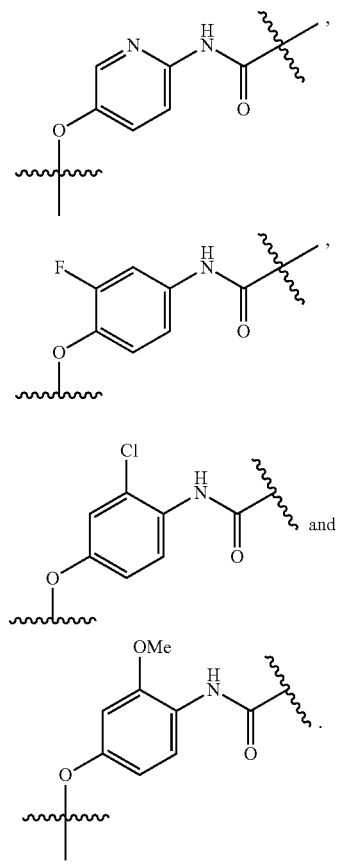

In another embodiment, Formula (IIb) is:
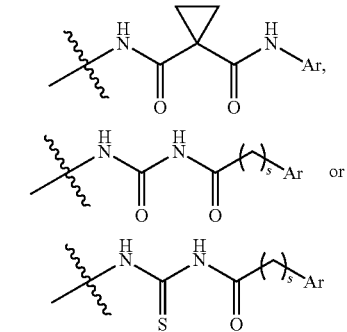
wherein Ar is substituted or unsubstituted aryl or heteroaryl; and s is 0 or 1.
In another embodiment, $R^1$ has one of the following structures:
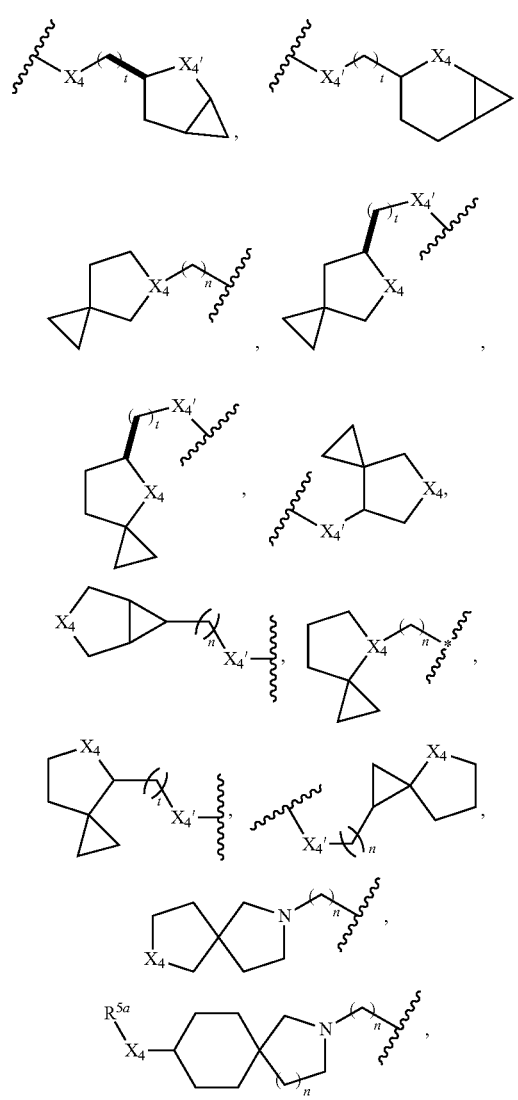
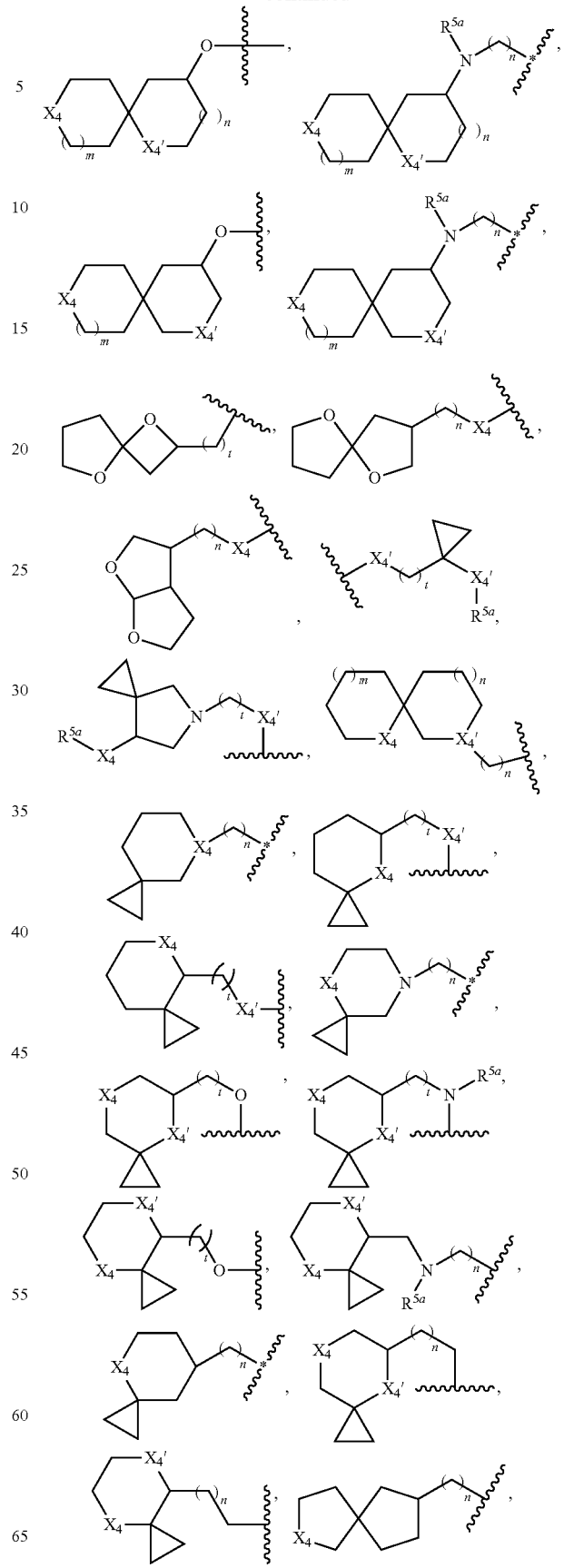

-continued
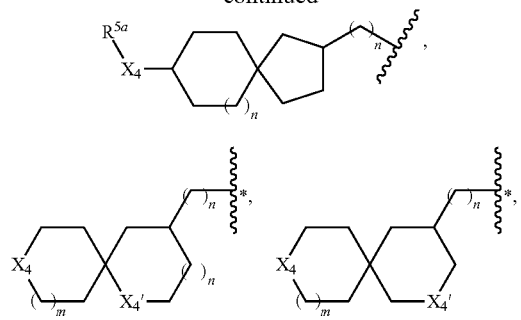
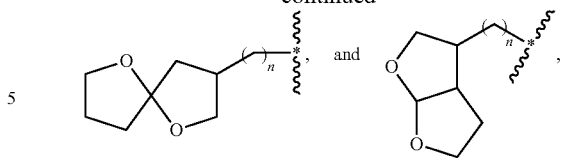 and
wherein each of $X_4$ and $X_4'$ is independently $(CR^4R^{4a})_m$, $NR^5$, O, S, S=O or $SO_2$;
each of m and n is independently 0, 1 or 2; and t is 1, 2, or 3.
In another embodiment, non-limiting examples of compounds disclosed herein, and their pharmaceutically acceptable salts and solvates thereof, are shown in the following:
(1)
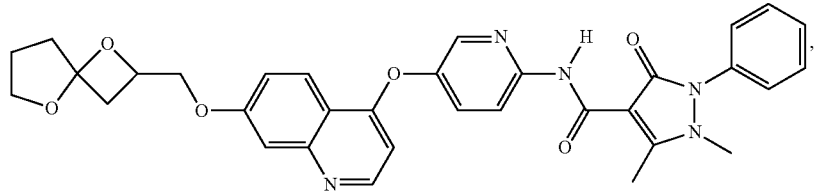
(2)
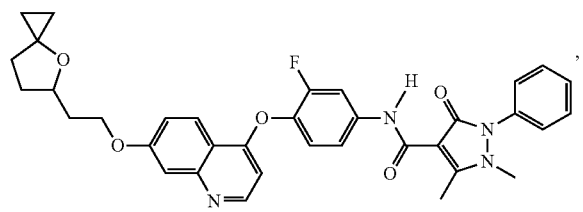
(3)
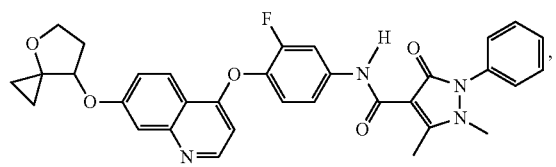
(4)
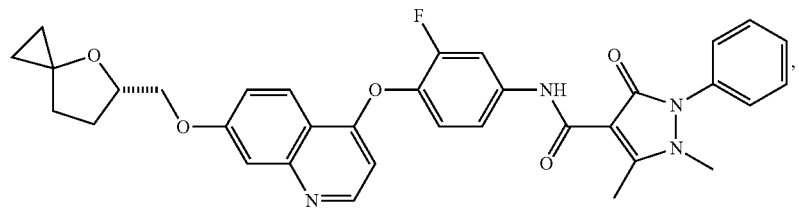
(5)
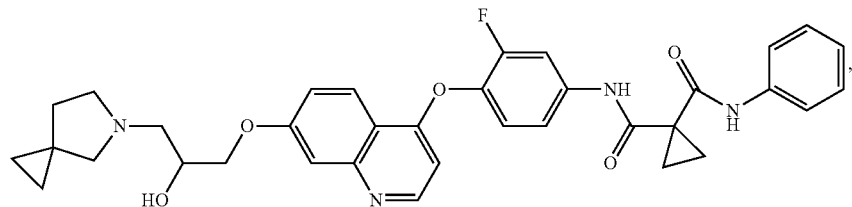
(6)
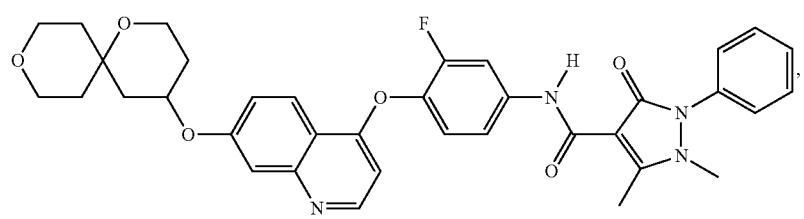

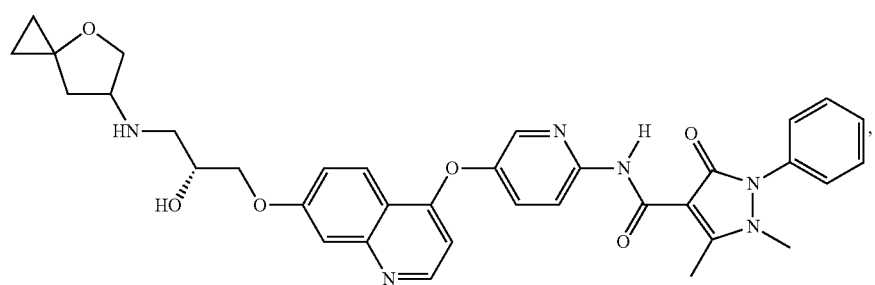
(7)
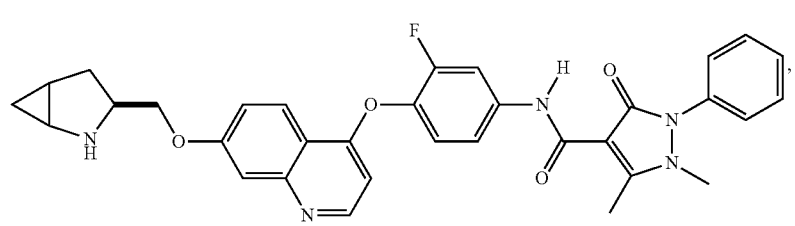
(8)
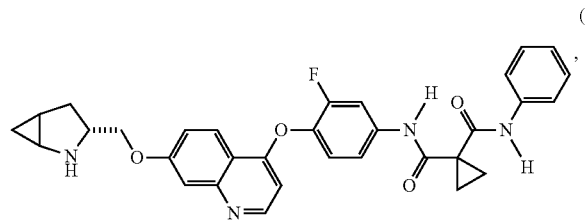
(9)
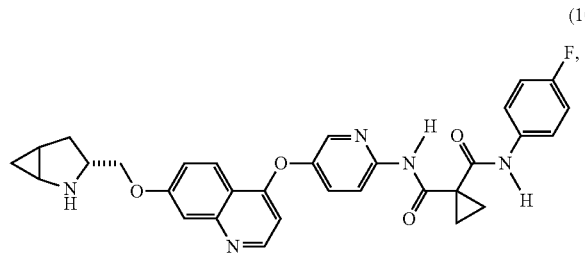
(10)
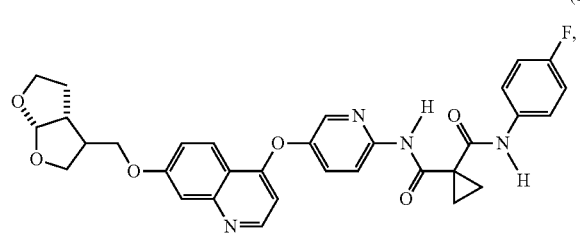
(11)
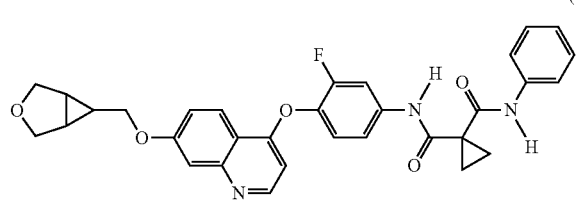
(12)
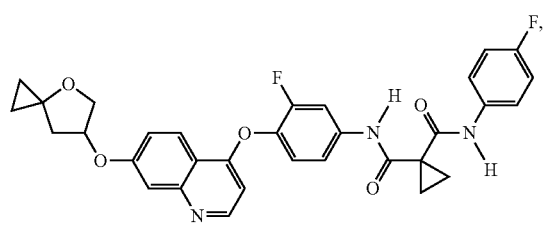
(13)
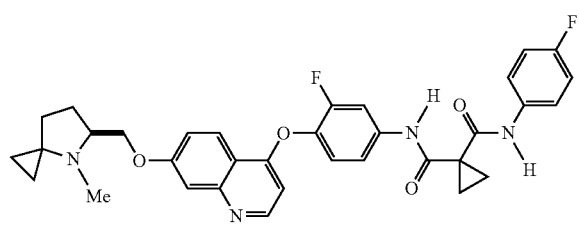
(14)
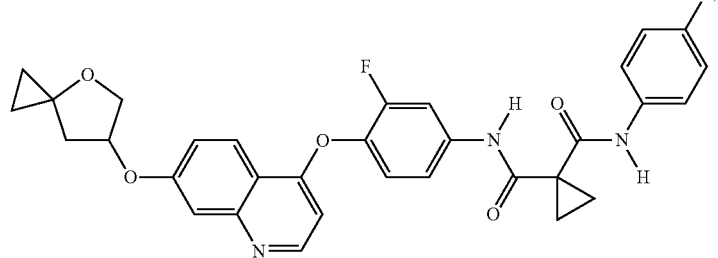
(15)

-continued
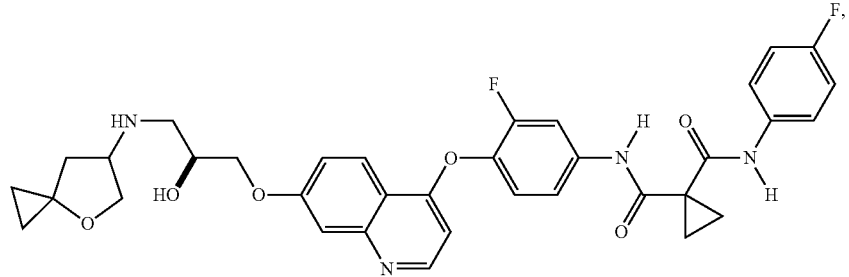
(16)
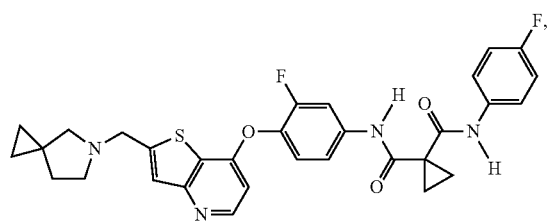
(17)
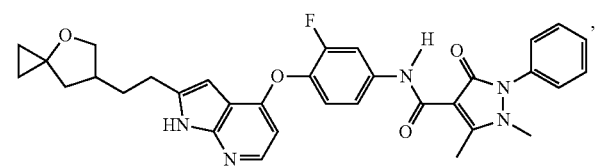
(18)
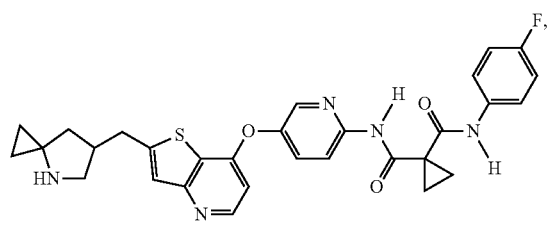
(19)
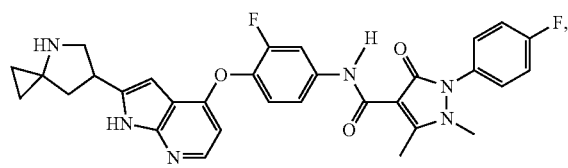
(20)
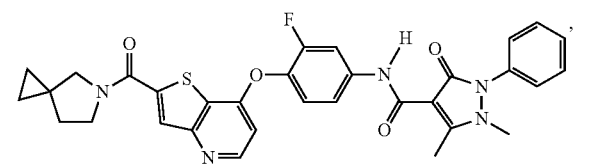
(21)
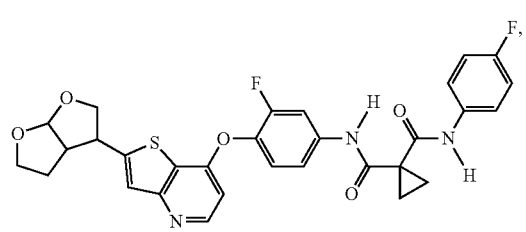
(22)
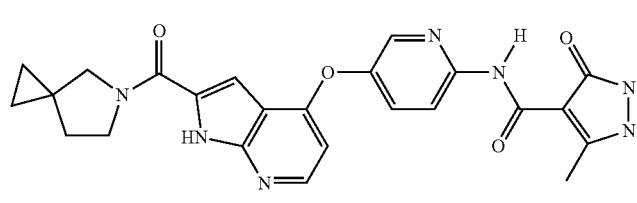
(23)
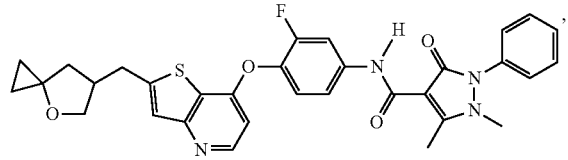
(24)
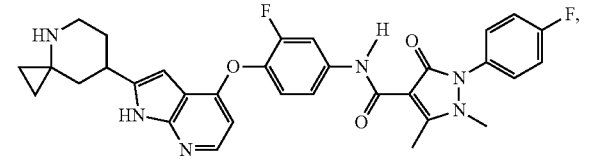
(25)

-continued
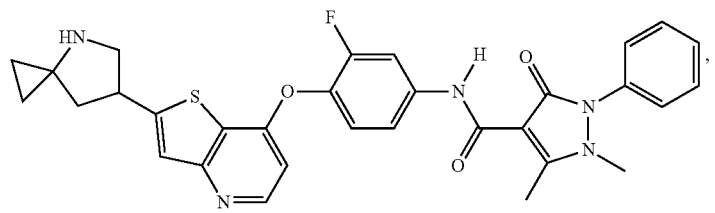
(28)
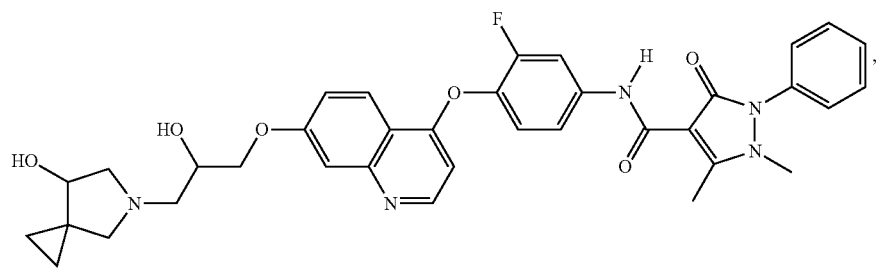
(29)
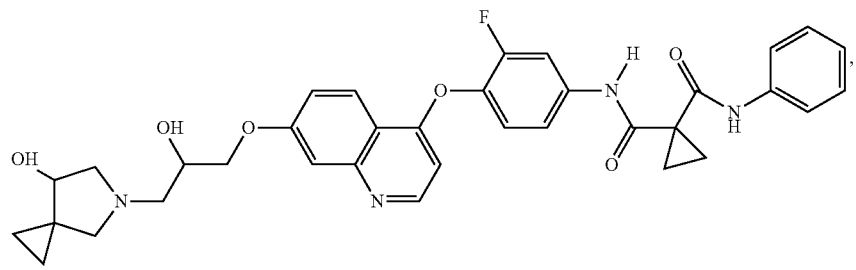
(30)
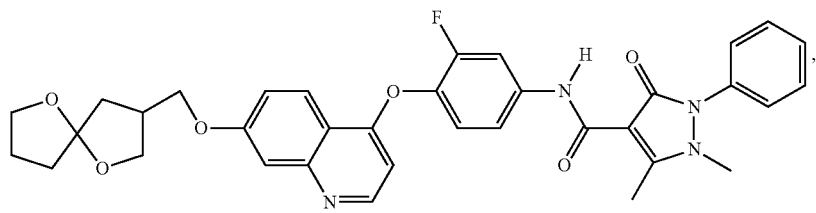
(31)
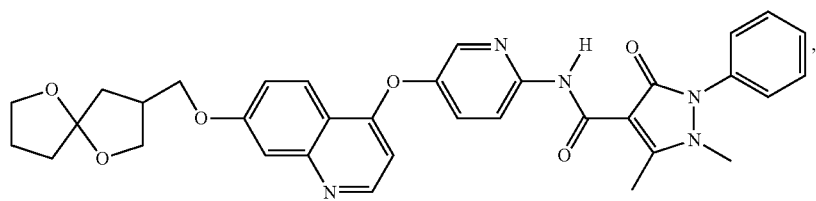
(32)
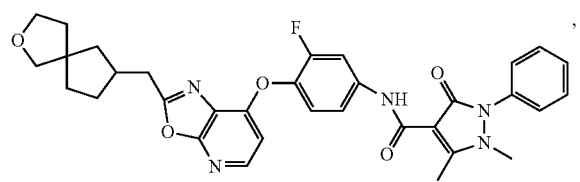
(33)
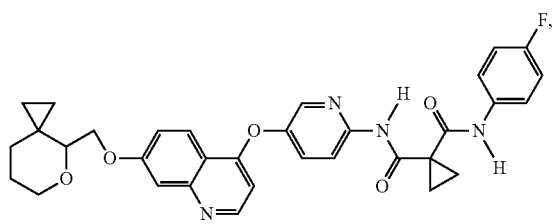
(34)
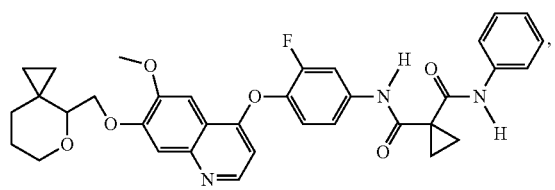
(35)
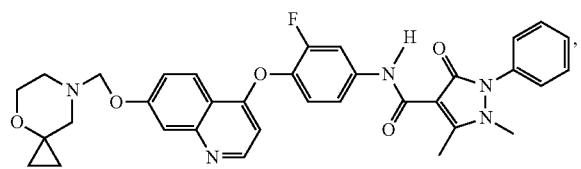
(36)

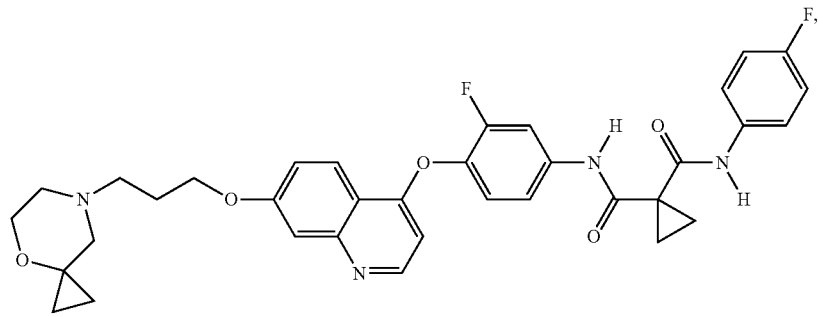
(37)
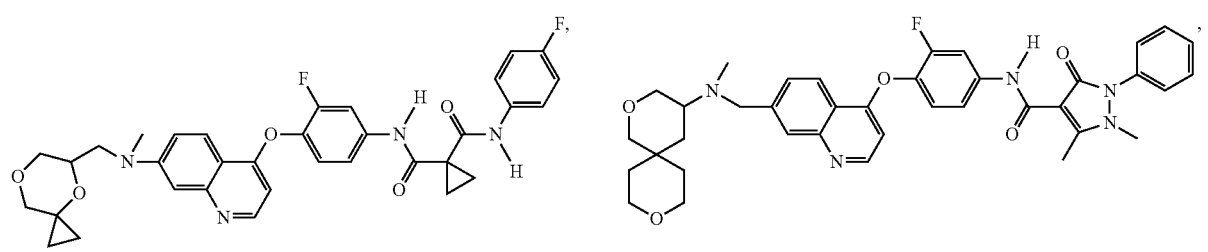
(38) (39)
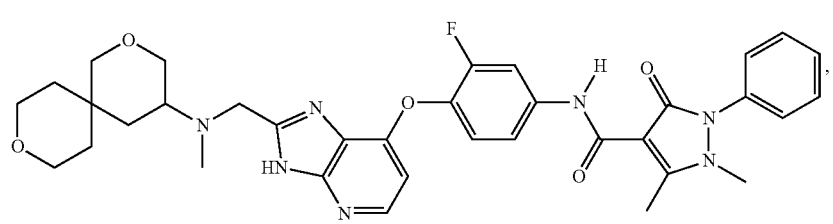
(40)
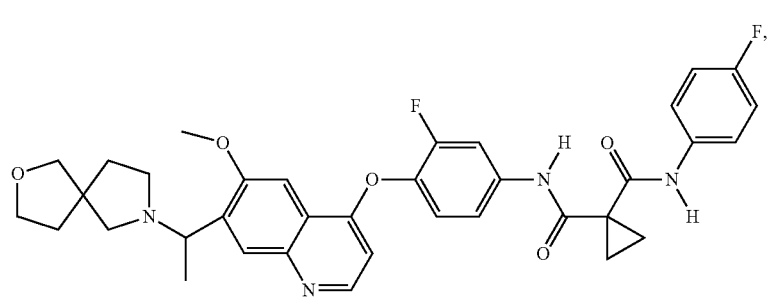
(41)
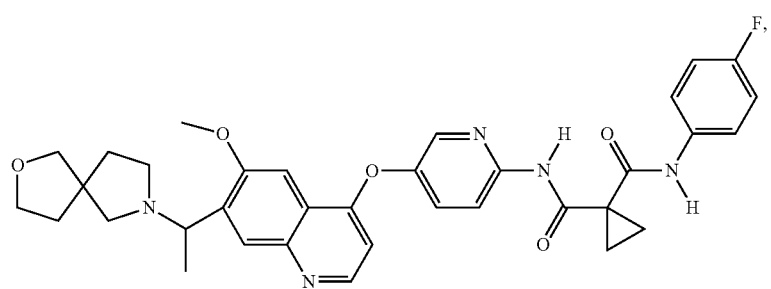
(42)
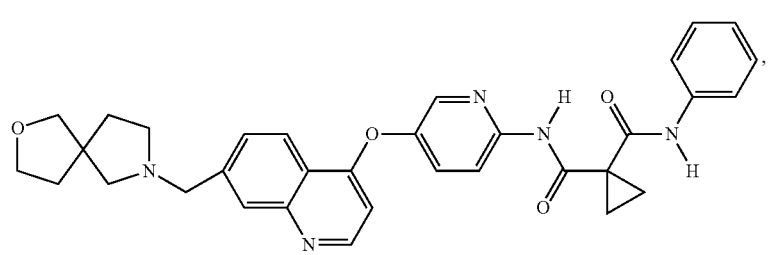
(43)

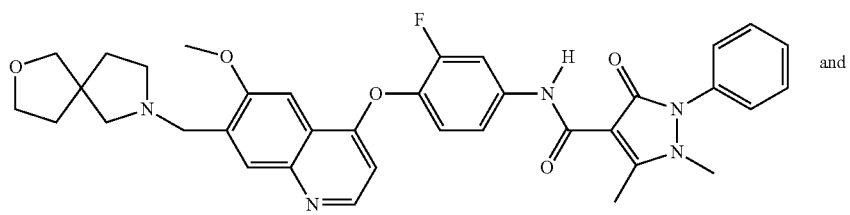

(44)

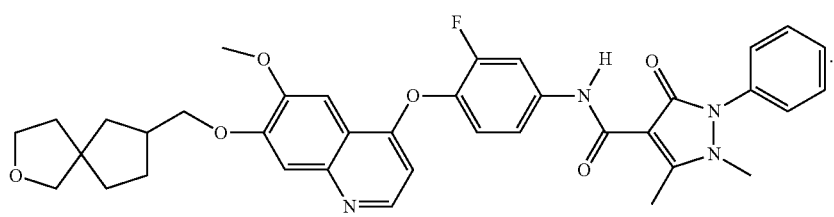

(45)

Provided herein includes the use of a compound disclosed herein, or a pharmaceutically acceptable salt thereof, in the manufacture of a medicament for the treatment either acutely or chronically of an angiogenesis mediated disease state, including those described herein. The compounds disclosed herein are useful in the manufacture of an anti-cancer medicament. The compounds disclosed herein are also useful in the manufacture of a medicament to attenuate, prevent, manage or treat disorders through inhibition of KDR, c-Met and/or IGF1R. Also provided herein is a pharmaceutical composition comprising a therapeutically effective amount of a compound of Formula (I), (IV) or (V) in association with at least one pharmaceutically acceptable carrier, adjuvant or diluent.

Also provided herein is a method of treating angiogenesis related disorders in a subject having or susceptible to such disorder, the method comprising treating the subject with a therapeutically effective amount of a compound of Formula (I), (IV) or (V).

Unless otherwise stated, all stereoisomers, geometric isomers, tautomers, solvates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The compounds disclosed herein also include salts of such compounds which are not necessarily pharmaceutically acceptable salts, and which may be useful as intermediates for preparing and/or purifying compounds of Formula (I), (IV) or (V) and/or for separating enantiomers of compounds of Formula (I), (IV) or (V).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

Composition, Formulations and Administration of Compounds of the Invention

According to another aspect, the invention features pharmaceutical compositions that include a compound of Formula (I), (IV) or (V), a compound listed herein, or a compound named in Examples 1-28, and a pharmaceutically acceptable carrier, adjuvant, or vehicle. The amount of the compound in the compositions disclosed herein is such that is effective to detectably inhibit a protein kinase in a biological sample or in a patient.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions disclosed herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. In some embodiments, the compositions are administered orally, intraperitoneally or intravenously. Sterile injectable forms of the compositions disclosed herein include aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that include water, Ringer's solution and isotonic sodium chloride solution. In addition, sterile, fixed oils are conventionally employed as a solvent or suspending medium.

For this purpose, any bland fixed oil includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions disclosed herein include orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions disclosed herein include administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The pharmaceutically acceptable compositions disclosed herein also include administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used. For topical applications, the pharmaceutically acceptable compositions may be formulated in a suitable ointment containing the active component suspended or dissolved in one or more carriers. Carriers for topical administration of the compounds disclosed herein include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, In other embodiments, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions disclosed herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a compound disclosed herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Some non-limiting examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds disclosed herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain pacifying agents and can also be of a composition that they release the active ingredient(s) only, or in other embodiments, in a certain part of the intestinal tract, optionally, in a delayed manner. Some non-limiting examples of embedding compositions that can be used include polymeric substances and waxes.

Dosage forms for topical or transdermal administration of a compound disclosed herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, contemplated herein is the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds disclosed herein are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds disclosed herein that may be combined with the carrier materials to produce a composition in a single dosage form will vary depending upon the host treated, the particular mode of administration. In other embodiments, the compositions should be formulated so that a dosage of between 0.01-300 mg/kg body weight/day of the inhibitor can be administered to a patient receiving these compositions.

Compounds disclosed herein can be administered as the sole pharmaceutical agent or in combination with one or more other additional therapeutic (pharmaceutical) agents where the combination causes no unacceptable adverse effects. This may be of particular relevance for the treatment of hyperproliferative diseases such as cancer. In this instance, the compound disclosed herein can be combined with known cytotoxic agents, signal transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" refers to include chemotherapeutic agents and other anti-proliferative agents.

For example, chemotherapeutic agents or other antiproliferative agents may be combined with the compounds disclosed herein to treat proliferative disease or cancer. Examples of chemotherapeutic agents or other antiproliferative agents include HDAC inhibitors including, but are not limited to, SAHA, MS-275, MGO 103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S. Pat. No. 6,268,137, U.S. Pat. No. 5,578,716, U.S. Pat. No. 5,919,772, U.S. Pat. No. 6,054,439, U.S. Pat. No. 6,184,211, U.S. Pat. No. 6,020,318, U.S. Pat. No. 6,066,625, U.S. Pat. No. 6,506,735, U.S. Pat. No. 6,221,849, U.S. Pat. No. 6,953,783, U.S. Ser. No. 11/393,380.

In another embodiment disclosed herein, for example, chemotherapeutic agents or other anti-proliferative agents may be combined with the compounds disclosed herein to treat proliferative diseases and cancer. Examples of known chemotherapeutic agents include, but are not limited to, for example, other therapies or anticancer agents that may be used in combination with the inventive anticancer agents disclosed herein and include surgery, radiotherapy (in but a few examples, gamma-radiation, neutron beam radiotherapy, electron beam radiotherapy, proton therapy, brachytherapy, and systemic radioactive isotopes, to name a few), endocrine therapy, taxanes (taxol, taxotere etc), platinum derivatives, biologic response modifiers (interferons, interleukins, and tumor necrosis factor (TNF), TRAIL receptor targeting, agents, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate, Pemetrexed etc), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), Cell cycle inhibitors (KSP mitotic kinesin inhibitors, CENP-E and CDK inhibitors), enzymes (Asparaginase), and hormones (Tamoxifen, Leuprolide, Flutamide, and Megestrol), GleeveC™, adriamycin, dexamethasone, and cyclophosphamide. Antiangiogenic agents (Avastin and others). Kinase inhibitors (Imatinib (Gleevec), Sutent, Nexavar, Erbitux, Herceptin, Tarceva, Iressa and others). Agents inhibiting or activating cancer pathways such as the mTOR, HIF (hypoxia induced factor) pathways and others. For a more comprehensive discussion of updated cancer therapies see, http://www.nci.nih.gov/, a list of the FDA approved oncology drugs at http://www.fda.gov/cder/cancer/druglist-rame.htm, and The Merck Manual, Eighteenth Ed. 2006, the entire contents of which are hereby incorporated by reference.

In another embodiment, the compounds disclosed herein can be combined with cytotoxic anti-cancer agents. Examples of such agents can be found in the 13th Edition of the Merck Index (2001). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, or vindesine.

Other cytotoxic drugs suitable for use with the compounds disclosed herein include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, or vinorelbine.

Other cytotoxic anti-cancer agents suitable for use in combination with the compounds disclosed herein also include newly discovered cytotoxic principles, some examples of cytotoxic principles include, but are not limited to, oxaliplatin, gemcitabine, capecitabine, epothilone and its natural or synthetic derivatives, temozolomide (Quinn et al., *J. Clin. Oncology,* 2003, 21(4), 646-651), tositumomab (Bexxar), trabedectin (Vidal et al., *Proceedings of the American Society for Clinical Oncology,* 2004, 23, abstract, 3181), and the inhibitors of the kinesin spindle protein Eg5 (Wood et al., *Curr. Opin. Pharmacol.* 2001, 1, 370-377).

In another embodiment, the compounds disclosed herein can be combined with other signal transduction inhibitors. Of particular interest are signal transduction inhibitors which target the EGFR family, such as EGFR, HER-2, and HER-4 (Raymond et al., *Drugs,* 2000, 60 (Suppl.1), 15-23; Harari et al., *Oncogene,* 2000, 19 (53), 6102-6114), and their respective ligands. Examples of such agents include, by no way of limitation, antibody therapies such as Herceptin (trastuzumab), Erbitux (cetuximab), Vectibix (panitumumab), and pertuzumab. Examples of such therapies also include, by no way of limitation, small-molecule kinase inhibitors such as Iressa (Gefitinib), Tarceva (Erlotinib), Tykerb (Lapatinib) Canertinib (CI1033), AEE788 (Traxler et al., Cancer Research, 2004, 64, 4931-4941).

In another embodiment, the compounds disclosed herein can be combined with other signal transduction inhibitors targeting receptor kinases of the split-kinase domain families (VEGFR, FGFR, PDGFR, flt-3, c-kit, c-fms, and the like), and their respective ligands. These agents include, by no way of limitation, antibodies such as Avastin (bevacizumab). These agents also include, by no way of limitation, small-molecule inhibitors such as Gleevec/Imanitib, Sprycel (Dasatinib), Tasigna (Nilotinib), Nexavar (Sorafenib), CHIR-265, Pazopanib (GW-786034), Recentin (Cediranib/AZD2171), Zactima (Vandetanib), Vatalanib (PTK787/ZK222584), Telatinib (BAY-579352), BMS-690514, BMS582664 (Brivanib), BMS540215, Axitinib (AG-013736). Motesanib (AMG706), Sutent (Sunitinib), ZD6474 (Hennequin et al., *92nd AACR Meeting*, New Orleans, Mar. 24-28, 2001, abstract, 3152), Tivozanib (KRN-951) (Taguchi et al., *95th AACR Meeting*, Orlando, Fla., 2004, abstract, 2575), CP-547, 632 (Beebe et al., *Cancer Res.* 2003, 63, 7301-7309), CP-673, 451 (Roberts et al., *Proceedings of the American Association of Cancer Research,* 2004, 45, abstract, 3989), CHIR-258 (Lee et al., *Proceedings of the American Association of Cancer Research,* 2004, 45, abstract, 2130), MLN-518 (Shen et al., *Blood,* 2003, 102, 11, abstract, 476).

In another embodiment, the compounds disclosed herein can be combined with inhibitors of histone deacetylase. Examples of such agents include, by no way of limitation, suberoylanilide hydroxamic acid (SAHA), LAQ-824 (Ottmann et al., *Proceedings of the American Society for Clinical Oncology,* 2004, 23, abstract, 3024), LBH-589 (Beck et al., *Proceedings of the American Society for Clinical Oncology,* 2004, 23, abstract, 3025), MS-275 (Ryan et al., *Proceedings of the American Association of Cancer Research,* 2004, 45, abstract, 2452), FR-901228 (Piekarz et al., *Proceedings of the American Society for Clinical Oncology,* 2004, 23, abstract, 3028) and MGCDO103 (U.S. Pat. No. 6,897,220).

In another embodiment, the compounds disclosed herein can be combined with other anti-cancer agents such as proteasome inhibitors, and m-TOR inhibitors. These include, by no way of limitation, bortezomib (Mackay et al., *Proceedings of the American Society for Clinical Oncology,* 2004, 23, Abstract, 3109), and sirolimus (rapamycin), everolimus, temsirolimus (CCI-779) (Wu et al., *Proceedings of the American Association of Cancer Research,* 2004, 45, abstract, 3849). The compounds disclosed herein can be combined with other anti-cancer agents such as topoisomerase inhibitors, including but not limited to camptothecin.

Those additional agents may be administered separately from the compound-containing composition, as part of a multiple dosage regimen. Alternatively, those agents may be part of a single dosage form, mixed together with the compound disclosed herein in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions disclosed herein will be no more than the amount that would normally be administered in a composition comprising that therapeutic agent as the only active agent. In other embodiment, the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound disclosed herein may act synergistically.

Uses of the Compounds and Compositions of the Invention

The invention features pharmaceutical compositions that include a compound of Formula (I) or a compound listed herein, and a pharmaceutically acceptable carrier, adjuvant, or vehicle. The amount of compound in the compositions disclosed herein is such that is effective to detectably inhibit a protein kinase, such as VEGFR/KDR, IGF/IGF1R and/or c-Met inhibitory activity. The compounds disclosed herein are useful in therapy as antineoplasia agents or to minimize deleterious effects of VEGF, IGF and/or HGF.

Compounds disclosed herein would be useful for, but not limited to, the prevention or treatment of proliferative diseases, conditions, or disorders in a patient by administering to the patient a compound or a composition disclosed herein in an effective amount. Such diseases, conditions, or disorders include cancer, particularly metastatic cancer, atherosclerosis, and lung fibrosis.

Compounds disclosed herein would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds disclosed herein are also useful in the treatment of diabetic conditions such as diabetic retinopathy and microangiopathy. The compounds disclosed herein are also useful in the reduction of blood flow in a tumor in a subject. The compounds disclosed herein are also useful in the reduction of metastasis of a tumor in a subject.

Besides being useful for human treatment, these compounds are also useful for veterinary treatment of companion animals, exotic animals and farm animals, including mammals, rodents, and the like. In other embodiments, animals include horses, dogs, and cats. As used herein, the compounds disclosed herein include the pharmaceutically acceptable derivatives thereof.

Where the plural form is used for compounds, salts, and the like, this is taken to refer to also a single compound, salt, and the like.

The treatment method that includes administering a compound or composition disclosed herein can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition disclosed herein as a single dosage form or separately from the compound or composition as part of a multiple dosage form. The additional therapeutic agent may be administered at the same time as a compound disclosed herein or at a different time. In the latter case, administration may be staggered by, for example, 6 hours, 12 hours, 1 day, 2 days, 3 days, 1 week, 2 weeks, 3 weeks, 1 month, or 2 months.

The invention also features a method of inhibiting the growth of a cell that expresses VEGFR, IGF1R or c-Met, that includes contacting the cell with a compound or composition disclosed herein, thereby causing inhibition of growth of the cell. Examples of a cell whose growth can be inhibited include: a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, or a leukemia cell.

Provided herein a method of inhibiting VEGFR, IGF1R or c-Met kinase activity in a biological sample that includes contacting the biological sample with a compound or composition disclosed herein. The term "biological sample" as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly VEGFR, IGF1R or c-Met kinase activity, in a biological sample is useful for a variety of purposes known to one of skill in the art. Examples of such purposes include, but are not limited to, blood transfusion, organ-transplantation, biological specimen storage, and biological assays.

In certain embodiments disclosed herein, an "effective amount" or "effective dose" of the compound or pharmaceutically acceptable composition is that amount effective for treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

The compounds disclosed herein or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound disclosed herein.

Suitable coatings and the general preparation of coated implantable devices are described in U.S. Pat. Nos. 6,099, 562, 5,886,026, and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics into the composition. Implantable devices coated with a compound disclosed herein are another embodiment disclosed herein. The compounds may also be coated on implantable medical devices, such as beads, or co-formulated with a polymer or other molecule, to provide a "drug depot" thus permitting the drug to be released over a longer time period than administration of an aqueous solution of the drug.

General Synthetic Procedures

Generally, the compounds disclosed herein may be prepared by methods described herein, wherein the substituents are as defined for formulas (I), (IV) or (V), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium Anhydrous $CH_2Cl_2$ and $CHCl_3$ were obtained by refluxing the solvent with $CaH_2$. EtOAc, PE, hexane, DMA and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1H$ NMR spectra were recorded with a Bruker 400 MHz spectrometer at ambient temperature. $^1H$ NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were determined on an Agilent 1200 Series LCMS (Zorbax SB-C18, 2.1×30 mm, 4 micorn, 10 min, 0.6 mL/min flow rate, 5 to 95% (0.1% formic acid in $CH_3CN$) in (0.1% formic acid in $H_2O$) with UV detection at 210/254 nm and a low resonance electrospray mode (ESI).

Purities of compounds were assessed by Agilent 1100 Series high performance liquid chromatography (HPLC) with UV detection at 210 nm and 254 nm (Zorbax SB-C18, 2.1×30 mm, 4 micorn, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
HOAc acetic acid
MeCN, $CH_3CN$ acetonitrile
$NH_3$ ammonia
$NH_4Cl$ ammonium chloride
HBTU O-benzotriazol-1-yl-N,N,N',N'-tetramethyluronium hexafluorophosphate
HATU O-(7-azabenzotriazol-1-yl)-N,N,N',N'-tetramethyluronium hexafluorophosphate
PyBop benzotriazol-1-yl-oxy-tripyrrolidino-phosphonium hexafluorophosphate
$Pd_2(dba)_3$ bis(dibenzylideneacetone) palladium
BINAP 2,2'-bis(diphenylphosphino)-1,1'-binaphthyl
TEAC bis(tetra-ethylammonium)carbonate
$BBr_3$ boron tribromide
BSA bovine serum albumin
$Br_2$ bromine
BOC, Boc tert-butyloxycarbonyl
$Cs_2CO_3$ cesium carbonate
$CHCl_3$ chloroform
$CDCl_3$ chloroform deuterated
Cu copper
CuI copper(I) iodide
$Et_2O$ diethyl ether
DBU 1,8-diazabicyclo[5,4,0]undec-7-ene
DIBAL diisobutylaluminum hydride
DIAD diisopropyl azodicarboxylate
DIEA diisopropylethylamine
DEAD dimethyl azodicarboxylate
DMF dimethylformamide
DMAP 4-dimethylaminopyridine
DMSO dimethylsulfoxide
EDC, EDCI 1-(3-dimethylaminopropyl)-3-ethylcarbodiimide hydrochloride dppa diphenylphosphoryl azide
EtOAc ethyl acetate
FBS fetal bovine serum g gram h hour
HBr hydrobromic acid
HCl hydrochloric acid
HOBt 1-hydroxybenzotriazole hydrate
$H_2$ hydrogen
$H_2O_2$ hydrogen peroxide
Fe iron
LiHMDS lithium bis(trimethylsilyl)-amide
LDA lithium diisopropylamide
MCPBA meta-chloroperbenzoic acid
$MgSO_4$ magnesium sulfate
MeOH, $CH_3OH$ methanol
MeI methyl iodide
$CH_2Cl_2$, DCM methylene chloride
NMP N-methylpyrrolidinone
mL, ml milliliter
$N_2$ nitrogen
Pd/C palladium on carbon
$Pd(OAc)_2$ palladium acetate
$Pd(OH)_2$ palladium hydroxide
$Pd(PPh_3)_4$ palladium tetrakis triphenylphosphine
$Pd(dppf)Cl_2$ 1,1-bis(diphenylphosphino)ferrocene palladium chloride
PE petroleum ether (60-90° C.)
PBS phosphate buffered saline
$POCl_3$ phosphorous oxychloride
$K_2CO_3$ potassium carbonate
KOH potassium hydroxide
RT, rt room temperature
Rt retention time
$NaHCO_3$ sodium bicarbonate
$NaBH_4$ sodium borohydride
$NaBH_3CN$ sodium cyanoborohydride
NaOtBu sodium tert-butoxide
NaOH sodium hydroxide
$NaClO_2$ sodium chlorite
NaCl sodium chloride
$NaH_2PO_4$ sodium dihydric phosphate
NaH sodium hydride
NaI sodium iodide
$Na_2SO_4$ sodium sulfate
TBTU O-benzotriazol-1-yl-N,N,N',N'-tetramethyluronium tetrafluoroborate
THF tetrahydrofuran
$Et_3N$, TEA triethylamine
TFA trifluoroacetic acid
$P(t-bu)_3$ tri(tert-butyl)phosphine
NBS N-bromosuccinimide
TBAI Tetrabutylammonium iodide
H2O water Scheme 1

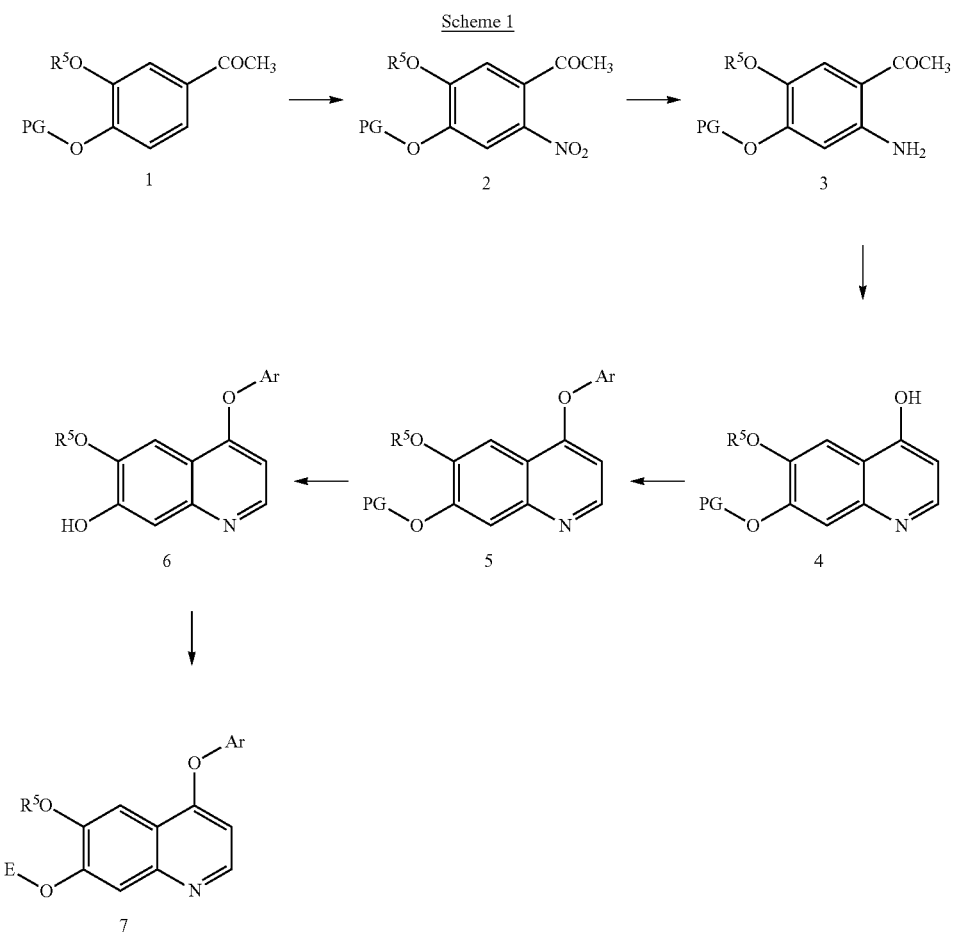

Substituted compounds 7, where $W_1$, $W_2$, $W_3$ and $W_4$ are CH, $X_1$ is O; $R^1$ (i.e. EO—), $R^5$, and PG are as defined above, can be prepared by the process illustrated in Scheme 1. The substituted aryl 1 is nitrated to give compound 2 by a suitable nitration reagent such as $HNO_3$ at appropriate temperature such as 0° C. The $NO_2$ group is then reduced by a reducing reagent such as Fe or Zn powder, or under hydrogenation condition in the presence of Pd catalyst such as Pd/C. Aniline 3 is condensed with a formate such as ethyl formate under basic condition to give substituted quinoline 4. Coupling of 4 with appropriate aryl derivatives yields substituted diaryl ethers 5. The protecting group PG is removed to provide compound 6, which is condensed with E-L (L=a suitable leaving group such as OMs, Cl, Br or I; E=aliphatic, heterocyclic aliphatic, fused heterobicyclic aliphatic, spiro heterobicyclic aliphatic, cyclic aliphatic, fused bicyclic aliphatic, spiro bicyclic aliphatic, heterocyclic, fused heterobicyclic, spiro heterobicyclic, cyclic, fused bicyclic, spiro bicyclic, etc.) to afford desired kinase inhibitor 7.

Scheme 2

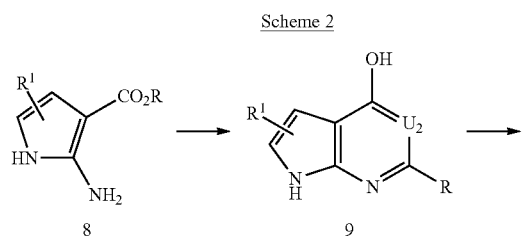

-continued

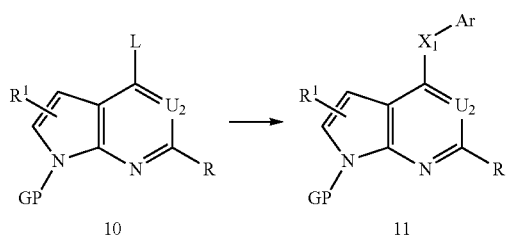

Alternatively, substituted indole/azaindole analogs 11 can be synthesized through the procedure depicted in Scheme 2. Where $R^1$, $X_1$, $U_2$ and PG are as defined above, R is H, $R^{5a}R^5N$—, aliphatic, alkoxy, haloalkyl, heterocyclyl, heterocyclylalkyl, cycloalkyl, cycloalkylalkyl, cycloalkylalkoxy or heterocyclylalkoxy. Substituted 2-aminopyrazole 8 is first transformed to 9 in a similar fashion as described in Scheme 1. The OH group is then replaced with a good leaving group L, such as Cl, F or OMs. L in compound 10 is converted to a kinase inhibitor 11 in the presence of base such as $Cs_2CO_3$, NaOH, DMAP, or lutidine in a solvent such as dioxane, toluene, or DMA, etc. preferably at elevated temperature.

Scheme 3

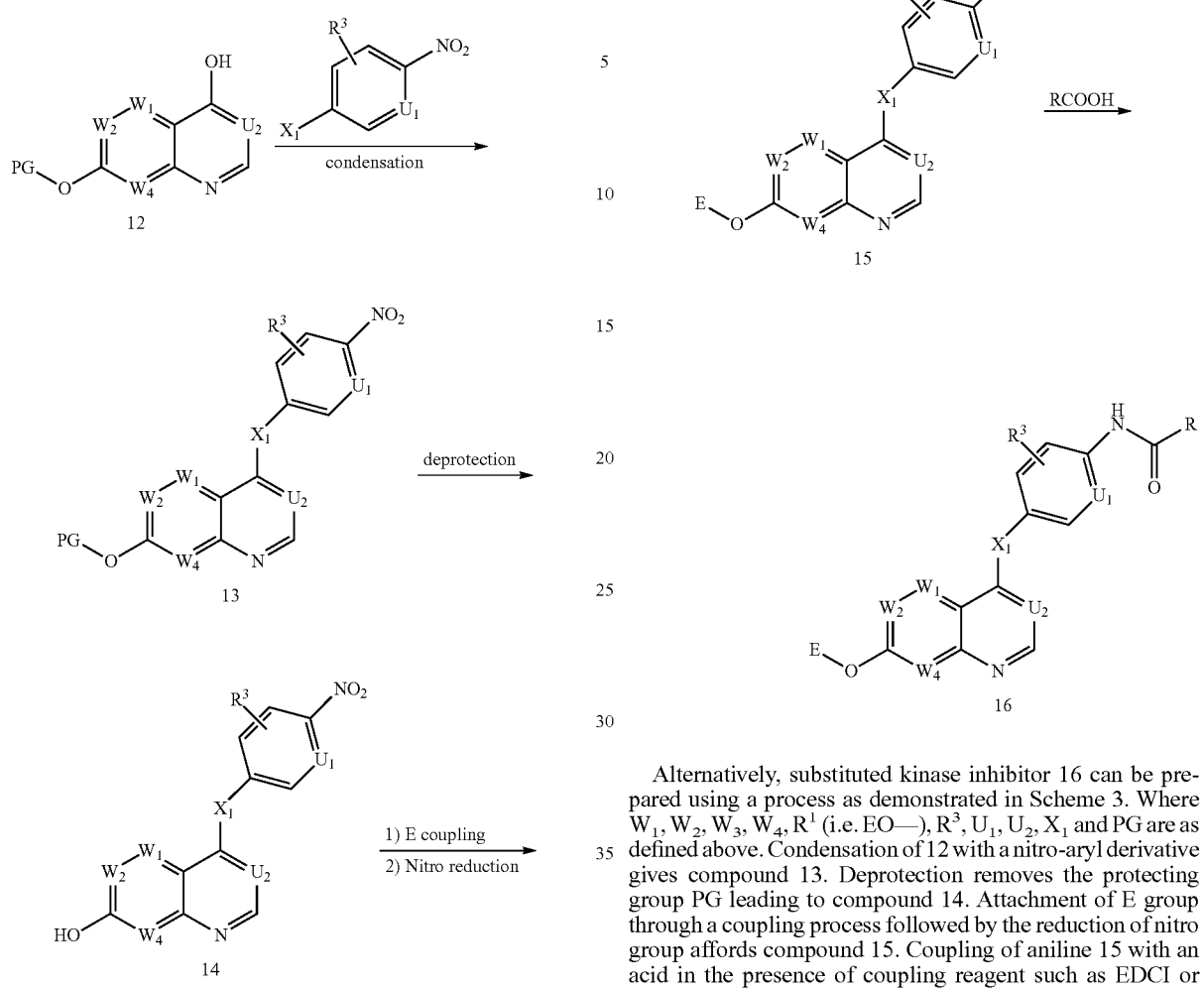

Alternatively, substituted kinase inhibitor 16 can be prepared using a process as demonstrated in Scheme 3. Where $W_1, W_2, W_3, W_4, R^1$ (i.e. EO—), $R^3, U_1, U_2, X_1$ and PG are as defined above. Condensation of 12 with a nitro-aryl derivative gives compound 13. Deprotection removes the protecting group PG leading to compound 14. Attachment of E group through a coupling process followed by the reduction of nitro group affords compound 15. Coupling of aniline 15 with an acid in the presence of coupling reagent such as EDCI or HATU furnishes desired kinase inhibitor 16.

Scheme 4

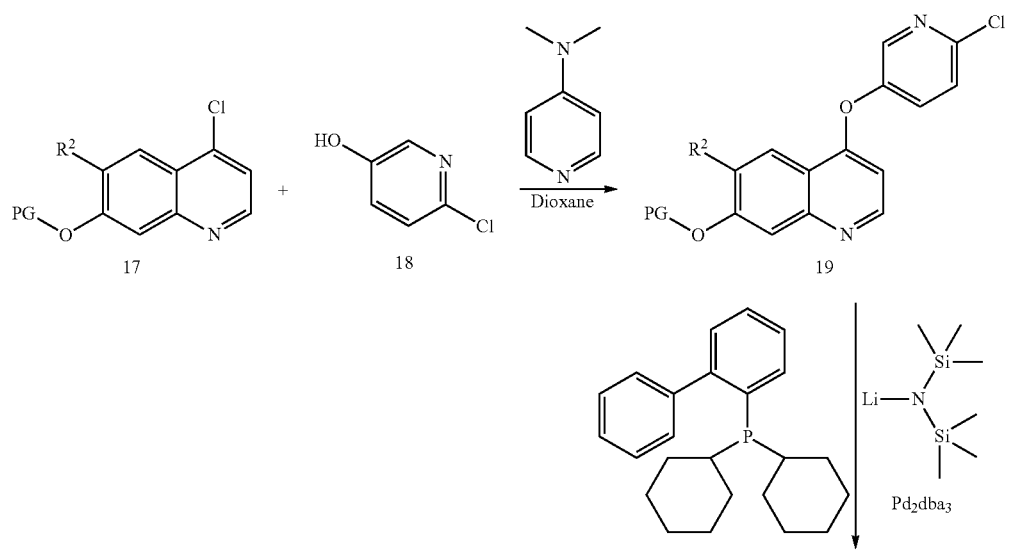

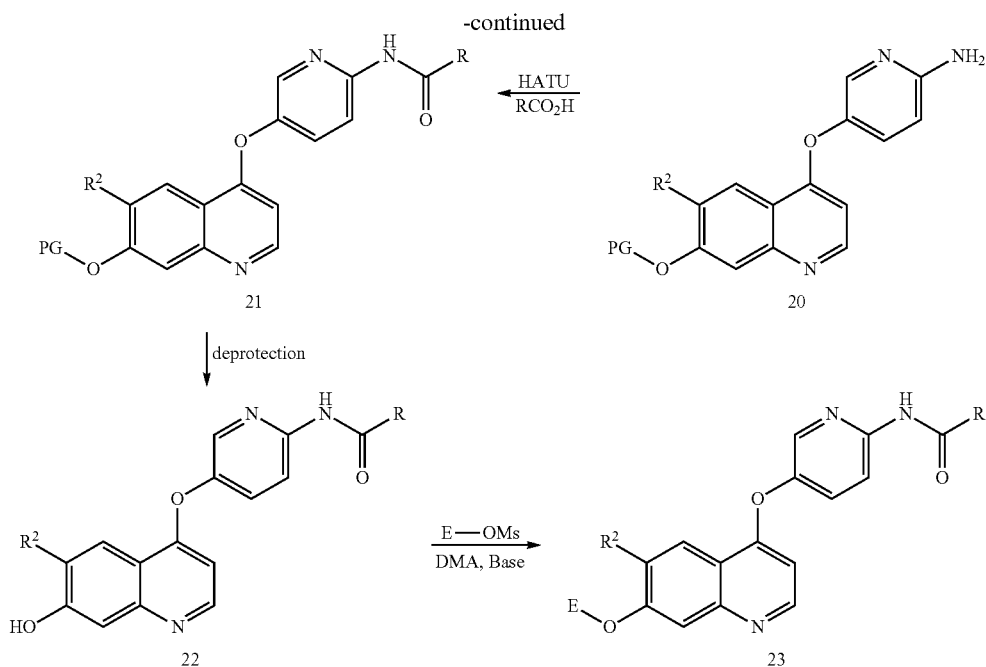

Alternatively, kinase inhibitors in this invention can be obtained through the process as described in Scheme 4. Where $R^1$ (i.e. EO—), $R^2$ and PG are as defined above. Thus, compound 20 is prepared through Pd catalyzed amination of 2-chloropyridine derivative 19. Coupling of aniline 20 with an acid followed by the removal of protecting group PG gives compound 22. An appropriate group such as spiro or bicyclic moiety is appended to the quinoline portion to yield compound 23. In the above structures, R is structures defined by $V_1$, $V_2$, $V_3$, and $V_4$ in Formula (IIa), or structures defined by $Z_1$, $Z_2$, $X_2$, and $X_3$ in Formula (IIb).

EXAMPLES

Example 1

N-(4-(7-(((5S)-4-methyl-4-azaspiro[2.4]heptane-5-yl)methoxy)quinolin-4-yloxy)-3-fluorophenyl)-2,3-dihydro-1,5-dimethyl-3-oxo-2-phenyl-1H-pyrazole-4-carboxamide

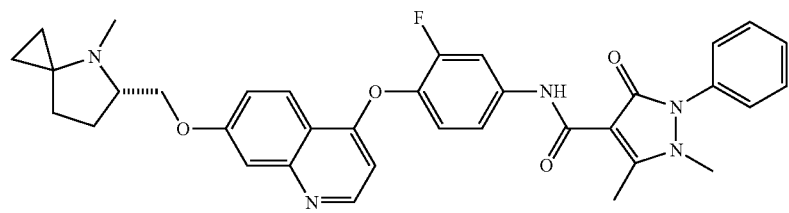

Step 1) (S)-5-((tetrahydro-2H-pyran-2-yloxy)methyl)pyrrolidin-2-one

To a mixture of (S)-5-(hydroxymethyl)pyrrolidin-2-one (1.0 g, 8.7 mmol, Aldrich) and DHP (1.46 g, 17.4 mmol, Alfa) in 20 mL of dichloromethane was added PPTS (0.437 g, 1.74 mmol, Aldrich) in portions. The reaction mixture was stirred at rt for 4 hrs, and was quenched with 20 mL of saturated NaHCO$_3$ aqueous solution. The resulted mixture was extracted with dichloromethane (25 mL×2). The combined organic phases were dried over Na$_2$SO$_4$ and concentrated in vacuo. The residue was purified by a silica gel column chromatography (EtOAc) to give the title compound (as a diastereomer mixture) as colorless oil (0.9 g, 52%).

MS (ESI, pos. ion) m/z: 199.9 (M+1);

$^1$H NMR (400 MHz, CDCl$_3$): δ 1.69-1.88 (m, 6H), 2.25-2.28 (m, 2H), 2.32-2.35 (m, 2H), 3.23 (m, 1H), 3.48-3.55 (m, 2H), 3.78-3.85 (m, 2H), 4.58 (m, 1H).

Step 2) (S)-1-methyl-5-((tetrahydro-2H-pyran-2-yloxy)methyl)pyrrolidin-2-one

To a mixture of NaH (0.48 g, 12 mmol, 60% mineral oil, Aldrich) in 15 mL of DMF was added a solution of (S)-5-((tetrahydro-2H-pyran-2-yloxy)methyl)pyrrolidin-2-one (2 g, 10 mmol) in 5 mL of DMF via a syringe at −40° C. The reaction was stirred at −40° C. for 1 hr. CH$_3$I (0.9 mL, 12 mmol, Shanghai Jingchun Reagent Ltd.) was added dropwise via a syringe. The reaction was continued to stir at −40° C. for 4 hrs, and was quenched with 10 mL of saturated NaHSO$_3$ aqueous solution. The mixture was extracted with ethyl acetate (50 mL×3). The combined organic phases were dried over Na$_2$SO$_4$ and concentrated in vacuo. The residue was purified by a silica gel column chromatography (EtOAc) to give the desired product as colorless oil (1.98 g, 92%).

MS (ESI, pos. ion) m/z: 214.0 (M+1);
¹H NMR (400 MHz, CDCl₃): δ 1.69-1.88 (m, 6H), 1.93-2.17 (m, 2H), 2.33-2.47 (m, 2H), 2.90 (3H, s), 3.40-3.52 (m, 2H), 3.80-3.90 (m, 2H), 3.78 (m, 1H), 4.60 (m, 1H).

Step 3) (5S)-4-methyl-5-((tetrahydro-2H-pyran-2-yloxy)methyl)-4-azaspiro[2.4]heptane To a mixture of (S)-1-methyl-5-((tetrahydro-2H-pyran-2-yloxy)methyl)-pyrrolidin-2-one (0.6 g, 2.82 mmol) in 20 mL of THF was added Ti(Oi-Pr)₄ (2.56 mL, 8.45 mmol, d=0.937 g/L, Aldrich) via a syringe under nitrogen at rt. After stirring at rt for 30 min, EtMgBr (5.63 mL, 16.9 mmol, 3M ether solution, Aldrich) was added via a syringe pump over 3 hrs. The reaction was continued to stir at rt overnight, and then quenched with a mixture of 20 mL of water and 30 mL of ethyl acetate. After stirring for 20 min, the mixture was filtered through a celite pad. The filtrate was extracted with ethyl acetate (30 mL×3). The combined organic phases were dried over Na₂SO₄ and concentrated in vacuo. The residue was purified by a silica gel column chromatography (50:1(v/v) CH₂Cl₂/CH₃OH) to afford (5S)-4-methyl-5-((tetrahydro-2H-pyran-2-yloxy)methyl)-4-azaspiro[2.4]heptane as pale yellow oil (64 mg, 10%).

MS (ESI, pos. ion) m/z: 226.0 (M+1);
¹H NMR (400 MHz, CDCl₃): δ0.23 (m, 1H), 0.46 (m, 1H), 0.63 (m, 1H), 0.86 (m, 1H), 1.58-1.90 (m, 10H), 2.13 (s, 3H), 2.85 (m, 1H), 3.37-3.50 (m, 2H), 3.72-3.89 (m, 2H), 4.62 (m, 1H).

Step 4) (5S)-4-methyl-5-(hydroxymethyl)-4-azaspiro[2.4]heptane

To a mixture of (5S)-4-methyl-5-((tetrahydro-2H-pyran-2-yloxy)methyl)-4-azaspiro[2.4]heptane (64 mg, 0.284 mmol) in 10 mL of methanol was added 4-methyl-benzenesulfonic acid (97.8 mg, 0.568 mmol, Aldrich). The reaction mixture was stirred at 50° C. overnight, and then concentrated in vacuo. The residue was treated with 10 mL of saturated Na₂CO₃ aqueous solution, and extracted with dichloromethane (20 mL×3). The combined organic phases were dried over Na₂SO₄ and concentrated in vacuo to give the desired product as yellow oil (32 mg, 80%).

MS (ESI, pos. ion) m/z: 142.0 (M+1).

Step 5) ((5S)-4-methyl-4-azaspiro[2.4]heptane-5-yl)methyl methanesulfonate

A mixture of (5S)-4-methyl-5-(hydroxymethyl)-4-azaspiro[2.4]heptane (0.2 g, 1.42 mmol) and triethylamine (0.287 g, 2.84 mmol, Shantou Xilong chemical factory) in 5 mL of dichloromethane was stirred at 0° C. for 30 min. To the mixture was added methanesulfonyl chloride (0.325 g, 2.84 mmol, Shanghai Haiqu chemical. Ltd.) via a syringe. The reaction mixture was stirred at 0° C. for 4 hrs and quenched with a mixture of 5 mL of saturated Na₂CO₃ aqueous solution and 5 mL of water. The resulted mixture was extracted with dichloromethane (20 mL×3). The combined organic phases were dried over Na₂SO₄ and concentrated in vacuo to give ((5S)-4-methyl-4-azaspiro[2.4]heptane-5-yl)methyl methanesulfonate as yellow oil (150 mg, 48%).

Step 6) N-(4-(7-(((5S)-4-methyl-4-azaspiro[2.4]heptane-5-yl)methoxy)quinolin-4-yloxy)-3-fluorophenyl)-2,3-dihydro-1,5-dimethyl-3-oxo-2-phenyl-1H-pyrazole-4-carboxamide

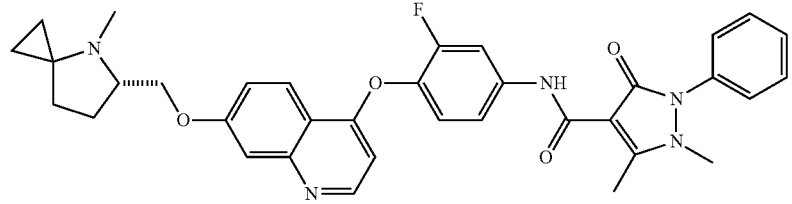 [SMILES: Cc1c(C(=O)Nc2ccc(Oc3ccnc4cc(OC[C@@H]5CCC6(CC6)N5C)ccc34)c(F)c2)c(=O)n(-c2ccccc2)n1C]

To a mixture of ((5S)-4-methyl-4-azaspiro[2.4]heptane-5-yl)methyl methanesulfonate (150 mg, 0.685 mmol) and N-(4-(7-hydroxyquinolin-4-yloxy)-3-fluorophenyl)-2,3-dihydro-1,5-dimethyl-3-oxo-2-phenyl-1H-pyrazole-4-carboxamide (331.5 mg, 0.685 mmol) in 8 mL of N,N-dimethylacetamide was added cesium carbonate (893 mg, 2.74 mmol, Aladdin). After stirring at 40° C. for 3 days, the reaction mixture was concentrated in vacuo and the residue was chromatographed with a silica gel column (50:1 (v/v) CH₂Cl₂/CH₃OH) to give the desired product as a pale yellow solid (25 mg, 6%).

MS (ESI, pos. ion) m/z: 304.5 [(M/2)+1]; LC-MS Rt: 3.402 min;
¹H NMR (400 MHz, CDCl₃): δ0.32 (m, 1H), 0.52 (m, 1H), 0.71 (m, 1H), 0.92 (m, 1H), 1.52 (m, 2H), 1.85 (m, 2H), 3.19 (m, 1H), 2.26 (s, 3H), 2.80 (s, 3H), 3.37 (s, 3H), 4.11 (m, 1H), 4.22 (m, 1H), 6.40 (d, J=5.2 Hz, 1H), 7.16 (t, J=8.4 Hz, 1H), 7.30 (m, 1H), 7.36 (m, 2H), 7.41 (m, 1H), 7.48 (m, 2H), 7.56 (m, 2H), 7.91 (dd, J=12 Hz, 1H), 8.26 (d, J=9 Hz, 1H), 8.58 (d, J=5 Hz, 1H), 10.88 (s, 1H).

Example 2

N-(4-(7-(((5R)-4-oxaspiro[2.4]heptane-5-yl)methoxyl)quinolin-4-yloxy)-3-fluorophenyl)-2,3-dihydro-1,5-dimethyl-3-oxo-2-phenyl-1H-pyrazole-4-carboxamide

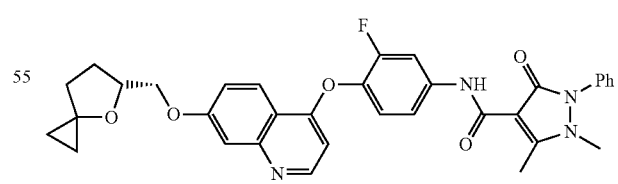

Step 1) (S)-tetrahydro-5-oxofuran-2-carboxylic acid

To a solution of L-glutamic acid (10.07 g, 0.068 mol, J&K CHEMICA) in 20 ml of concd. HCl and 40 mL H₂O was added a solution of NaNO₂(7.0 g, 0.102 mol, Shantou Xilong chemical factory) in H₂O (20 mL) slowly at -5° C. The mixture was continued to stir for 12 hrs at room temperature. The reaction mixture was evaporated in vacuo below 50° C. to give yellow oil, which was dissolved in EtOAc. The solid formed was filtered and washed with EtOAc. The filtrate and washing solution were combined, dried over $Na_2SO_4$. The solvent was concentrated in vacuo to give (S)-tetrahydro-5-oxofuran-2-carboxylic acid as pale yellow oil (8.1 g, 91.6%)[1].

MS (ESI, pos. ion) m/z: 130.9 (M+1);

$^1$H NMR (400 MHz, $CDCl_3$): δ2.27-2.41 (m, 1H), 2.44-2.65 (m, 3H), 5.09 (m, 1H), 9.12-9.55 (m, 1H).

Step 2) (S)-5-(hydroxymethyl)-dihydrofuran-2(3H)-one

To a solution of (S)-5-oxo-tetrahydrofuran-2-carboxylic acid (0.6 g, 0.0046 mol) in 10.8 mL of THF was added $BH_3.Me_2S$ solution (2.76 mL, 0.0055 mol, 2 M in THF, Aldrich) dropwise via a syringe at −20° C. The mixture was stirred for 12 hrs at room temperature. The reaction was then quenched with aqueous $NH_4Cl$ and extracted with EtOAc. The organic layer was washed with brine, dried over $Na_2SO_4$, and concentrated in vacuo to furnish the crude product as light yellow oil. (S)-5-(Hydroxymethyl)-dihydrofuran-2(3H)-one was obtained as colorless oil (0.253 g, 47%) after a silica gel column chromatography purification (100:1 (v/v) $CHCl_3$/MeOH)[1].

MS (ESI, pos. ion) m/z: 116.9 (M+1);

$^1$H NMR (400 MHz, $CDCl_3$): δ2.11-2.15 (m, 1H), 2.20-2.29 (m, 1H), 2.46-2.51 (m, 2H), 3.63 (t, 2H), 3.83-3.86 (d, J=14.8 Hz, 1H), 4.58-4.63 (m, 1H).

Step 3) (5S)-5-((tetrahydro-2H-pyran-2-yloxy)methyl)-dihydrofuran-2(3H)-one

To a mixture of (S)-5-(hydroxymethyl)-dihydrofuran-2(3H)-one (1.78 g, 0.0153 mol) and 3,4-dihydro-2H-pyran (2.62 g, 0.0312 mol, Alfa) in 40 mL of $CH_2Cl_2$ was added PPTS (0.391 g, 0.00156 mol, Aldrich) slowly. After stirring at rt overnight, the reaction mixture was quenched with 5 mL of water. The mixture was extracted with EtOAc (50 mL×2). The combined organic phases were dried over $Na_2SO_4$ and concentrated in vacuo to give pale yellow oil. The crude product was purified by a silica gel column chromatography (3:1 (v/v) petroleum ether/EtOAc) to afford the title compound as colorless oil (2.7 g, 88%).

MS (ESI, pos. ion) m/z: 200.8 (M+1);

$^1$H NMR (400 MHz, $CDCl_3$): δ 1.41-1.62 (m, 4H), 1.64-1.75 (m, 2H), 2.11-2.19 (m, 1H), 2.22-2.31 (m, 1H), 2.39-2.49 (m, 1H), 2.51-2.62 (m, 1H), 3.41-3.48 (m, 1H), 3.58-3.62 (dd, $J_1$=3.2 Hz, $J_2$=14.6 Hz, 1H), 3.74-3.79 (m, 1H), 3.85-3.92 (dd, $J_1$=3.2 Hz, $J_2$=14.4 Hz, 1H), 4.55-4.72 (m, 2H).

Step 4) 1-((S)-3-hydroxy-4-(tetrahydro-2H-pyran-2-yloxy)butyl)cyclopropanol

To a mixture of $Ti(OiPr)_4$ (0.33 mL, 0.001 mol, Ardrich) and (5S)-5-((tetrahydro-2H-pyran-2-yloxy)methyl)-dihydrofuran-2(3H)-one (1.0 g, 0.005 mol) in 18.7 mL of THF was added a solution of 3M EtMgBr in $Et_2O$ (4.3 mL, 0.0125 mol, Aldrich) via a syringe over 3 hrs at 15° C. After stirring for additional one hour at 15° C., the reaction was quenched with 20 mL of saturated $NH_4Cl$ solution, filtered and extracted with EtOAc (50 mL×2). The combined organic phases were dried over $Na_2SO_4$ and concentrated in vacuo. The residue was purified by a silica gel column chromatography to afford 1-((S)-3-hydroxy-4-(tetrahydro-2H-pyran-2-yloxy)butyl)cyclopropanol as colorless oil (0.853 g, 74%)[2].

MS (ESI, pos. ion) m/z: 253.0 (M+23);

$^1$H NMR (400 MHz, $CDCl_3$): δ0.4-0.5 (s, 1H), 0.67-0.87 (m, 3H), 1.4-1.9 (m, 12H), 3.38-3.44 (m, 1H), 3.53-3.60 (m, 1H), 3.75-3.78 (m, 1H), 3.87-3.96 (m, 1H), 4.57 (d, J=2.4 Hz, 1H).

Step 5) (5R)-5-((tetrahydro-2H-pyran-2-yloxy)methyl)-4-oxaspiro[2.4]heptane

To a solution of 14(S)-3-hydroxy-4-(tetrahydro-2H-pyran-2-yloxy)butyl)-cyclopropanol (1.73 g, 0.0075 mol) and $PPh_3$ (2.95 g, 0.0113 mol, Richjoint) in 32 mL of anhydrous THF at rt under $N_2$ was added DEAD (1.96 g, 0.0113 mol, Aladdin) dropwise via a syringe. The reaction was stirred at 60° C. for 12 hours. The solvent was concentrated in vacuo. The red oil was purified by a silica gel column chromatography (8:1 (v/v) n-hexane/EtOAc) to give the title compound as colorless oil (1.1 g, 64%)[2].

MS (ESI, pos. ion) m/z: 213.0 (M+1);

$^1$H NMR (400 MHz, $CDCl_3$): δ 0.4-0.6 (m, 2H), 0.75-0.95 (s, 2H), 1.4-1.9 (m, 10H), 3.45-3.52 (m, 2H), 3.73-3.79 (m, 1H), 3.80-3.90 (m, 1H), 4.23-4.28 (m, 1H), 4.63-4.69 (s, 1H).

Step 6) (5R)-5-(hydroxymethyl)-4-oxaspiro[2.4]heptane

To a mixture of (5R)-5-((tetrahydro-2H-pyran-2-yloxy)methyl)-4-oxaspiro[2.4]heptane (101 mg, 0.48 mmol) in 5 mL of MeOH was added PPTS (12.1 mg, 0.048 mol, Aldrich) at room temperature. The reaction mixture was stirred at 40° C. overnight and then concentrated in vacuo. The residue was purified by a silica gel column chromatography ($CH_2Cl_2$) to give the title compound as colorless oil (55 mg, 89%).

$^1$H NMR (400 MHz, $CDCl_3$): δ0.4-0.6 (m, 2H), 0.75-0.95 (m, 2H), 1.84-1.91 (m, 1H), 1.94-1.98 (m, 2H), 2.07-2.13 (m, 1H), 2.27 (s, 1H), 3.56-3.70 (m, 2H), 4.16-4.18 (m, 1H).

Step 7) ((5R)-4-oxaspiro[2.4]heptane-5-yl)methyl methanesulfonate

To a mixture of (5R)-5-(hydroxymethyl)-4-oxaspiro[2.4] heptane (116 mg, 0.9 mmol) and $Et_3N$ (183.8 mg, 1.82 mmol, Shantou Xilong chemical factory) in dry $CH_2Cl_2$ (6 mL) at −10° C. under $N_2$, was added MsCl (203 mg, 1.4 mmol, Shanghai Haiqu chemical Ltd.) dropwise via a syringe. After stirring for 2 hrs at rt, the reaction was quenched with water ice (3 mL), and the water phases were extracted with $CH_2Cl_2$ (20 mL×2). The combined organic phases were dried over $Na_2SO_4$, and concentrated in vacuo to give ((5R)-4-oxaspiro[2.4]heptane-5-yl)methyl methanesulfonate as pale yellow oil.

Step 8) N-(4-(7-(((5R)-4-oxaspiro[2.4]heptane-5-yl)methoxyl)quinolin-4-yloxy)-3-fluorophenyl)-2,3-dihydro-1,5-dimethyl-3-oxo-2-phenyl-1H-pyrazole-4-carboxamide

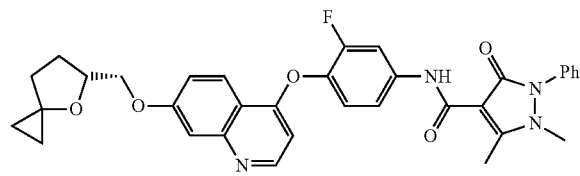

To a mixture of N-(4-(7-hydroxyquinolin-4-yloxy)-3-fluorophenyl)-2,3-dihydro-1,5-dimethyl-3-oxo-2-phenyl-1H-pyrazole-4-carboxamide (300 mg, 0.62 mmol) and cesium carbonate (1.0 g, 3.1 mmol, Aladdin) in N,N-dimethylacetamide (1 mL) was added ((5R)-4-oxaspiro[2.4]heptane-5-yl)methyl methanesulfonate (187.5 mg, 0.91 mmol) in 3 mL of N,N-dimethylacetamide. After stirring at 40° C. for 3 days, the reaction mixture was concentrated in vacuo and was chromatographed with a silica gel column (1:6 (v/v) n-hexane/EtOAc) to afford the title compound as a colorless solid (220 mg, 60%).

MS (ESI, pos. ion) m/z: 595.7 (M+1); LC-MS Rt: 4.17 min;

$^1$H NMR (400 MHz, CDCl$_3$): δ 0.63 (m, 2H), 0.91 (m, 2H), 2.03 (d, J=5.2 Hz, 3H), 2.29 (m, 1H), 2.80 (s, 3H), 3.38 (s, 3H), 4.17 (dd, J$_1$=16 Hz, J$_2$=2.4 Hz, 2H), 4.49 (m, 1H), 6.40 (d, J=5.2 Hz, 1H), 7.16 (t, 1H), 7.26 (d, J=5.2 Hz, 1H), 7.29 (d, J=2 Hz, 1H), 7.38 (m, 3H), 7.48 (m, 1H), 7.56 (t, 2H), 7.90 (dd, J$_1$=14.8 Hz, J$_2$=2.4 Hz, 1H), 8.26 (d, J=9.2 Hz, 1H), 8.58 (d, J=5.6 Hz, 1H), 10.87 (s, 1H).

Example 3

N-(5-(7-(((5R)-4-oxaspiro[2.4]heptane-5-yl)methoxyl)quinolin-4-yloxy)pyridin-2-yl)-2,3-dihydro-1,5-dimethyl-3-oxo-2-phenyl-1H-pyrazol-4-carboxamide

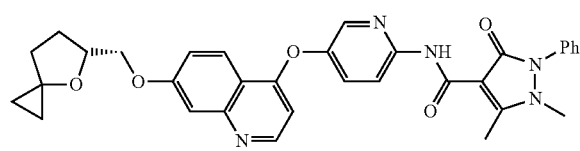

The title compound was prepared according to the procedure described in Example 2 by using N-(5-(7-hydroxyquinolin-4-yloxy)pyridin-2-yl)-2,3-dihydro-1,5-dimethyl-3-oxo-2-phenyl-1H-pyrazole-4-carboxamide (280 mg, 0.69 mmol), cesium carbonate (1.17 g, 3.45 mmol, Aladdin), and ((5R)-4-oxaspiro[2.4]heptane-5-yl)methyl methanesulfonate (204 mg, 0.99 mmol) in DMA (5 mL). The title compound was purified by a silica gel column chromatography (1:8 (v/v) n-hexane/EtOAc) as a colorless solid (110 mg, 27.6%).

MS (ESI, pos. ion) m/z: 578.1 (M+1); LC-MS Rt: 4.11 min;

$^1$H NMR (400 MHz, CDCl$_3$): δ0.55 (m, 2H), 0.92 (m, 2H), 2.03 (m, 3H), 2.31 (m, 1H), 2.81 (s, 3H), 3.38 (s, 3H), 4.18 (m, 2H), 4.52 (m, 1H), 6.43 (d, J=5.6 Hz, 1H), 7.28 (d, J=2.4 Hz, 1H), 7.30 (d, J=2.4 Hz, 1H), 7.39 (m, 3H), 7.51 (m, 4H), 8.23 (t, 1H), 8.38 (d, J=8.8 Hz, 1H), 8.60 (d, J=5.6 Hz, 1H), 11.25 (s, 1H).

Example 4

N-(3-fluoro-4-(7-(2-(1-hydroxycyclopropyl)ethoxy)quinolin-4-yloxy)phenyl)-1,5-dimethyl-3-oxo-2-phenyl-2,3-dihydro-1H-pyrazole-4-carboxamide

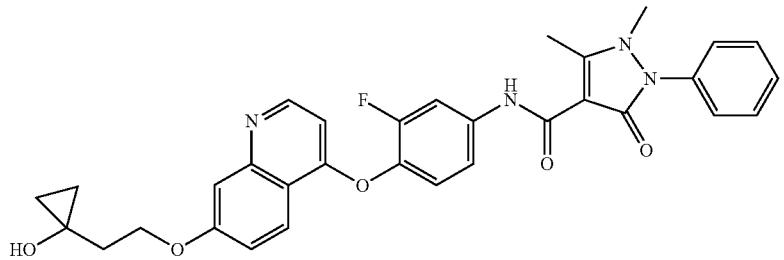 [SMILES: Cc1c(C(=O)Nc2ccc(Oc3ccnc4cc(OCCC5(O)CC5)ccc34)c(F)c2)c(=O)n(-c2ccccc2)n1C]

Step 1) 3-(tetrahydro-2H-pyran-2-yloxy)propanoic acid

To a mixture of 3-hydroxypropanoic acid (7.2 g, 80 mmol, TCI, TOKYO KASEI) and DHP (13.4 g, 160 mmol, Alfa) in dichloromethane (100 mL) and THF (100 mL) was added PPTS (2 g, 8 mmol, Aldrich) in portions. The reaction mixture was stirred at rt overnight, and was quenched with 50 mL of saturated NaHCO$_3$ aqueous solution. The resulted mixture was extracted with dichloromethane (50 mL×5). The combined organic phases were dried over Na$_2$SO$_4$ and concentrated in vacuo. The residue was purified by a silica gel column chromatography (1:1 (v/v) petroleum ether/EtOAc) to give colorless oil (7.8 g, 56%).

MS (ESI, pos. ion) m/z: 196.9 (M+Na$^+$); (ESI, negative. ion) m/z: 172.8 (M−1).

Step 2) benzyl 3-(tetrahydro-2H-pyran-2-yloxy)propanoate

To a solution of 3-(tetrahydro-2H-pyran-2-yloxy) propanoic acid (1 g, 5.7 mmol) and TEA (0.863 g, 8.55 mmol, Shantou Xilong chemical factory) in 50 mL of CH$_2$Cl$_2$ was added BnBr (0.98 g, 5.7 mmol, Aldrich) via a syringe at 0° C. After stirring at rt overnight, the reaction mixture was quenched with 20 mL of water, and was extracted with ethyl acetate (50 mL×3). The combined organic phases were dried over Na$_2$SO$_4$ and concentrated in vacuo. The residue was purified by a silica gel column chromatography (20:1 (v/v) petroleum ether/EtOAc) to give the title compound as colorless oil (270 mg, 18.6%).

MS (ESI, pos. ion) m/z: 287.0 (M+23);

$^1$H NMR (400 MHz, CDCl$_3$): δ 1.42-1.79 (m, 6H), 2.65-2.68 (t, 2H), 3.48-3.80 (dd, J=12.8 Hz, 2H), 3.71-4.01 (dd, J=12 Hz, 2H), 4.61 (d, 1H), 5.15 (s, 2H), 3.71-7.36 (m, 5H).

Step 3) 1-(2-(tetrahydro-2H-pyran-2-yloxy)ethyl) cyclopropanol

To a mixture of benzyl 3-(tetrahydro-2H-pyran-2-yloxy) propanoate (150 mg, 0.568 mmol) in 2 mL of THF was added Ti(Oi-Pr)$_4$ (0.18 mL, 0.568 mmol, d=0.955 g/L, Ardrich) via a syringe under nitrogen at rt. After stirring at 18° C. for 30 min, EtMgBr (0.48 mL, 1.42 mmol, 3M ether solution, Aldrich) was added via a syringe pump over 2 hrs. The reaction was quenched with 5 mL of water, after benzyl 3-(tetrahydro-2H-pyran-2-yloxy)propanoate was consumed completely (monitored by TLC). The mixture was filtered through a celite pad and the filtrate was extracted with ethyl acetate (30 mL×3). The combined organic phases were dried over Na$_2$SO$_4$ and concentrated in vacuo. The residue was purified by a silica gel column chromatography (10:1 (v/v) petroleum ether/EtOAc) to afford 1-(2-(tetrahydro-2H-pyran-2-yloxy) ethyl)cyclopropanol as colorless oil (60 mg, 57%).

$^1$H NMR (400 MHz, CDCl$_3$): δ0.46 (m, 2H), 0.75-0.88 (d, 2H), 1.55-1.83 (m, 6H), 1.87-1.90 (m, 2H), 3.55 (q, 1H), 3.69 (q, 1H), 3.88 (t, 1H), 4.06 (t, 1H), 4.66 (s, 1H).

Step 4) 1-(2-hydroxyethyl)cyclopropanol

To a mixture of 1-(2-(tetrahydro-2H-pyran-2-yloxy)ethyl) cyclopropanol (380 mg, 2.04 mmol) in 20 mL of methanol was added PPTS (51 mg, 0.204 mmol, Aldrich). The reaction mixture was stirred at 40° C. overnight, then treated with 10 mL of water. The resulted mixture was extracted with dichloromethane (20 mL×3). The combined organic phases were dried over Na$_2$SO$_4$ and concentrated in vacuo. The residue was purified by a silica gel column chromatography (10:1 (v/v) petroleum ether/EtOAc) to give the title compound as colorless oil (170 mg, 81.7%).

$^1$H NMR (400 MHz, CDCl$_3$): δ0.55 (t, 2H), 0.85 (t, 2H), 1.85 (t, 2H), 4.02 (t, 2H).

Step 5) 2-(1-hydroxycyclopropyl)ethyl methanesulfonate

A mixture of 1-(2-hydroxyethyl)cyclopropanol (86 mg, 0.843 mmol) and triethylamine (136 mg, 1.35 mmol, Shantou Xilong chemical factory) in 10 mL of dichloromethane was stirred at −10° C. for 30 min. Methanesulfonyl chloride (106 mg, 0.927 mmol, Shanghai Haiqu chemical Ltd.) was then added via a syringe. The reaction was stirred at −10° C. for 1 hr at rt and then quenched with 1 mL ice-water. The resulted mixture was extracted with dichloromethane (20 mL×3). The combined organic phases were dried over Na$_2$SO$_4$ and concentrated in vacuo to afford 2-(1-hydroxycyclopropyl)ethyl methanesulfonate as yellow oil (used in the next step without further purification).

Step 6) N-(3-fluoro-4-(7-(2-(1-hydroxycyclopropyl) ethoxy)quinolin-4-yloxy)phenyl)-1,5-dimethyl-3-oxo-2-phenyl-2,3-dihydro-1H-pyrazole-4-carboxamide

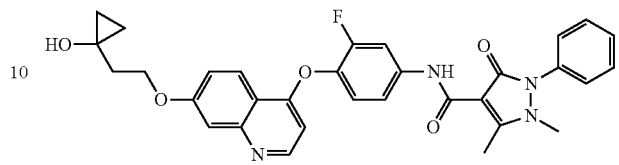

To a mixture of N-(3-fluoro-4-(7-hydroxyquinolin-4-yloxy)phenyl)-1,5-dimethyl-3-oxo-2-phenyl-2,3-dihydro-1H-pyrazole-4-carboxamide (204 mg, 0.421 mmol) and 2-(1-hydroxycyclopropyl)ethyl methanesulfonate (152 mg, 0.843 mmol) in 8 mL of DMA was added cesium carbonate (1.37 g, 4.2 mmol, Aladdin). After stirring at 40° C. for 1 day, the reaction mixture was concentrated in vacuo and the residue was chromatographed with a silica gel column (50:1 (v/v) CH$_2$Cl$_2$/CH$_3$OH) to afford the title compound as a white solid (60 mg, 25%).

MS (ESI, pos. ion) m/z: 569.1 (M+1); LC-MS Rt: 3.948 min;

$^1$H NMR (400 MHz, CDCl$_3$): δ0.57 (d, J=8 Hz, 2H), 0.86 (d, J=8 Hz, 2H), 2.14 (t, 2H), 2.80 (s, 3H), 3.37 (s, 3H), 4.43 (t, 2H), 6.41 (d, J=4 Hz, 1H), 7.14-7.23 (m, 2H), 7.26-7.35 (m, 1H), 7.37-7.38 (m, 2H), 7.45-7.50 (m, 2H), 7.50-7.58 (m, 2H), 7.90-7.93 (dd, J=2.4 Hz, 1H), 8.27 (d, J=8 Hz, 1H), 8.58 (d, J=8 Hz, 1H), 10.89 (s, 1H).

Example 5

N-(3-fluoro-4-(7-((1-cyclopropyl methanesulfonate-1-yl)methoxyl)quinolin-4-yloxy)phenyl)-1,5-dimethyl-3-oxo-2-phenyl-2,3-dihydro-1H-pyrazole-4-carboxamide

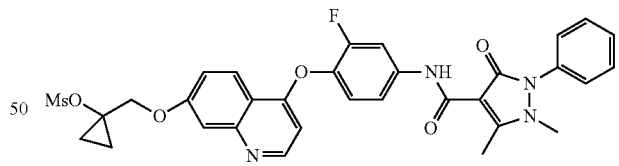

Step 1) ethyl 2-(tetrahydro-2H-pyran-2-yloxy)acetate

To a mixture of ethyl 2-hydroxyacetate (2 g, 20 mmol, TCI) and 3,4-dihydro-2H-pyran (3.2 g, 40 mmol, Alfa) in 40 mL of CH$_2$Cl$_2$ was added PPTS (500 mg, 2 mmol, Aldrich) in portions at rt. The mixture was stirred at rt for 4 hours. The reaction mixture was then washed with brine, and the organic layer was separated and the combined organic phases were dried over Na$_2$SO$_4$, concentrated in vacuo. The residue was purified by a silica gel column chromatography (20:1 (v/v) petroleum ether/EtOAc) to give the desired compound as colorless oil (3.01 g, 81%).

$^1$H NMR (400 MHz, CDCl$_3$): δ 1.25-1.32 (m, 3H), 1.55-1.63 (m, 3H), 1.69-1.88 (m, 3H), 3.50-3.53 (m, 1H), 3.82-3.88 (m, 1H), 4.18-4.23 (m, 4H), 4.73 (t, J=3.2 Hz, 1H).

Step 2) 1-((tetrahydro-2H-pyran-2-yloxy)methyl) cyclopropanol

To a mixture of ethyl 2-(tetrahydro-2H-pyran-2-yloxy)acetate (1 g, 5.3 mmol) and Ti(O-iPr)$_4$ (1.06 mL, 3.5 mmol, Aldrich) in 18 mL of THF under N$_2$ was added EtMgBr (4.5 mL, 13.25 mmol, 3M ether solution, Aldrich) dropwise over 2 hrs, and the temperature must be kept at 15-20° C. After stirring for 2 hrs, and the reaction mixture was quenched with saturated NH$_4$Cl aqueous solution at 0° C. and extracted with EtOAc (30 mL×3). The combined organic phases were dried over Na$_2$SO$_4$ and concentrated in vacuo. The residue was purified by a silica gel column chromatography (20:1 (v/v) petroleum ether/EtOAc) to afford 1-((tetrahydro-2H-pyran-2-yloxy)methyl)cyclopropanol as colorless oil (500 mg, 55%).

$^1$H NMR (400 MHz, CDCl$_3$): δ 0.51-0.67 (m, 2H), 0.77-0.85 (m, 2H), 1.55-1.65 (m, 4H), 1.74-1.87 (m, 2H), 3.50-3.55 (m, 2H), 3.81 (d, J=11.6 Hz, 1H), 3.93-3.98 (m, 2H), 4.64-4.66 (m, 1H).

Step 3) 1-(hydroxymethyl)cyclopropanol

To a mixture of 1-((tetrahydro-2H-pyran-2-yloxy)methyl) cyclopropanol (420 mg, 2.44 mmol) in 30 mL of MeOH was added PPTS (61 mg, 0.244 mmol, Aldrich) at rt. The reaction mixture was stirred at rt overnight, and then concentrated and purified by a silica gel column chromatography (1:2 (v/v) petroleum ether/EtOAc) to afford 1-(hydroxymethyl)-cyclopropanol as colorless oil (209 mg, 99%).

$^1$H NMR (400 MHz, CDCl$_3$): δ 0.56 (t, J=5.6 Hz, 2H), 0.82 (t, J=6 Hz, 2H), 3.62 (s, 2H).

Step 4) (1-(methylsulfonyloxy)cyclopropyl)methyl methanesulfonate

To a mixture of 1-(hydroxymethyl)cyclopropanol (100 mg, 1.14 mmol) and TEA (202 mg, 1.82 mmol, Shantou Xilong chemical factory) in 20 mL of dry CH$_2$Cl$_2$ under N$_2$, was added MsCl (156 mg, 1.32 mmol, Shanghai Haiqu chemical Ltd.) dropwise via a syringe at −10° C. After stirring for 4 hrs at −10° C., the mixture was washed with ice-water and extracted with CH$_2$Cl$_2$ (30 mL×3). The combined organic phases were dried over Na$_2$SO$_4$ and concentrated in vacuo to give the desired compound as pale yellow oil (139 mg, 50%).

Step 5) N-(3-fluoro-4-(7-((1-cyclopropyl methanesulfonate-1-yl)methoxyl)quinolin-4-yloxy)phenyl)-1,5-dimethyl-3-oxo-2-phenyl-2,3-dihydro-1H-pyrazole-4-carboxamide

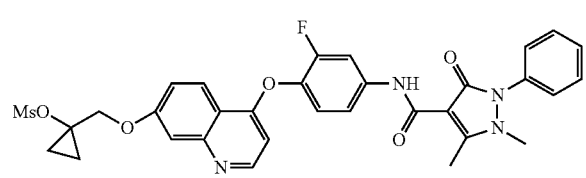 [SMILES: Cc1c(C(=O)Nc2ccc(Oc3ccnc4cc(OCC5(OS(C)(=O)=O)CC5)ccc34)c(F)c2)c(=O)n(-c2ccccc2)n1C]

To a mixture of (1-(methylsulfonyloxy)cyclopropyl)methyl methanesulfonate (122 mg, 0.5 mmol) and N-(4-(7-hydroxyquinolin-4-yloxy)-3-fluorophenyl)-2,5-dihydro-2,3-dimethyl-5-oxo-1-phenyl-1H-pyrazole-4-carboxamide (306 mg, 0.57 mmol) in 3 mL of DMA under N$_2$ was added Cs$_2$CO$_3$ (926 mg, 2.84 mmol, Aladdin) at rt. The mixture was stirred at rt overnight, and then was concentrated in vacuo. The residue was purified by a silica gel column chromatography (5:1 (v/v) CH$_2$Cl$_2$/EtOAc) to give the title compound as a white solid (200 mg, 55%).

MS (ESI, pos. ion) m/z: 633.1 (M+1); LC-MS Rt: 4.178 min;

$^1$H NMR (400 MHz, CDCl$_3$): δ 1.09 (t, J=7.2 Hz, 2H), 1.54 (t, J=6.8 Hz, 2H), 2.80 (s, 3H), 3.07 (s, 3H), 3.38 (s, 3H), 4.45 (s, 2H), 6.43 (d, J=4.2 Hz, 2H), 7.17 (t, J=8.8 Hz, 1H), 7.27-7.32 (m, 2H), 7.36-7.40 (dd, J=0.2 Hz, 3H), 7.49 (d, J=7.2 Hz, 1H), 7.57 (t, J=8 Hz, 2H), 7.90-7.94 (dd, J=2.4 Hz, 1H), 8.31 (d, J=4.2 Hz, 1H), 8.60 (d, J=4.2 Hz, 1H).

Example 6

N-(4-(7-(4-oxaspiro[2.4]heptane-6-yloxy)-6-methoxyl-quinolin-4-yloxy)-3-fluorophenyl)-2,3-dihydro-1,5-dimethyl-3-oxo-2-phenyl-1H-pyrazole-4-carboxamide

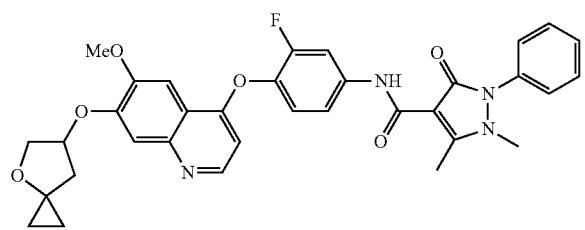 [SMILES: COc1cc2c(Oc3ccc(NC(=O)c4c(C)n(C)n(-c5ccccc5)c4=O)cc3F)ccnc2cc1OC1COC2(CC2)C1]

Step 1) 4-(tetrahydro-2H-pyran-2-yloxy)-dihydrofuran-2(3H)-one

To a mixture of 4-hydroxy-dihydrofuran-2(3H)-one (10 g, 0.1 mol, Alfa) and dihydropyran (12.5 g, 0.15 mol, Alfa) in 250 mL of dry CH$_2$Cl$_2$ was added PPTS (2.5 g 0.01 mol), and the reaction mixture was stirred at rt overnight. The reaction mixture was washed with brine and extracted with CH$_2$Cl$_2$ (100 mL×3), and the combined organic phases were dried over Na$_2$SO$_4$ and concentrated in vacuo. The residue was purified by a silica gel column chromatography (3:1 (v/v) EtOAc/n-Hexane) to give the title compound as colorless oil (15.6 g, 68%).

$^1$H NMR (400 MHz, CDCl$_3$): δ 1.63-1.84 (m, 6H), 2.54-2.79 (m, 2H), 3.52-3.55 (dd, J=12 Hz, 1H), 3.79-3.86 (m, 1H), 4.31-4.47 (m, 2H), 4.57-4.59 (t, J=4 Hz, 2H).

Step 2) 1-(3-hydroxy-2-(tetrahydro-2H-pyran-2-yloxy)propyl)cyclopropanol

To a solution of 4-(tetrahydro-2H-pyran-2-yloxy)-dihydrofuran-2(3H)-one (2.23 g, 12 mmol) and Ti(Oi-Pr)$_4$ (0.68 g, 2.4 mmol, Aldrich) in 40 mL of dry THF at 15° C. under N$_2$ was added EtMgBr (30 mmol, 10 mL, 3M ether solution, Aldrich) dropwise via a syringe pump over 2 hrs. The temperature of the reaction was always kept below 20° C. After stirring for 2 hrs, the reaction mixture was quenched with 30 mL of saturated NH$_4$Cl aqueous solution, and was extracted with ethyl acetate (50 mL×3). The combined organic phases were dried over Na$_2$SO$_4$ and concentrated in vacuo. The residue was purified by a silica gel column chromatography (1:1

(v/v) EtOAc/n-hexane) to afford 1-(3-hydroxy-2-(tetrahydro-2H-pyran-2-yloxy)propyl)cyclopropanol as yellow oil (1.92 g, 73%).[2]

$^1$H NMR (400 MHz, CDCl$_3$): δ 0.40-0.53 (m, 2H), 0.71-0.83 (m, 2H), 1.53-1.67 (m, 5H), 1.81-1.96 (m, 3H), 3.49-3.72 (m, 3H), 3.98-4.11 (m, 2H), 4.64-4.73 (m, 1H).

Step 3) 3-(1-hydroxycyclopropyl)-2-(tetrahydro-2H-pyran-2-yloxy)propyl methanesulfonate To a mixture of 1-(3-hydroxy-2-(tetrahydro-2H-pyran-2-yloxy)propyl)cyclopropanol (1.0 g, 4.63 mmol) and triethylamine (1 mL, 7.4 mmol, Shantou Xilong chemical factory) in 30 mL of CH$_2$Cl$_2$ at 0° C. was added methanesulfonyl chloride (0.64 g, 5.6 mmol, Shanghai Haiqu chemical Ltd.) via a syringe. The reaction mixture was stirred at 0° C. for 1 hr and then quenched with 5 mL of ice-water. The resulted mixture was extracted with CH$_2$Cl$_2$ (50 mL×3). The combined organic phases were dried over Na$_2$SO$_4$ and concentrated in vacuo to furnish 3-(1-hydroxycyclopropyl)-2-(tetrahydro-2H-pyran-2-yloxy)propyl methanesulfonate as yellow oil (used in the next step immediately without further purification).

Step 4) 6-(tetrahydro-2H-pyran-2-yloxy)-4-oxaspiro[2.4]heptane

A mixture of 3-(1-hydroxycyclopropyl)-2-(tetrahydro-2H-pyran-2-yloxy)propyl methanesulfonate (1.3 g, 4.63 mmol) and NaH (0.15 g, 6 mmol, Aldrich) in 20 mL of THF was stirred at rt for 4 hrs. The reaction mixture was quenched with 5 mL of methanol. The mixture was diluted with 10 mL of water and extracted with ethyl acetate (30 mL×3). The combined organic phases were dried over Na$_2$SO$_4$ and concentrated in vacuo. The residue was purified by a silica gel column chromatography (1:10 (v/v) EtOAc/petroleum ether) to give the title compound as colorless oil (380 mg, 42%).

$^1$H NMR (400 MHz, CDCl$_3$): δ 0.45-0.63 (dd, J=4.8 Hz, 2H), 0.81-0.93 (dd, J=4.8 Hz, 2H), 1.56-2.29 (m, 8H), 3.54 (s, 1H), 3.87-4.03 (m, 3H), 4.60-4.66 (m, 2H).

Step 5) 6-hydroxy-4-oxaspiro[2.4]heptane

A mixture of 6-(tetrahydro-2H-pyran-2-yloxy)-4-oxaspiro[2.4]heptane (1.03 g, 5.2 mmol) and PPTS (0.26 g, 1.0 mmol, Aldrich) in methanol (40 ml) was stirred at 40° C. for 5 hrs. The reaction mixture was concentrated in vacuo, and the residue was purified by a silica gel column chromatography (1:5 (v/v) EtOAc/petroleum ether) to afford 6-hydroxy-4-oxaspiro[2.4]heptane as colorless oil (570 mg, 97%).

$^1$H NMR (400 MHz, CDCl$_3$): δ 0.47-0.65 (m, 2H), 0.81-0.96 (m, 2H), 1.89-2.35 (m, 2H), 3.80-3.96 (m, 2H), 4.59 (s, 1H)

Step 6) (4-oxaspiro[2.4]heptane-6-yl)methanesulfonate

To a mixture of 6-hydroxy-4-oxaspiro[2.4]heptane (100 mg, 0.88 mmol) and triethylamine (150 mg, 1.5 mmol, Shantou Xilong chemical factory) in 5 mL of dichloromethane at 0° C. was added methanesulfonyl chloride (130 mg, 1 mmol, Shanghai Haiqu chemical Ltd.) via a syringe. The reaction mixture was stirred at 0° C. for 1 hr and was quenched with 5 mL of ice-water. The resulted mixture was extracted with CH$_2$Cl$_2$ (20 mL×3). The combined organic phases were dried over Na$_2$SO$_4$ and concentrated in vacuo to give the title compound as yellow oil (168 mg, 100%).

Step 7) N-(4-(7-(4-oxaspiro[2.4]heptane-6-yloxy)-6-methoxyquinolin-4-yloxy)-3-fluorophenyl)-2,3-dihydro-1,5-dimethyl-3-oxo-2-phenyl-1H-pyrazole-4-carboxamide

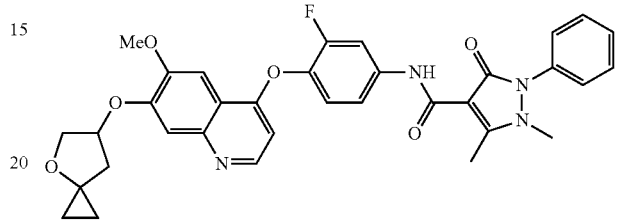

To a mixture of (4-oxaspiro[2.4]heptane-6-yl)methanesulfonate (168 mg, 0.877 mmol) and N-(4-(7-hydroxy-6-methoxyquinolin-4-yloxy)-3-fluorophenyl)-2,3-dihydro-1,5-dimethyl-3-oxo-2-phenyl-1H-pyrazole-4-carboxamide (300 mg, 0.584 mmol) in 5 mL of N,N-dimethylacetamide was added cesium carbonate (893 mg, 2.74 mmol, Aladdin). After stirring at rt for 4 hrs, the reaction was warmed to 40° C. and stirred for 16 hrs. The reaction mixture was concentrated in vacuo and chromatographed with a silica gel column (5:1 (v/v) EtOAc/n-hexane) to afford the title compound as a white solid (65 mg, 18%).

MS (ESI, pos. ion) m/z: 611.1 [M+1]; LC-MS Rt: 4.10 min;

$^1$H NMR (400 MHz, CDCl$_3$): δ 0.56-0.71 (m, 2H), 0.81-1.02 (m, 2H), 2.33 (m, 1H), 2.55 (m, 1H), 2.81 (s, 3H), 3.38 (s, 3H), 4.03 (s, 3H), 4.21 (m, 2H), 5.24 (t, J=4 Hz, 1H), 6.43 (d, J=4 Hz, 1H), 7.15-7.60 (m, 9H), 7.90-7.94 (m, 1H), 8.48 (d, J=4 Hz, 1H), 10.89 (s, 1H).

Example 7

N-(4-(7-(4-oxaspiro[2.4]heptane-6-yloxy)quinolin-4-yloxy)-3-fluorophenyl)-2,3-dihydro-1,5-dimethyl-3-oxo-2-phenyl-1H-pyrazole-4-carboxamide

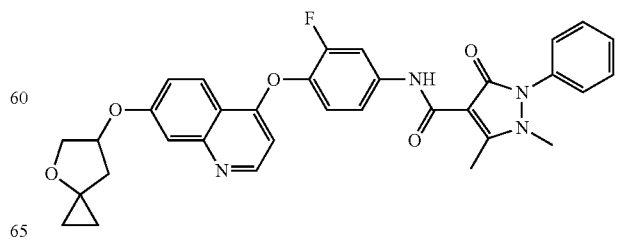

The title compound was prepared according to the procedure described in Example 6 by using (4-oxaspiro[2.4]heptane-6-yl)methanesulfonate (220 mg, 1.14 mmol), N-(4-(7-hydroxyquinolin-4-yloxy)-3-fluorophenyl)-2,3-dihydro-1,5-dimethyl-3-oxo-2-phenyl-1H-pyrazole-4-carboxamide (300 mg, 0.62 mmol), and cesium carbonate (450 mg, 2.4 mmol, Aladdin) in DMA (6 mL). The title compound was purified by a silica gel column chromatography (5:1 (v/v) EtOAc/n-hexane) and was obtained as a white solid (68 mg, 19%).

MS (ESI, pos. ion) m/z: 581.1 [M+1]; LC-MS Rt: 4.255 min;

$^1$H NMR (400 MHz, CDCl$_3$): δ 0.54-0.72 (m, 2H), 0.88-1.07 (m, 2H), 2.29 (m, 1H), 2.57 (m, 1H), 2.84 (s, 3H), 3.42 (s, 3H), 4.22 (m, 2H), 5.26 (m, 1H), 6.46 (d, J=4 Hz, 1H), 7.18-7.63 (m, 9H), 7.96 (m, 1H), 8.33 (d, J=8 Hz, 1H), 8.62 (d, J=4 Hz, 1H), 10.92 (s, 1H).

Example 8

N-(5-(7-(4-oxaspiro[2.4]heptane-6-yloxy)quinolin-4-yloxy)pyridin-2-yl)-2,3-dihydro-1,5-dimethyl-3-oxo-2-phenyl-1H-pyrazole-4-carboxamide

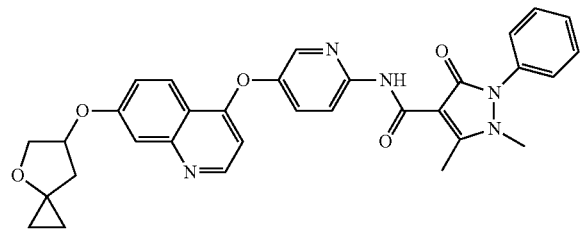 [SMILES: Cc1c(C(=O)Nc2ccc(Oc3ccnc4cc(OC5COC6(CC6)C5)ccc34)cn2)c(=O)n(-c2ccccc2)n1C]

The title compound was prepared according to the procedure described in Example 6 by using (4-oxaspiro[2.4]heptane-6-yl)methanesulfonate (220 mg, 1.14 mmol), N-(5-(7-hydroxyquinolin-4-yloxy)pyridin-2-yl)-2,3-dihydro-1,5-dimethyl-3-oxo-2-phenyl-1H-pyrazole-4-carboxamide (300 mg, 0.64 mmol), and cesium carbonate (450 mg, 2.4 mmol, Aladdin) in DMA (6 mL). The title compound was purified with a silica gel column chromatography (EtOAc) to give a white solid (140 mg, 39%).

MS (ESI, pos. ion) m/z: 564.1 [M+1]; LC-MS Rt: 4.007 min;

$^1$H NMR (400 MHz, CDCl$_3$): δ 0.59 (m, 2H), 0.91 (m, 2H), 2.25 (d, J=14 Hz, 1H), 2.53 (m, 1H), 2.80 (s, 3H), 3.37 (s, 3H), 4.18 (m, 2H), 5.22 (t, J=4 Hz, 1H), 6.44 (d, J=5 Hz, 1H), 7.24-7.56 (m, 9H), 8.25 (m, 1H), 8.38 (d, J=9 Hz, 1H), 8.60 (d, J=3 Hz, 1H), 11.26 (s, 1H).

Example 9

N-(3-fluoro-4-(7-(3-(1-hydroxycyclopropyl)propoxy)quinolin-4-yloxy)phenyl)-1,5-dimethyl-3-oxo-2-phenyl-2,3-dihydro-1H-pyrazole-4-carboxamide

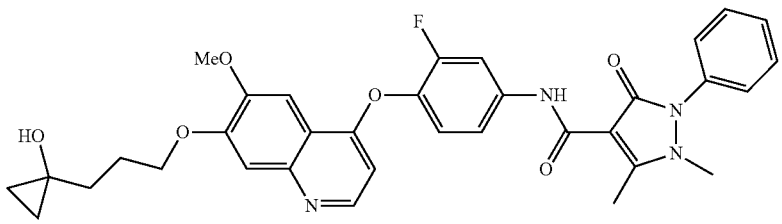 [SMILES: COc1cc2c(Oc3ccc(NC(=O)c4c(C)n(C)n(-c5ccccc5)c4=O)cc3F)ccnc2cc1OCCCC1(O)CC1]

Step 1) 1-(3-hydroxypropyl)cyclopropanol

To a mixture of dihydrofuran-2(3H)-one (2.0 g, 23 mmol, Alfa) and Ti(Oi-Pr)$_4$ (1.32 g, 4.6 mmol, Aldrich) in 80 mL of dry THF at 15° C. under N$_2$ was added EtMgBr (60 mmol, 20 mL, 3M in ether solution, Aldrich) via a syringe pump over 3 hrs.

The temperature was always kept below 20° C. After stirring for additional 3 hrs, the reaction mixture was quenched with 60 mL of saturated NH$_4$Cl aqueous solution, and was extracted with ethyl acetate (50 mL×3). The combined organic phases were dried over Na$_2$SO$_4$ and concentrated in vacuo. The orange oil residue was purified by a silica gel column chromatography (1:1 (v/v) EtOAc/n-Hexane) to afford 1-(3-hydroxypropyl)cyclopropanol as yellow oil (2.5 g, 93%).

Step 2) 3-(1-hydroxycyclopropyl)propyl methanesulfonate

A mixture of 1-(3-hydroxypropyl)cyclopropanol (140 mg, 1.2 mmol) and triethylamine (0.3 mL, 2.1 mmol, Shantou Xilong chemical factory) in 8 mL of dichloromethane was stirred at 0° C. for 10 min. To the mixture was added methanesulfonyl chloride (180 mg, 1.6 mmol, Shanghai Haiqu chemical Ltd.) via a syringe. The reaction mixture was stirred at 0° C. for 1 hr and then quenched with 2 mL of ice-water. The resulted mixture was extracted with dichloromethane (10 mL×3). The combined organic phases were dried over Na$_2$SO$_4$ and concentrated in vacuo to give 3-(1-hydroxycyclopropyl) propyl methanesulfonate as yellow oil.

Step 3) N-(3-fluoro-4-(7-(3-(1-hydroxycyclopropyl)propoxy)quinolin-4-yloxy)phenyl)-1,5-dimethyl-3-oxo-2-phenyl-2,3-dihydro-1H-pyrazole-4-carboxamide

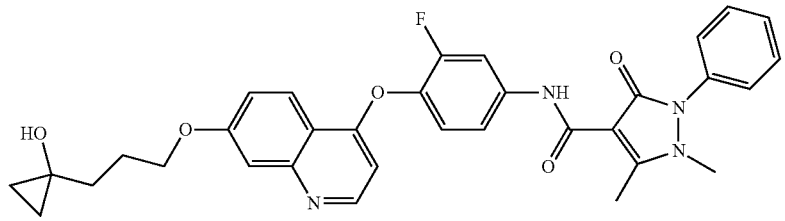 [SMILES: Cc1c(C(=O)Nc2ccc(Oc3ccnc4cc(OCCCC5(O)CC5)ccc34)c(F)c2)c(=O)n(-c2ccccc2)n1C]

To a mixture of 3-(1-hydroxycyclopropyl)propyl methanesulfonate (240 mg, 1.2 mmol) and N-(4-(7-hydroxyquinolin-4-yloxy)-3-fluorophenyl)-2,3-dihydro-1,5-dimethyl-3-oxo-2-phenyl-1H-pyrazole-4-carboxamide (300 mg, 0.62 mmol) in 5 mL of N,N-dimethylacetamide was added cesium carbonate (470 mg, 2.4 mmol, Aladdin). After stirring at rt for 12 hrs, the reaction mixture was warmed to 40° C. and stirred for additional 6 hrs. The reaction mixture was diluted with 20 mL of water and extracted with ethyl acetate (40 mL×3). The combined organic phases were dried over Na$_2$SO$_4$, concentrated in vacuo and chromatographed with a silica gel column (5:1 (v/v) EtOAc/n-Hexane) to provide the title compound as a white solid (68 mg, 19%).

MS (ESI, pos. ion) m/z: 583.1 [M+1]; LC-MS Rt: 4.129 min;

$^1$H NMR (400 MHz, CDCl$_3$): δ 0.51 (m, 2H), 0.79 (m, 2H), 1.81 (t, J=8 Hz, 2H), 2.15 (m, 2H), 2.81 (s, 3H), 3.38 (s, 3H), 4.24 (t, J=8 Hz, 2H), 6.41 (d, J=4 Hz, 1H), 7.15-7.59 (m, 9H), 7.91 (m, 1H), 8.27 (d, J=8 Hz, 1H), 8.58 (d, J=4 Hz, 1H), 10.87 (s, 1H).

N-(3-fluoro-4-(7-(3-(1-cyclopropyl-methanesulfonate-1-yl)propoxy)-quinolin-4-yloxy)phenyl)-1,5-dimethyl-3-oxo-2-phenyl-2,3-dihydro-1H-pyrazole-4-carboxamide was also isolated from the above reaction:

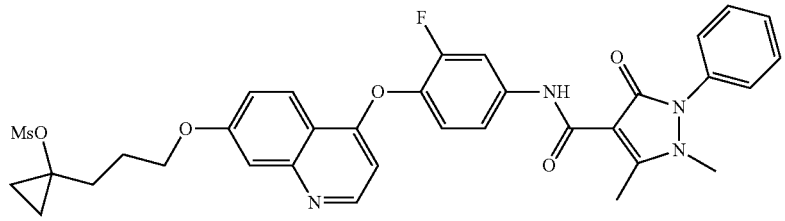 [SMILES: Cc1c(C(=O)Nc2ccc(Oc3ccnc4cc(OCCCC5(OS(C)(=O)=O)CC5)ccc34)c(F)c2)c(=O)n(-c2ccccc2)n1C]

MS (ESI, pos. ion) m/z: 661.1 [M+1]; LC-MS Rt: 4.272 min;

$^1$H NMR (400 MHz, CDCl$_3$): δ 0.787 (m, 2H), 1.29 (m, 2H), 2.11 (m, 4H), 2.80 (s, 3H), 3.01 (s, 3H), 3.38 (s, 3H), 4.22 (t, J=6 Hz, 2H), 6.41 (d, J=5 Hz, 1H), 7.14-7.59 (m, 9H), 7.91 (m, 1H), 8.27 (d, J=9 Hz, 1H), 8.58 (d, J=5 Hz, 1H), 10.88 (s, 1H).

Example 10

N-(5-(7-(3-(1-hydroxycyclopropyl)propoxy)quinolin-4-yloxy)pyridin-2-yl)-1,5-dimethyl-3-oxo-2-phenyl-2,3-dihydro-1H-pyrazole-4-carboxamide

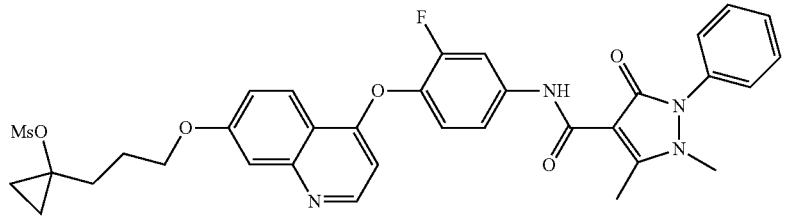

The title compound was prepared according to the procedure described in Example 9 by using N-(5-(7-hydroxyquinolin-4-yloxy)pyridin-2-yl)-1,5-dimethyl-3-oxo-2-phenyl-2,3-dihydro-1H-pyrazole-4-carboxamide (277 mg, 0.593 mmol), $Cs_2CO_3$ (560 mg, 1.724 mmol, Aladdin), and 3-(1-hydroxycyclopropyl)propyl methanesulfonate (334 mg, 1.724 mmol) in DMA (10 mL). The title compound was purified by a silica gel column chromatography (67:30:1:2 (v/v/v/v) EtOAc/$CH_2Cl_2$/$CH_3OH$/$Et_3N$) to afford the title compound as a white solid (210 mg, 62.6%).

MS (ESI, pos. ion) m/z: 566 [M+1]; LC-MS Rt: 3.846 min;
$^1$H NMR (400 MHz, $CDCl_3$): δ 0.49-052 (t, J=6 Hz, 2H), 0.78-0.81 (t, J=6 Hz, 2H), 1.26 (s, 2H), 1.79-1.83 (t, J=7.2 Hz, 2H), 2.13-2.16 (t, J=7.2 Hz, 2H), 2.81 (s, 3H), 3.38 (s, 3H), 4.23-4.26 (t, J=6 Hz, 2H), 6.42-6.44 (d, J=5.2 Hz, 1H), 7.20-7.23 (q, $J_1$=9.2 Hz, $J_2$=2.4 Hz, 1H), 7.37-7.39 (d, J=7.6 Hz,

Example 11

N-(5-(7-((4-oxaspiro[2.4]heptane-6-yl)aminopropoxy)quinolin-4-yloxy)pyridin-2-yl)-2,3-dihydro-1,5-dimethyl-3-oxo-2-phenyl-1H-pyrazole-4-carboxamide

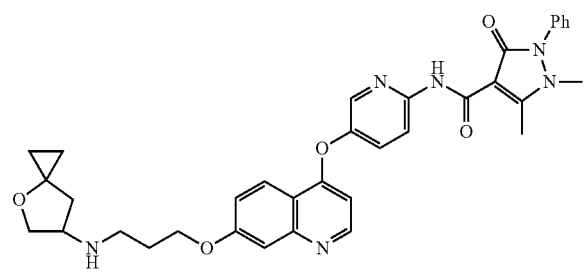 [SMILES: Cc1c(C(=O)Nc2ccc(Oc3ccnc4cc(OCCCNC5COC6(CC6)C5)ccc34)cn2)c(=O)n(-c2ccccc2)n1C]

Step 1) (4-oxaspiro[2.4]heptane-6-yl)methanesulfonate

To a solution of 6-hydroxy-4-oxaspiro[2.4]heptane (200 mg, 1.75 mmol) and $Et_3N$ (530.25 mg, 5.25 mmol) in dry $CH_2Cl_2$ (8 mL) at −10° C. was added MsCl (401.7 mg, 3.5 mmol) dropwise under $N_2$ atmosphere. After stirring for 2 hrs, the reaction was quenched with ice-water (3 mL), extracted with $CH_2Cl_2$ (2×10 mL). The combined organic phases were dried over $Na_2SO_4$, concentrated in vacuo to give the title compound as pale yellow oil.

Step 2) (4-oxaspiro[2,4]heptane-6-yl)aminopropanol

To a solution of (4-oxaspiro[2,4]heptane-6-yl)methanesulfonate (336 mg, 1.75 mmol) in dry THF (3 mL) was added 3-aminopropan-1-ol (656.3 mg, 8.75 mmol, TCI). The reaction was refluxed overnight. The mixture was concentrated in vacuo to give a brown residue, which was chromatographed with a silica gel column (8:1 (v/v) EtOAc/MeOH) to give the title compound as pale yellow oil (280 mg, 93%).

MS (ESI, pos. ion) m/z: 171.0 (M+1).
$^1$H NMR (400 MHz, $CDCl_3$): δ 0.45 (m, 1H), 0.54 (m, 1H), 0.88 (m, 2H), 1.75 (m, 2H), 1.83 (dd, $J_1$=4 Hz, $J_2$=16.8 Hz, 1H), 2.22 (dd, $J_1$=7.2 Hz, $J_2$=20 Hz, 1H), 2.40 (s, 2H), 3.58 (m, 1H), 3.72 (m, 1H), 3.83 (t, 2H), 3.96 (dd, $J_1$=14.8 Hz, $J_2$=5.6 Hz, 1H).

Step 3) tert-butyl N-(4-oxaspiro[2.4]heptane-6-yl)hydroxypropylamino formate To a solution of (4-oxaspiro[2.4]heptane-6-yl)aminopropanol (361.9 mg, 2.12 mmol) and $Et_3N$ (535.3 mg, 5.3 mmol) in $CH_2Cl_2$ (10 mL) at room temperature was added $(Boc)_2O$ (692 mg, 3.17 mmol). The reaction was stirred overnight and was then quenched with water (5 mL). The organic layer was separated and the water layer was extracted with 20 mL of EtOAc. The combined organic phases were dried over $Na_2SO_4$, concentrated in vacuo to give the title compound as pale yellow oil (555.8 mg, 97%).

MS (ESI, pos. ion) m/z: 272.0 (M+1);
$^1$H NMR (400 MHz, $CDCl_3$): δ 0.45 (m, 1H), 0.61 (m, 1H), 0.78 (m, 1H), 0.93 (m, 1H), 1.47 (s, 9H), 1.75 (m, 3H), 2.13 (t, 2H), 3.42 (s, 2H), 3.59 (d, J=5.2 Hz, 2H), 3.76 (dd, $J_1$=5.6 Hz, $J_2$=14.8 Hz, 1H), 3.94 (dd, $J_1$=7.6 Hz, $J_2$=16.4 Hz, 1H), 4.71 (s, 1H).

Step 4) (N-(4-oxaspiro[2.4]heptane-6-yl)-tert butoxycarbonylamino)propyl methanesulfonate To a solution of tert-butyl N-(4-oxaspiro[2.4]heptane-6-yl) hydroxypropylamino formate (278 mg, 1.03 mmol) and $Et_3N$ (260 mg, 2.58 mmol) in dry $CH_2Cl_2$ (10 mL) at −10° C. was added MsCl (234.8 mg, 2.06 mmol) dropwise under $N_2$ atmosphere. After stirring for 2 hrs, the reaction was quenched with ice water (3 mL). The organic phase was separated and the water layer was extracted with 15 mL of $CH_2Cl_2$. The combined organic phases were dried over $Na_2SO_4$, concentrated in vacuo to give the title compound as pale yellow oil.

Step 5) N-(5-(7-((N-(4-oxaspiro[2.4]heptane-6-yl)-tert butoxycarbonylamino) propoxy)quinolin-4-yloxy)pyridin-2-yl)-2,3-dihydro-1,5-dimethyl-3-oxo-2-phenyl-1H-pyrazole-4-carboxamide

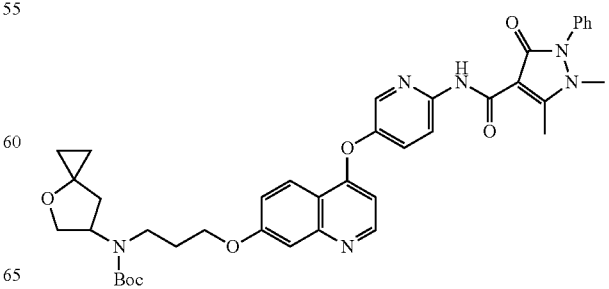

To a solution of N-(5-(7-hydroxyquinolin-4-yloxy)pyridin-2-yl)-2,3-dihydro-1,5-dimethyl-3-oxo-2-phenyl-1H-pyrazole-4-carboxamide (200.6 mg, 0.44 mmol) and cesium carbonate (684.6 mg, 2.1 mmol, Aladdin) in N,N-dimethylacetamide (1 mL) was added (N-(4-oxaspiro[2.4]heptane-6-yl)-tert butoxycarbonylamino)propyl methanesulfonate (0.63 mmol) in N,N-dimethylacetamide (5 mL). After stirring at 40° C. for 2 days, the reaction mixture was concentrated in vacuo. The residue was chromatographed with a silica gel column (1:4 (v/v) n-hexane/EtOAc) to give the title compound as a white solid (200 mg, 62.5%).

MS (ESI, pos. ion) m/z: 721.2 (M+1); LC-MS Rt: 4.669 min;

$^1$H NMR (400 MHz, CDCl$_3$): δ 0.55 (m, 1H), 0.65 (m, 1H), 0.78 (m, 1H), 0.93 (m, 1H), 1.49 (s, 9H), 2.09 (m, 2H), 2.18 (m, 3H), 2.81 (s, 3H), 3.38 (s, 3H), 3.45 (m, 2H), 3.78 (dd, J$_1$=5.6 Hz, J$_2$=14.8 Hz, 1H), 3.95 (m, 1H), 4.16 (t, 2H), 6.43 (d, J=5.6 Hz, 1H), 7.22 (dd, J$_1$=2.4 Hz, J$_2$=11.6 Hz, 1H), 7.38 (m, 3H), 7.51 (m, 4H), 8.23 (d, J=4.4 Hz, 1H), 8.24 (d, J=2 Hz, 1H), 8.38 (d, J=9.2 Hz, 1H), 8.60 (d, J=5.2 Hz, 1H), 11.26 (s, 1H).

Step 6) N-(5-(7-((4-oxaspiro[2.4]heptane-6-yl)aminopropoxy)quinolin-4-yloxy)pyridin-2-yl)-2,3-dihydro-1,5-dimethyl-3-oxo-2-phenyl-1H-pyrazole-4-carboxamide

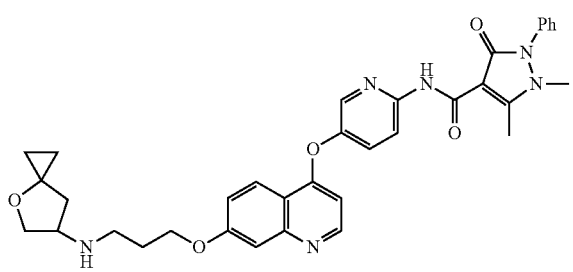 [SMILES: Cc1c(C(=O)Nc2ccc(Oc3ccnc4cc(OCCCNC5COC6(CC6)C5)ccc34)cn2)c(=O)n(-c2ccccc2)n1C]

To a solution of N-(5-(7-((N-(4-oxaspiro[2.4]heptane-6-yl)-tert butoxycarbonylamino)propoxy)quinolin-4-yloxy)pyridin-2-yl)-2,3-dihydro-1,5-dimethyl-3-oxo-2-phenyl-1H-pyrazole-4-carboxamide (50 mg, 0.069 mmol) in dry THF (2 mL) was added 2 M HCl/THF (8 mmol). After stirring at room temperature for 4 hrs, 10 mL of saturated NaHCO$_3$ aqueous solution was added to quench the reaction. The mixture was extracted with EtOAc (15 mL×2). The combined organic phases were dried over Na$_2$SO$_4$, concentrated in vacuo. The crude product was chromatographed with a silica gel column (5:1 (v/v) EtOAc/MeOH) to give the title compound as a white solid (30 mg, 69%).

MS (ESI, pos. ion) m/z: 621.2 (M+1); LC-MS Rt: 3.192 min;

$^1$H NMR (400 MHz, CDCl$_3$): δ 0.48 (m, 1H), 0.57 (m, 1H), 0.81 (m, 1H), 0.89 (m, 1H), 1.94 (dd, J$_1$=4 Hz, J$_2$=12 Hz, 1H), 2.12 (m, 2H), 2.24 (dd, J$_1$=7.2 Hz, J$_2$=20 Hz, 1H), 2.81 (s, 3H), 2.91 (t, 2H), 3.38 (s, 3H), 3.63 (d, J=6.4 Hz, 1H), 3.75 (dd, J$_1$=3.6 Hz, J$_2$=12.4 Hz, 1H), 4.00 (dd, J$_1$=6.0 Hz, J$_2$=14.8 Hz, 1H), 4.24 (t, 2H), 6.43 (d, J=5.2 Hz, 1H), 7.22 (dd, J=2.4 Hz, J=11.6 Hz, 1H), 7.38 (m, 3H), 7.51 (m, 4H), 8.23 (d, J=2.8 Hz, 1H), 8.24 (d, J=3.6 Hz, 1H), 8.38 (d, J=8.8 Hz, 1H), 8.60 (d, J=5.2 Hz, 1H), 11.26 (s, 1H).

Example 12

N-(5-(7-(3-(7-hydroxy-5-azaspiro[2.4]heptane-5-yl)propoxy)quinolin-4-yloxy)pyridin-2-yl)-2,3-dihydro-1,5-dimethyl-3-oxo-2-phenyl-1H-pyrazole-4-carboxamide

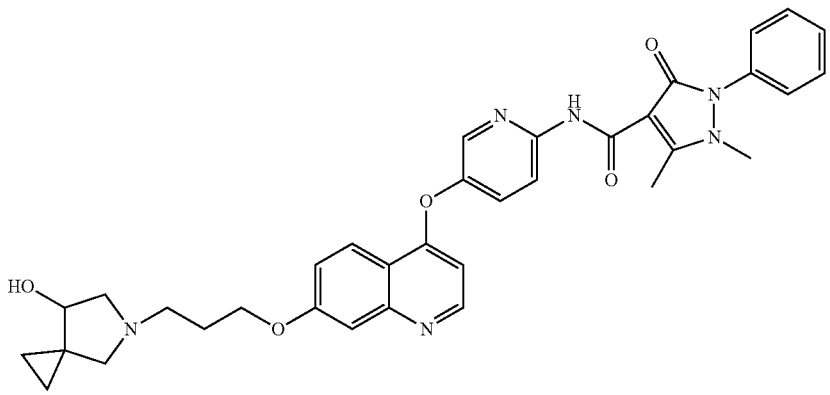 [SMILES: Cc1c(C(=O)Nc2ccc(Oc3ccnc4cc(OCCCN5CC(O)C6(CC6)C5)ccc34)cn2)c(=O)n(-c2ccccc2)n1C]

Step 1) ethyl 1-acetylcyclopropanecarboxylate

To a solution of ethyl 3-oxobutanoate (26 g, 200 mmol) in acetone (500 mL) was added potassium carbonate (82.8 g, 600 mmol) followed by 1,2-dibromoethane (45.12 g, 240 mmol). The reaction was refluxed for 24 hrs, then the reaction mixture was filtered. The filtrate was concentrated in vacuo, and the residue was purified by a silica gel column chromatography (1:50(v/v) EtOAc/n-hexane) to afford the title compound as colorless oil (18.7 g, 60%).

MS (ESI, pos. ion) m/z: 157 (M+1);
$^1$H NMR (400 MHz, CDCl$_3$): δ 1.25-1.29 (t, J=7.2 Hz, 3H), 1.45 (s, 4H), 2.45 (s, 3H), 4.18-4.20 (q, 2H).

Step 2) ethyl 1-(2-bromoacetyl)cyclopropanecarboxylate

To a 100 mL of round-bottomed flask was added ethyl 1-acetylcyclopropanecarboxylate (15.6 g, 100 mmol) and NBS solid (21.36 g, 120 mmol), followed by p-toluene sulfonic acid (1.9 g, 10 mmol). After stirring at rt for 8 hrs, the reaction mixture was extracted with diethyl ether (200 mL) and washed with 80 mL of water. The organic phase was then dried over anhydrous Na$_2$SO$_4$ and concentrated in vacuo. The residue was purified by a silica gel column chromatography (1:30(v/v) EtOAc/n-hexane) to give the title compound as colorless oil (16.68 g, 71%).

MS (ESI, pos. ion) m/z: 235, 237 (M+1);
$^1$H NMR (400 MHz, CDCl$_3$): δ 1.27 (t, J=7.2 Hz, 3H), 1.59-1.64 (m, 4H), 4.19-4.24 (q, J$_1$=14.4 Hz, J$_2$=7.2 Hz, 2H), 4.49 (s, 2H).

Step 3) 5-((R)-α-methylbenzyl)-4,7-dioxo-5-azaspiro[2.4]heptane

To a solution of ethyl 1-(2-bromoacetyl)cyclopropanecarboxylate (4.7 g, 20 mmol) in THF (60 mL) was added (R)-α-methylbenzylamine (2.9 g, 24 mmol) and Et$_3$N (4.04 g, 40 mmol). After stirring at rt for 3 days, the reaction mixture was concentrated in vacuo, and the residue was extracted with ethyl acetate (50 mL×2) and washed with water (30 mL). The combined organic phases were dried over anhydrous Na$_2$SO$_4$, filtered and the filtrate was concentrated in vacuo. The residue was purified by a silica gel column chromatography (EtOAc) to afford the title compound as a light yellow solid (3.66 g, 80%).

MS (ESI, pos. ion) m/z: 230 (M+1);
$^1$H NMR (400 MHz, CDCl$_3$): δ 1.58-1.60 (m, 4H), 1.62-1.63 (d, J=5.6 Hz, 3H), 3.49-3.53 (d, J=17.6 Hz, 1H), 3.83-3.88 (d, J=17.6 Hz, 1H), 5.80-5.82 (q, 1H), 7.26-7.39 (m, 5H).

Step 4) 5((R)-α-methylbenzyl)-7-hydroxy-5-azaspiro[2.4]heptane

To a suspension of LiAlH$_4$ (0.995 g, 26.2 mmol) in THF (40 mL) was added a solution of 5-((R)-α-methylbenzyl)-4,7-dioxo-5-azaspiro[2.4]heptane (3.0 g, 13.1 mmol) in THF (10 mL) at 0° C. The reaction mixture was stirred at 0° C. for 2 hrs, then warmed up to 50° C. and continued to stir for 6 hrs. The reaction mixture was then cooled to 0° C. and ethyl acetate (10 mL) and water (10 mL) were added. The suspension was filtered and the filtrate was concentrated in vacuo. The residue was purified by a silica gel column chromatography (1:3 (v/v) 2-butanol/n-hexane) to afford the title compound as colorless oil (2.4 g, 85%).

MS (ESI, pos. ion) m/z: 218 (M+1);

Step 5) 7-hydroxy-5-azaspiro[2.4]heptane

To a solution of 5((R)-α-methylbenzyl)-7-hydroxy-5-azaspiro[2.4]heptane (2.4 g, 11.1 mmol) in ethanol (30 mL) was added the catalytic amount of Pd/C. The suspension was then stirred under H$_2$ for 3 hrs. The suspension was filtered and the filtrate was concentrated in vacuo to afford the desired compound as light orange oil (1.23 g, 98%). The crude product was used for the next step without further purification.

MS (ESI, pos. ion) m/z: 114 (M+1);

Step 6) 3-(7-hydroxy-5-azaspiro[2.4]heptane-5-yl)propanol

To a solution of 7-hydroxy-5-azaspiro[2.4]heptane (1.23 g, 11.0 mmol) in THF (40 mL) was added 3-bromopropanol (2.3 g, 16.65 mmol) and Et$_3$N (2.24 g, 22.2 mmol). The reaction mixture was stirred at rt for 12 hrs and then concentrated in vacuo. The residue was purified by a silica gel column chromatography (100:50:2(v/v/v) EtOAc/CH$_3$OH/Et$_3$N) to afford the desired compound as orange oil (1.14 g, 60%).

MS (ESI, pos. ion) m/z: 172 (M+1); LC-MS Rt: 0.178 min;
$^1$H NMR (400 MHz, CDCl$_3$): δ 0.59 (m, 1H), 0.62 (m, 1H), 0.70-0.72 (m, 1H), 0.87-0.92 (m, 1H), 1.68-1.74 (m, 2H), 2.39-2.41 (d, J=9.2 Hz, 1H), 2.70-2.74 (m, 2H), 2.84-2.87 (m, 2H), 2.88-2.92 (dd, J$_1$=10.4 Hz, J$_2$=4.8 Hz, 1H), 3.73-3.75 (m, 1H), 3.77-3.80 (t, J=5.2 Hz, 2H);

Step 7) 3-(7-hydroxy-5-azaspiro[2.4]heptane-5-yl)propyl methanesulfonate

To a solution of 3-(7-hydroxy-5-azaspiro[2.4]heptane-5-yl)propanol (1.14 g, 6.67 mmol) and Et$_3$N (1.35 g, 13.34 mmol) in CH$_2$Cl$_2$ (20 mL) was added methanesulfonyl chloride (1.15 g, 10 mmol) dropwise at 0° C. The reaction was then stirred at 0° C. for 3 hrs. The reaction mixture was washed with cold water (10 mL) and the organic layer was dried over anhydrous Na$_2$SO$_4$, filtered and concentrated in vacuo to afford the title compound as orange oil. The crude product was used for the next step without further purification.

Step 8) N-(5-(7-(3-(7-hydroxy-5-azaspiro[2.4]heptane-5-yl)propoxy)quinolin-4-yloxy)pyridin-2-yl)-2,3-dihydro-1,5-dimethyl-3-oxo-2-phenyl-1H-pyrazole-4-carboxamide

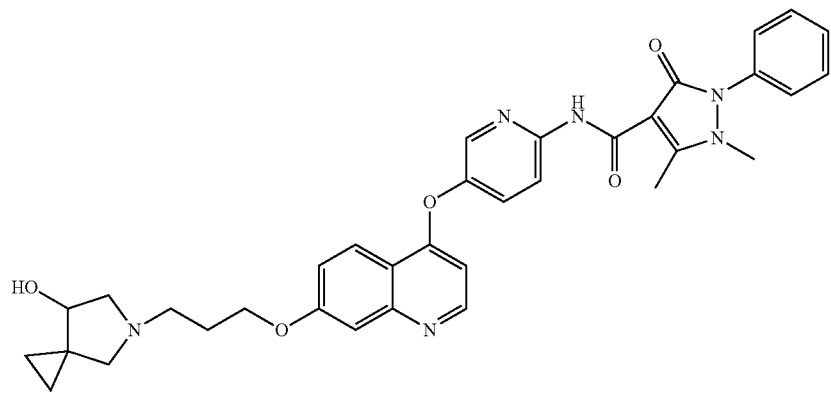 [SMILES: Cc1c(C(=O)Nc2ccc(Oc3ccnc4cc(OCCCN5CC(O)C6(CC6)C5)ccc34)cn2)c(=O)n(-c2ccccc2)n1C]

To a solution of N-(5-(7-hydroxyquinolin-4-yloxy)pyridin-2-yl)-1,5-dimethyl-3-oxo-2-phenyl-2,3-dihydro-1H-pyrazole-4-carboxamide (300 mg, 0.642 mmol) in DMA (3 mL) was added 3-(7-hydroxy-5-azaspiro[2.4]heptane-5-yl)propyl methanesulfonate (240 mg, 0.963 mmol) and $Cs_2CO_3$ (417 mg, 1.284 mmol). The reaction was stirred at rt for 24 hrs. The solvent was removed and the residue was partioned between saturated $NaHCO_3$ aqueous solution (15 mL) and $CHCl_3$ (30 mL). The organic layer was separated, dried over anhydrous $Na_2SO_4$, filtered and concentrated in vacuo. The residue was purified by a silica gel column chromatography (100:15:1(v/v/v) $EtOAc/CH_3OH/Et_3N$) to afford the title compound as a white solid (259 mg, 65%).

MS (ESI, pos. ion) m/z: 621 (M+1); LC-MS Rt: 3.209 min; $^1$H NMR (400 MHz, $CDCl_3$): δ 0.63 (m, 1H), 0.67 (m, 1H), 0.76-0.79 (m, 1H), 0.96-0.99 (m, 1H), 2.11-2.14 (m, 2H), 2.47-2.50 (d, J=8.4 Hz, 1H), 2.80 (s, 3H), 3.00-3.03 (d, J=9.6 Hz, 1H), 3.06-3.08 (d, J=10.4 Hz, 1H), 3.37 (s, 5H), 3.76-3.77 (d, J=3.6 Hz, 1H), 4.23-4.24 (m, 2H), 6.42-6.43 (d, J=5.2 Hz, 1H), 7.20-7.23 (d, J=8.8 Hz, 1H), 7.36-7.38 (d, J=7.6 Hz, 2H), 7.47-7.49 (m, 5H), 7.53-7.57 (m, 2H), 8.22-8.24 (d, J=8.4 Hz, 2H), 8.37-8.39 (d, J=9.2 Hz, 1H), 8.58-8.59 (d, J=4.8 Hz, 1H), 11.25 (s, 1H)

Example 13

N-(4-(7-(3-(7-hydroxy-5-azaspiro[2.4]heptane-5-yl)propoxy)quinolin-4-yloxy)-3-fluorophenyl)-N-phenylcyclopropane-1,1-dicarboxamide

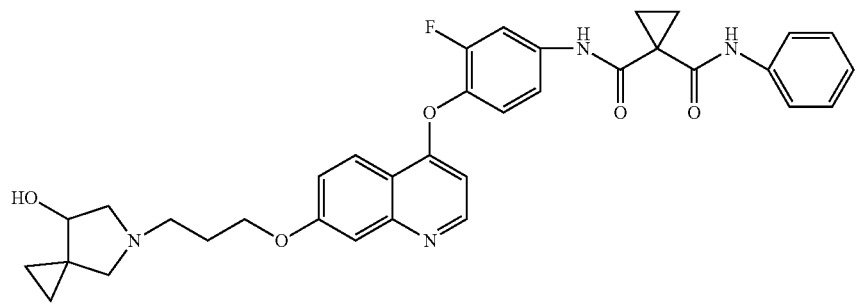 [SMILES: O=C(Nc1ccccc1)C1(C(=O)Nc2ccc(Oc3ccnc4cc(OCCCN5CC(O)C6(CC6)C5)ccc34)c(F)c2)CC1]

To a solution of N-(3-fluoro-4-(7-hydroxyquinolin-4-yloxy)phenyl)-N-phenylcyclopropane-1,1-dicarboxamide (240 mg, 0.525 mmol) in DMA (3 mL) was added 3-(7-hydroxy-5-azaspiro[2.4]heptane-5-yl)propyl methanesulfonate (261 mg, 1.05 mmol) and $Cs_2CO_3$ (512 mg, 1.575 mmol). The reaction was then stirred at rt for 24 hrs. The solvent was removed and the residue was partioned between saturated $NaHCO_3$ (10 mL) aqueous solution and $CHCl_3$ (30 mL). The organic layer was separated, dried over anhydrous $Na_2SO_4$, filtered and concentrated in vacuo. The residue was purified by a silica gel column chromatography (100:15:1(v/v/v) $EtOAc/CH_3OH/Et_3N$) to afford the desired compound as a white solid (170 mg, 53%).

MS (ESI, pos. ion) m/z: 611 (M+1);
$^1$H NMR (400 MHz, $CDCl_3$): δ 0.59-0.60 (m, 1H), 0.62-0.65 (m, 1H), 0.73-0.78 (m, 1H), 0.92-0.96 (m, 1H), 1.58-1.62 (q, $J_1$=8.0 Hz, $J_2$=4.4 Hz, 2H), 1.81-1.84 (m, 2H), 2.05-2.88 (m, 2H), 2.38-2.40 (d, J=8.4 Hz, 1H), 2.68-2.73 (m, 2H), 2.81-2.85 (dd, $J_1$=4.8 Hz, $J_2$=4.4 Hz, 1H), 2.90-2.92 (d, J=8.8 Hz, 1H), 2.96-2.98 (d, J=9.2 Hz, 1H), 3.74-3.73 (d, J=3.6 Hz, 1H), 4.21-4.26 (m, 2H), 6.36-6.38 (d, J=5.2 Hz, 1H), 7.18-7.24 (m, 2H), 7.26-7.29 (d, J=10.4 Hz, 1H), 7.36-7.40 (t, J=8 Hz, 2H), 7.48-7.51 (m, 2H), 7.75-7.79 (dd, $J_1$=2 Hz, $J_2$=2.4 Hz, 1H), 8.05 (s, 1H), 8.24-8.26 (d, J=9.2 Hz, 1H), 8.56-8.58 (d, J=5.2 Hz, 1H), 10.19 (s, 1H).

Example 14

N-(4-(7-(3-(7-hydroxy-5-azaspiro[2.4]heptane-5-yl)propoxy)quinolin-4-yloxy)-3-fluorophenyl)-2,3-dihydro-1,5-dimethyl-3-oxo-2-phenyl-1H-pyrazole-4-carboxamide

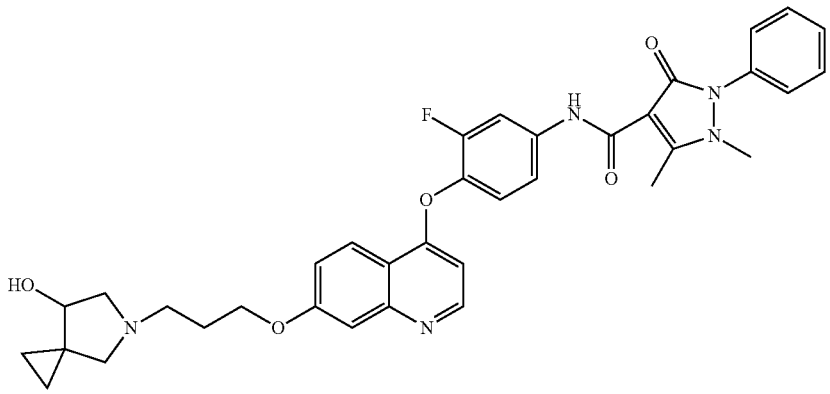 [SMILES: Cc1c(C(=O)Nc2ccc(Oc3ccnc4cc(OCCCN5CC(O)C6(CC6)C5)ccc34)c(F)c2)c(=O)n(-c2ccccc2)n1C]

To a solution of N-(3-fluoro-4-(7-hydroxyquinolin-4-yloxy)phenyl)-1,5-dimethyl-3-oxo-2-phenyl-2,3-dihydro-1H-pyrazole-4-carboxamide (200 mg, 0.413 mmol) in DMA (3 mL) was added 3-(7-hydroxy-5-azaspiro[2.4]heptane-5-yl)propyl methanesulfonate (154 mg, 0.619 mmol) and $Cs_2CO_3$ (268 mg, 0.826 mmol). The reaction was then stirred at rt for 40 hrs. The solvent was removed and the residue was partioned between saturated $NaHCO_3$ aqueous solution (10 mL) and $CHCl_3$ (25 mL). The organic layer was dried over anhydrous $Na_2SO_4$, filtered and concentrated in vacuo. The residue was purified by a silica gel column chromatography (100:15:1(v/v/v) $EtOAc/CH_3OH/Et_3N$) to afford a pale yellow solid (192 mg, 73%).

MS (ESI, pos. ion) m/z: 638 (M+1); LC-MS Rt: 3.140 min;
$^1$H NMR (400 MHz, $CDCl_3$): δ 0.63-0.65 (m, 1H), 0.67-0.69 (m, 1H), 0.76-0.81 (m, 1H), 0.98-1.02 (m, 1H), 2.08-2.17 (m, 2H), 2.54-2.57 (d, J=9.2 Hz, 1H), 2.80 (s, 3H), 2.81 (m, 2H), 2.98-3.02 (dd, $J_1$=4.8 Hz, $J_2$=4.4 Hz, 1H), 3.08-3.10 (d, J=9.2 Hz, 1H), 3.12-3.14 (d, J=9.6 Hz, 1H), 3.38 (s, 3H), 3.79-3.80 (d, J=4.8 Hz, 1H), 4.21-4.25 (m, 2H), 6.40-6.42 (d, J=5.2 Hz, 1H), 7.14-7.17 (d, J=8.4 Hz, 1H), 7.19-7.22 (dd, $J_1$=9.6 Hz, $J_2$=2.4 Hz, 1H), 7.29-7.31 (d, J=4.8 Hz, 1H), 7.36-7.37 (d, J=6 Hz, 2H), 7.47-7.50 (m, 2H), 7.55-7.59 (q, J=7.6 Hz, 2H), 7.90-7.94 (dd, $J_1$=12.4 Hz, $J_2$=2.4 Hz, 1H), 8.25-8.28 (d, J=9.2 Hz, 1H), 8.57-8.58 (d, J=9.2 Hz, 1H), 10.883 (s, 1H).

Example 15

N-(4-(7-(3-(7-hydroxy-5-azaspiro[2.4]heptane-5-yl)propoxy)-6-methoxyquinolin-4-yloxy)-3-fluorophenyl)-2,3-dihydro-1,5-dimethyl-3-oxo-2-phenyl-1H-pyrazole-4-carboxamide

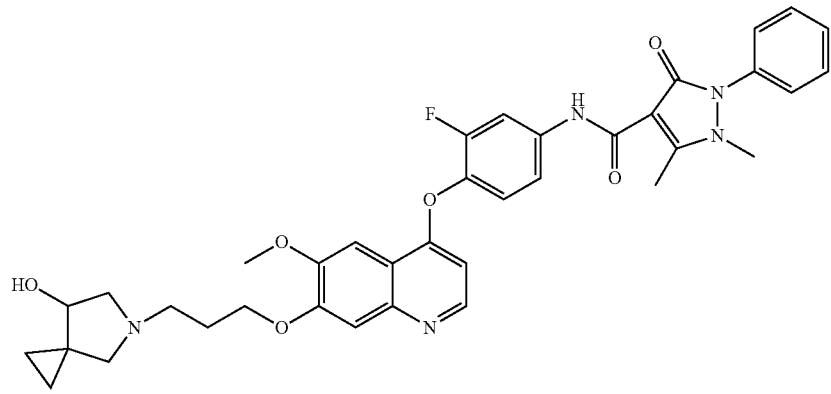 [SMILES: COc1cc2c(Oc3ccc(NC(=O)c4c(C)n(C)n(-c5ccccc5)c4=O)cc3F)ccnc2cc1OCCCN1CC(O)C2(CC2)C1]

To a solution of N-(3-fluoro-4-(7-hydroxy-6-methoxyquinolin-4-yloxy)phenyl)-1,5-dimethyl-3-oxo-2-phenyl-2,3-dihydro-1H-pyrazole-4-carboxamide (200 mg, 0.389 mmol) in DMA (2 mL) was added 3-(7-hydroxy-5-azaspiro[2.4]heptane-5-yl)propyl methanesulfonate (193 mg, 0.778 mmol) and $Cs_2CO_3$ (379 mg, 1.167 mmol). The reaction was then stirred at rt for 40 hrs. The solvent was removed and the residue was partioned between saturated $NaHCO_3$ aqueous solution (10 mL) and $CHCl_3$ (30 mL). The organic layer was separated, dried over anhydrous $Na_2SO_4$, filtered and concentrated in vacuo and the residue was purified by a silica gel column chromatography (100:15:1 (v/v/v) EtOAc/$CH_3OH$/$Et_3N$) to afford the desired compound as a pale yellow solid (171 mg, 66%).

MS (ESI, pos. ion) m/z: 668 (M+1); LC-MS Rt: 3.421 min;
$^1$H NMR (400 MHz, $CDCl_3$): δ 0.72-0.77 (m, 2H), 0.82-0.85 (m, 1H), 1.08-1.12 (m, 1H), 2.35-2.38 (m, 2H), 2.75 (m, 2H), 2.80 (s, 3H), 2.83-2.86 (d, J=6 Hz, 1H), 3.17-3.18 (m, 1H), 3.38 (s, 3H), 3.41-3.46 (t, J=10 Hz, 2H), 3.86-3.88 (d, J=4.8 Hz, 1H), 4.02 (s, 3H), 4.30 (m, 2H), 6.43-6.44 (d, J=5.2 Hz, 1H), 7.15-7.19 (t, J=8.8 Hz, 1H), 7.29-7.31 (d, J=8.8 Hz, 1H), 7.35-7.37 (d, J=7.2 Hz, 2H), 7.46-7.50 (m, 2H), 7.55-7.59 (m, 3H), 7.90-7.94 (dd, $J_1$=8.8 Hz, $J_2$=8.8 Hz, 1H), 8.45-8.47 (d, J=5.2 Hz, 1H), 10.89 (s, 1H).

Example 16

N-(5-(7-(3-(7-hydroxy-5-azaspiro[2.4]heptane-5-yl)propoxy)quinolin-4-yloxy)pyridin-2-yl)-N-phenylcyclopropane-1,1-dicarboxamide

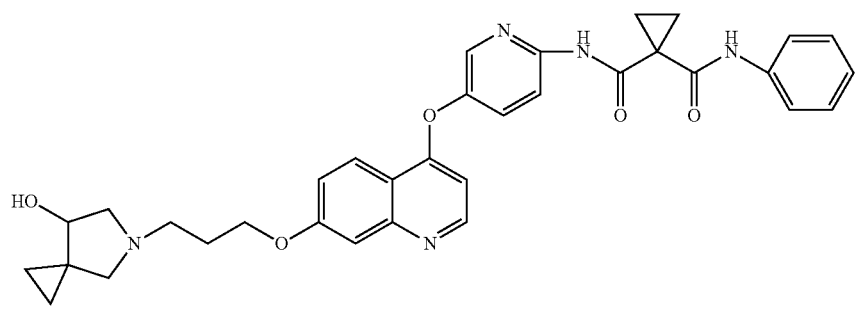 [SMILES: O=C(Nc1ccccc1)C1(C(=O)Nc2ccc(Oc3ccnc4cc(OCCCN5CC(O)C6(CC6)C5)ccc34)cn2)CC1]

To a solution of N-(5-(7-hydroxyquinolin-4-yloxy)pyridin-2-yl)-N-phenylcyclopropane-1,1-dicarboxamide (110 mg, 0.25 mmol) in DMA (2 mL) was added 3-(7-hydroxy-5-azaspiro[2.4]heptane-5-yl)propyl methanesulfonate (125 mg, 0.50 mmol) and Cs$_2$CO$_3$ (243 mg, 0.75 mmol). The reaction was then stirred at rt for 24 hrs. The solvent was removed and the residue was partoned between saturated NaHCO$_3$ aqueous solution (10 mL) and CHCl$_3$ (30 mL). The organic layer was separated, dried over anhydrous Na$_2$SO$_4$, filtered and the filtrate was concentrated in vacuo. The residue was purified by a silica gel column chromatography (100:15:1(v/v/v) EtOAc/CH$_3$OH/Et$_3$N) to afford the desired compound as a pale yellow solid (110 mg, 75%).

MS (ESI, pos. ion) m/z: 594 (M+1);

$^1$H NMR (400 MHz, CDCl$_3$): δ 0.55 (m, 1H), 0.62 (m, 1H), 0.77 (m, 1H), 0.92-0.96 (m, 1H), 1.66-1.69 (q, J$_1$=7.2 Hz, J$_2$=8.4 Hz, J$_3$=4.4 Hz, J$_4$=5.6 Hz, 2H), 1.78-1.81 (q, J$_1$=7.2 Hz, J$_2$=8.4 Hz, J$_3$=4.4 Hz, J$_4$=5.6 Hz, 2H), 2.04-2.09 (m, 2H), 2.36-2.38 (d, J=8.8 Hz, 1H), 2.66-2.72 (m, 2H), 2.79-2.83 (dd, J$_1$=J$_2$=10 Hz, J$_3$=J$_4$=4.8 Hz, 1H), 2.87-2.89 (d, J=8.8 Hz, 1H), 2.93-2.95 (d, J=9.6 Hz, 1H), 3.73-3.74 (d, J=4.4 Hz, 1H), 4.19-4.25 (m, 2H), 6.38-6.40 (d, J=5.2 Hz, 1H), 7.11-7.15 (t, J$_1$=8.8 Hz, J$_2$=7.2 Hz, 1H), 7.21-7.24 (dd, J$_1$=J$_2$=9.2 Hz, J$_3$=J$_4$=2.8 Hz, 1H), 7.31-7.35 (t, J$_1$=J$_2$=7.2 Hz, 2H), 7.50-7.51 (d, J=2.8 Hz, 1H), 7.55-7.58 (m, 3H), 8.18-8.21 (d, J=9.2 Hz, 1H), 8.23-8.23 (d, J=2.4 Hz, 1H), 8.27-8.29 (d, J=9.2 Hz, 1H), 8.58-8.59 (d, J=5.2 Hz, 1H).

Example 17

N-(4-(7-(3-(7-hydroxy-5-azaspiro[2.4]heptane-5-yl)propoxy)-6-methoxyquinolin-4-yloxy)-3-fluorophenyl)-N-phenylcyclopropane-1,1-dicarboxamide To a solution of N-(3-fluoro-4-(7-hydroxy-6-methoxyquinolin-4-yloxy)phenyl)-N-phenylcyclopropane-1,1-dicarboxamide (260 mg, 0.534 mmol) in DMA (3 mL) was added 3-(7-hydroxy-5-azaspiro[2.4]heptane-5-yl)propyl methanesulfonate (266 mg, 1.068 mmol) and Cs$_2$CO$_3$ (520 mg, 1.602 mmol). The reaction was then stirred at rt for 2 days. The solvent was removed and the residue was partioned between saturated NaHCO$_3$ aqueous solution (15 mL) and CHCl$_3$ (30 mL). The organic layer was dried over anhydrous Na$_2$SO$_4$, filtered and the filtrate was concentrated in vacuo. The residue was purified by a silica gel column chromatography (100:15:1(v/v/v) EtOAc/CH$_3$OH/Et$_3$N) to afford the desired compound as a pale yellow solid (264 mg, 77%).

MS (ESI, pos. ion) m/z: 641 (M+1); LC-MS Rt: 3.439 min;

$^1$H NMR (400 MHz, CDCl$_3$): δ 0.61 (m, 2H), 0.75 (m, 1H), 0.96 (m, 1H), 1.59-1.62 (q, J$_1$=7.2 Hz, J$_2$=8 Hz, J$_3$=4.4 Hz, J$_4$=5.2 Hz, 2H), 1.81-1.84 (q, J$_1$=7.6 Hz, J$_2$=8.4 Hz, J$_3$=4.4 Hz, J$_4$=5.2 Hz, 2H), 2.07-2.15 (m, 2H), 2.36-2.38 (d, J=8.8 Hz, 1H), 2.64-2.73 (m, 2H), 2.76-2.80 (dd, J$_1$=9.6 Hz, J$_2$=9.2 Hz, J$_3$=4.4 Hz, J$_4$=4.8 Hz, 1H), 2.92-2.94 (d, J=8.8 Hz, 1H), 2.99-3.02 (d, J=10 Hz, 1H), 3.73-3.74 (d, J=3.6 Hz, 1H), 4.041 (s, 3H), 4.30-4.32 (m, 2H), 6.38-6.39 (d, J=5.2 Hz, 1H), 7.19-7.23 (t, J$_1$=8.8 Hz, J$_2$=8 Hz, 1H), 7.30-7.30 (d, J=6.4 Hz, 1H), 7.36-7.40 (t, J$_1$=8.4 Hz, J$_2$=7.6 Hz, 2H), 7.48-7.50 (d, J=9.6 Hz, 2H), 7.56 (s, 1H), 7.70 (s, 1H), 7.76-7.80 (dd, J$_1$=J$_2$=12 Hz, J$_3$=J$_4$=2.4 Hz, 1H), 8.15 (s, 1H), 8.45-8.46 (d, J=5.2 Hz, 1H), 10.24 (s, 1H).

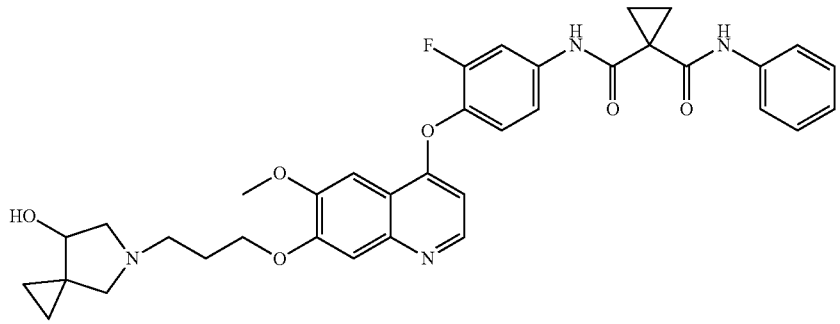 [SMILES: COc1cc2c(Oc3ccc(NC(=O)C4(C(=O)Nc5ccccc5)CC4)cc3F)ccnc2cc1OCCCN1CC(O)C2(CC2)C1]

Example 18

N-(4-(7-(3-(7-hydroxy-5-azaspiro[2.4]heptane-5-yl)propoxy)-6-methoxyquinolin-4-yloxy)-3-fluorophenyl)-N-(4-fluorophenyl)cyclopropane-1,1-dicarboxamide

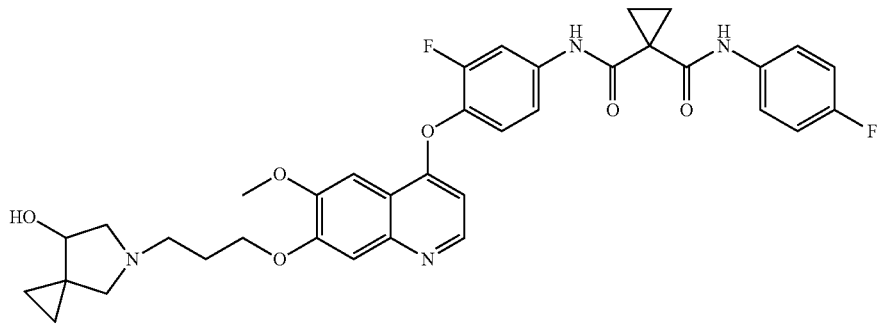 [SMILES: COc1cc2c(Oc3ccc(NC(=O)C4(C(=O)Nc5ccc(F)cc5)CC4)cc3F)ccnc2cc1OCCCN1CC(O)C2(CC2)C1]

To a solution of N-(3-fluoro-4-(7-hydroxy-6-methoxyquinolin-4-yloxy)phenyl)-N-(4-fluorophenyl)cyclopropane-1,1-dicarboxamide (240 mg, 0.475 mmol) in DMA (3 mL) was added 3-(7-hydroxy-5-azaspiro[2.4]heptane-5-yl)propyl methanesulfonate (236 mg, 0.95 mmol) and $Cs_2CO_3$ (463 mg, 1.425 mmol). The reaction was then stirred at rt for 2 days. The solvent was removed and the residue was partioned between saturated $NaHCO_3$ aqueous solution (15 mL) and $CHCl_3$ (30 mL). The organic layer was separated, dried over anhydrous $Na_2SO_4$, filtered and the filtrate was concentrated in vacuo. The residue was purified by a silica gel column chromatography (100:15:1(v/v/v) EtOAc/$CH_3OH$/$Et_3N$) to afford the desired compound as a white solid (250 mg, 80%).

MS (ESI, pos. ion) m/z: 659 (M+1);
$^1$H NMR (400 MHz, $CDCl_3$): δ 0.58-0.66 (m, 2H), 0.74-0.78 (m, 1H), 0.95-1.00 (m, 1H), 1.62-1.65 (q, $J_1$=7.6 Hz, $J_2$=8.4 Hz, $J_3$=4.4 Hz, $J_4$=5.2 Hz, 2H), 1.79-1.82 (q, $J_1$=7.2 Hz, $J_2$=8.4 Hz, $J_3$=4.4 Hz, $J_4$=5.6 Hz, 2H), 2.05-2.16 (m, 2H), 2.39-2.42 (d, J=8.8 Hz, 1H), 2.68-2.77 (m, 2H), 2.80-2.83 (dd, $J_1$=$J_2$=10 Hz, $J_3$=$J_4$=4.8 Hz, 1H), 2.96-2.98 (d, J=8.8 Hz, 1H), 3.03-3.05 (d, J=10 Hz, 1H), 3.74-3.75 (d, J=3.6 Hz, 1H), 4.04 (s, 3H), 4.30-4.31 (m, 2H), 6.38-6.39 (d, J=5.6 Hz, 1H), 7.05-7.08 (d, J=6.4 Hz, 2H), 7.19-7.23 (t, $J_1$=$J_2$=8.4 Hz, 1H), 7.27-7.29 (d, J=9.6 Hz, 1H), 7.41-7.47 (q, $J_1$=$J_2$=6.8 Hz, $J_3$=$J_4$=4.8 Hz, 1H), 7.56 (s, 1H), 7.69 (s, 1H), 7.75-7.78 (dd, $J_1$=$J_2$=12 Hz, $J_3$=$J_4$=2.4 Hz, 1H), 8.38 (s, 1H), 8.44-8.46 (d, J=5.6 Hz, 1H).

Example 19

N-(5-(7-(3-(7-hydroxy-5-azaspiro[2.4]heptane-5-yl)propoxy)-6-methoxyquinolin-4-yloxy)pyridin-2-yl)-2,3-dihydro-1,5-dimethyl-3-oxo-2-phenyl-1H-pyrazole-4-carboxamide

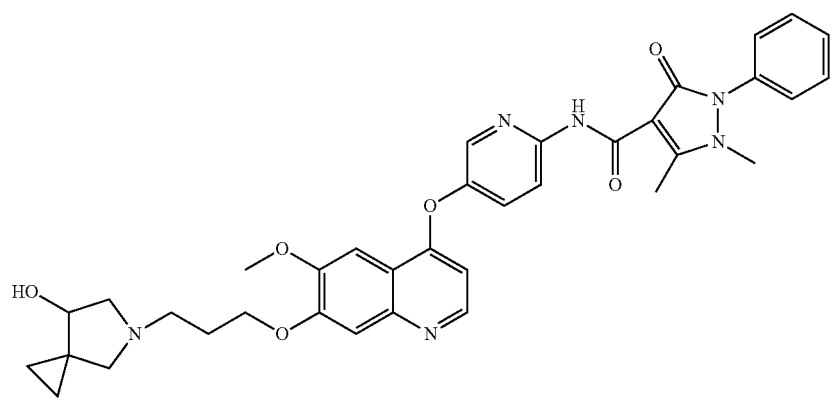 [SMILES: COc1cc2c(Oc3ccc(NC(=O)c4c(C)n(C)n(-c5ccccc5)c4=O)nc3)ccnc2cc1OCCCN1CC(O)C2(CC2)C1]

To a solution of N-(5-(7-hydroxy-6-methoxyquinolin-4-yloxy)pyridin-2-yl)-1,5-dimethyl-3-oxo-2-phenyl-2,3-dihydro-1H-pyrazole-4-carboxamide (200 mg, 0.402 mmol) in DMA (4 mL) was added 3-(7-hydroxy-5-azaspiro[2.4]heptane-5-yl)propyl methanesulfonate (150 mg, 0.603 mmol) and Cs$_2$CO$_3$ (261 mg, 0.804 mmol). The reaction was then stirred at rt for 24 hrs. The solvent was removed and the residue was partioned between saturated NaHCO$_3$ aqueous solution (5 mL) and CHCl$_3$ (25 mL). The organic layer was separated, dried over anhydrous Na$_2$SO$_4$, filtered and the filtrate was concentrated in vacuo. The residue was purified by a silica gel column chromatography (100:15:1 (v/v/v) EtOAc/CH$_3$OH/Et$_3$N) to afford the desired compound as a pale yellow solid (165 mg, 63%).

MS (ESI, pos. ion) m/z: 651 (M+1); LC-MS Rt: 3.296 min;
$^1$H NMR (400 MHz, CDCl$_3$): δ 0.78 (m, 1H), 0.79 (m, 1H), 0.86 (m, 1H), 0.90 (m, 1H), 1.10 (s, 3H), 1.37 (m, 2H), 1.40 (s, 2H), 1.43 (s, 2H), 2.80 (d, 3H), 3.14 (m, 2H), 3.38 (s, 3H), 4.02 (s, 3H), 4.29 (s, 1H), 6.46 (d, J=5.2 Hz, 1H), 7.36-7.39 (d, 2H), 7.46-7.57 (m, 6H), 8.24 (d, J=2.8 Hz, 1H), 8.38 (d, J=9.2 Hz, 1H), 8.49 (d, J=5.2 Hz, 1H), 11.28 (s, 1H).

Example 20

N-(5-(7-(3-(7-hydroxy-5-azaspiro[2.4]heptane-5-yl)propoxy)-6-methoxyquinolin-4-yloxy)pyridin-2-yl)-N-phenylcyclopropane-1,1-dicarboxamide

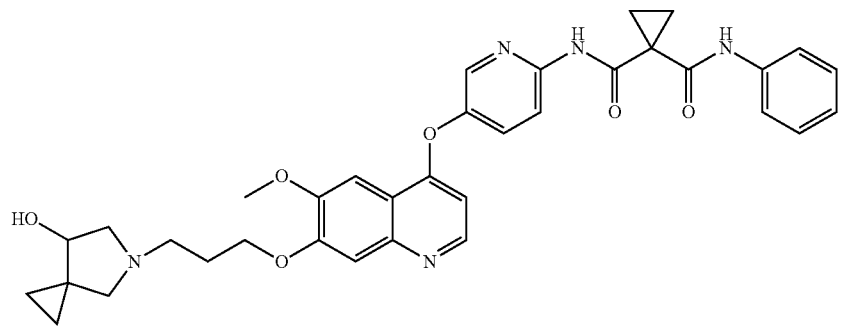 [SMILES: COc1cc2c(Oc3ccc(NC(=O)C4(C(=O)Nc5ccccc5)CC4)nc3)ccnc2cc1OCCCN1CC(O)C2(CC2)C1]

To a solution of N-(5-(7-hydroxy-6-methoxyquinolin-4-yloxy)pyridin-2-yl)-1,5-dimethyl-3-oxo-2-phenyl-2,3-dihydro-1H-pyrazole-4-carboxamide (300 mg, 0.640 mmol) in DMA (4 mL) was added 3-(7-hydroxy-5-azaspiro[2.4]heptane-5-yl)propyl methanesulfonate (239 mg, 0.960 mmol) and Cs$_2$CO$_3$ (416 mg, 1.280 mmol). The reaction was then stirred at rt for 48 hrs. The solvent was removed and the residue was partioned between saturated NaHCO$_3$ aqueous solution (5 mL) and CHCl$_3$ (25 mL). The organic layer was separated, dried over anhydrous Na$_2$SO$_4$, filtered and the filtrate was concentrated in vacuo. The residue was purified by a silica gel column chromatography (100:15:1 (v/v/v) EtOAc/CH$_3$OH/Et$_3$N) to afford the desired compound as a pale yellow solid (240 mg, 60%).

MS (ESI, pos. ion) m/z: 624 (M+1);
$^1$H NMR (400 MHz, CDCl$_3$): δ 0.71 (m, 2H), 0.85 (m, 2H), 1.25 (m, 2H), 1.42 (m, 2H), 1.69 (m, 2H), 1.79 (m, 2H), 2.23 (m, 2H), 3.12 (dd, 1H), 3.25 (m, 2H), 3.82 (d, 1H), 4.03 (s, 3H), 4.32 (m, 2H), 6.42 (d, J=5.2 Hz, 1H), 7.15 (t, J$_1$=8.8 Hz, J$_2$=7.2 Hz, 1H), 7.30 (dd, J$_1$=J$_2$=9.2 Hz, J$_3$=J$_4$=2.8 Hz, 1H), 7.37 (t, J$_1$=J$_2$=7.2 Hz, 2H), 7.52 (d, J=2.8 Hz, 1H), 7.56 (m, 4H), 8.30 (d, J=9.2 Hz, 1H), 8.49-8.23 (d, J=2.4 Hz, 1H), 9.41 (s, 1H).

Example 21

N-(4-(7-(4-oxaspiro[2.4]heptane-6-yloxy)quinolin-4-yloxy)-3-fluorophenyl)-N-phenylcyclopropane-1,1-dicarboxamide

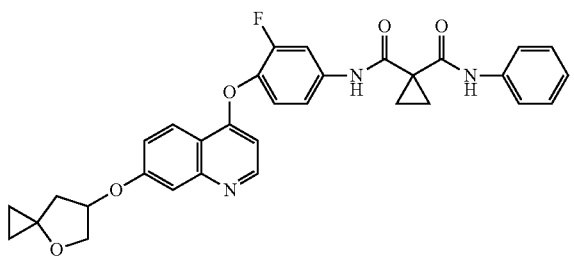 [SMILES: O=C(Nc1ccccc1)C1(C(=O)Nc2ccc(Oc3ccnc4cc(OC5COC6(CC6)C5)ccc34)c(F)c2)CC1]

Step 1) diethyl cyclopropane-1,1-dicarboxylate

To a solution of diethyl malonate (3.2 g, 20 mmol) and anhydrous potassium carbonate powder (6.9 g, 50 mmol) in DMF (50.0 mL) was added 1,2-dibromoethane (4.136 g, 22 mmol). After stirring for 2 hrs, catalytic amount of TBAI (0.738 g, 2.0 mmol) was added and the mixture was continued to stir at room temperature for 8 hrs. The reaction mixture was filtered and the solid was washed with diethyl ether 3 times. The filtrate was diluted with water (200 mL) and extracted with diethyl ether (75 mL×4). The combined organic phases were washed with 70 mL of brine, dried over Na$_2$SO$_4$ and concentrated in vacuo. The residue was chromatographed with a short alumina column (1:10 (v/v) EtOAc/n-hexane) to afford the desired compound as yellow oil (3.3 g, 88.7%).

$^1$H NMR (400 MHz, CDCl$_3$): δ 1.27 (m, J=6.8 Hz, 6H), 1.42 (m, 4H), 4.18 (m, 4H).

Step 2) 1-(ethoxycarbonyl)cyclopropanecarboxylic acid

To a solution of diethyl cyclopropane-1,1-dicarboxylate (4.77 g, 25.6 mmol) in ethanol (40 mL) was added KOH (1.43 g, 25.6 mmol) in H$_2$O (8 mL), and the reaction mixture was stirred at room temperature overnight. The ethanol was removed under reduced pressure. The residue was neutralized with HCl (6 mL, 5 mol/L), then extracted with EtOAc (100 mL×3). The combined organic phases were dried over Na₂SO₄, filtered and the filtrate was concentrated in vacuo to give the title compound as a white solid (3.58 g, 88.4%).

¹H NMR (400 MHz, CDCl₃): δ 1.27 (t, J=6.7 Hz, 3H), 1.83 (m, 2H), 1.86 (m, 2H), 4.25 (m, 2H).

Step 3) ethyl 1-(phenyl carbamoyl)cyclopropane carboxylate

To a solution of 1-(ethoxycarbonyl)cyclopropane carboxylic acid (7.4 g, 46.84 mmol) in dry CH₂Cl₂ (70 mL) was added HATU (35.62 g, 93.67 mmol) at 0° C. After stirring for 10 minutes, a solution of the aniline (8.71 g, 93.67 mmol) and Et₃N (9.48 g, 93.67 mmol) in dry CH₂Cl₂ (30 mL) was then added and the reaction mixture was continued to stir at 40° C. for 24 hrs. The reaction mixture was quenched with water (30 mL) and extracted with CH₂Cl₂ (100 mL×3). The combined organic phases were dried over anhydrous Na₂SO₄, filtered and the filtrate was concentrated in vacuo. The residue was chromatographed with a silica gel column (1:5 (v/v) EtOAc/n-hexane) to afford the title compound as a pale yellow solid (9.7 g, 89%).

¹H NMR (400 MHz, CDCl₃): δ 1.27 (t, J=6.8 Hz, 3H), 1.76 (m, 2H), 1.85 (m, 2H), 4.20 (m, 2H), 6.68-6.71 (m, 1H), 7.32-7.35 (m, 2H), 7.57-7.60 (m, 2H), 10.88 (s, 1H).

Step 4) 1-(phenylcarbamoyl)cyclopropanecarboxylic acid

To a solution of ethyl 1-(phenyl carbamoyl)cyclopropane carboxylate (13 g, 55.79 mmol) in ethanol/THF (1/1, 100 mL) was added KOH (4.69 g, 83.69 mmol) in H₂O (8 mL) and the mixture was stirred at room temperature overnight. The ethanol and THF were removed under reduced pressure. The residue was neutralized with HCl (5 mol/L, 20 mL), and extracted with EtOAc (150 mL×3). The combined organic phases were dried over Na₂SO₄, filtered and the filtrate was concentrated in vacuo to afford the title compound as a white solid (10.1 g, 88.6%).

¹H NMR (400 MHz, CDCl₃): δ 1.77 (m, 2H), 1.84 (m, 2H), 7.10 (m, 1H), 7.30-7.34 (m, 2H), 7.53-7.55 (m, 2H), 10.61 (s, 1H).

Step 5) N-(4-(7-(benzyloxy)quinolin-4-yloxy)-3-fluorophenyl)-N-phenylcyclopropane-1,1-dicarboxamide To a solution of 1-(phenylcarbamoyl)cyclopropanecarboxylic acid (1.14 g, 5.6 mmol) in dry CH₂Cl₂ (8 mL) was added HATU (2.11 g, 5.6 mmol) at 0° C. After stirring for 10 minutes, a solution of the 4-(7-(benzyloxy)quinolin-4-yloxy)-3-fluorobenzenamine (1.0 g, 2.8 mmol) and Et₃N (0.7 g, 6.9 mmol) in dry CH₂Cl₂ (5 mL) was added. The reaction mixture was stirred at 40° C. for 24 hrs, quenched with water (10 mL), and extracted with CH₂Cl₂ (30 mL×3). The combined organic phases were dried over anhydrous Na₂SO₄, filtered and the filtrate was concentrated in vacuo. The residue was chromatographed with a silica gel column (1:1 (v/v) EtOAc/n-hexane) to afford the title compound as a white solid (1.3 g, 85%).

MS (ESI, pos. ion) m/z: 548 (M+1); LC-MS Rt: 4.595 min;

¹H NMR (400 MHz, CDCl₃): δ 1.60 (m, 2H), 1.83 (m, 2H), 5.25 (s, 2H), 6.45 (m, 1H), 7.28-7.29 (m, 1H), 7.16-7.24 (m, 2H), 7.34-7.57 (m, 10H), 7.78-7.81 (m, 1H), 7.99 (s, 1H), 8.30 (d, J=9.2 Hz, 1H), 8.60 (d, J=6 Hz, 1H), 10.29 (s, 1H).

Step 6) N-(4-(7-hydroxyquinolin-4-yloxy)-3-fluorophenyl)-N-phenylcyclopropane-1,1-dicarboxamide A solution of N-(4-(7-(benzyloxy)quinolin-4-yloxy)-3-fluorophenyl)-N-phenyl-cyclopropane-1,1-dicarboxamide (0.7 g, 1.28 mmol) and Pd/C (0.8 g) in methanol (20 mL) under H₂ was stirred at room temperature for 1.5 hrs, then the reaction mixture was filtered and washed with methanol (3×10 mL). The combined organic solvent was concentrated in vacuo to give N-(5-(7-hydroxy-quinolin-4-yloxy)pyridin-2-yl)-N-phenylcyclopropane-1,1-dicarboxamide as a white solid (0.53 g, 90.6%).

MS (ESI, pos. ion) m/z: 457 (M+1); LC-MS Rt: 3.936 min;

¹H NMR (400 MHz, MeOD): δ 1.66 (s, 1H), 6.81 (d, J=6.4 Hz, 1H), 7.14 (t, J=7.6 Hz, 1H), 7.33 (m, 3H), 7.41-7.48 (m, 3H), 7.55 (d, J=8 Hz, 2H), 7.92 (d, J=12.8 Hz, 1H), 8.49 (d, J=8.8 Hz, 1H), 8.69 (d, J=6 Hz, 1H).

Step 7) N-(4-(7-(4-oxaspiro[2.4]heptane-6-yloxy)quinolin-4-yloxy)-3-fluorophenyl)-N-phenylcyclopropane-1,1-dicarboxamide

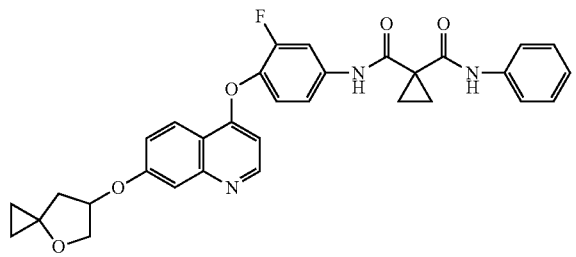 [SMILES: O=C(Nc1ccccc1)C1(C(=O)Nc2ccc(Oc3ccnc4cc(OC5COC6(CC6)C5)ccc34)c(F)c2)CC1]

To a mixture of (4-oxaspiro[2.4]heptane-6-yl)methanesulfonate (168 mg, 0.877 mmol, from example 6) and N-(4-(7-hydroxyquinolin-4-yloxy)-3-fluorophenyl)-N-phenylcyclopropane-1,1-dicarboxamide (300 mg, 0.584 mmol) in 5 mL of N,N-dimethylacetamide was added cesium carbonate (893 mg, 2.74 mmol). After stirring at room temperature for 36 hrs, the reaction mixture was warmed up to 40° C. and continued to stir for 8 hrs. The reaction mixture was concentrated in vacuo and the residue was chromatographed with a silica gel column (1:1 (v/v) EtOAc/n-hexane) to afford the title compound as a white solid (65 mg, 18%).

MS (ESI, pos. ion) m/z: 554.1 (M+1); LC-MS Rt: 4.354 min;

¹H NMR (400 MHz, CDCl₃): δ 0.53 (m, 1H), 0.65 (m, 1H), 0.89 (m, 1H), 1.00 (m, 1H), 1.60 (m, 2H), 1.84 (m, 2H), 2.25 (m, 1H), 2.53 (m, 1H), 4.20 (m, 2H), 5.22 (m, 1H), 6.39 (d, J=5.2 Hz, 1H), 7.19 (m, 2H), 7.28 (m, 2H), 7.38 (m, 2H), 7.48 (m, 2H), 7.77 (m, 1H), 7.59 (s, 1H), 8.28 (d, J=9.2 Hz, 1H), 8.58 (d, J=5.2 Hz, 1H).

Example 22

N-(4-(7-(((5R)-4-oxaspiro[2.4]heptane-5-yl)methoxy)quinolin-4-yloxy)-3-fluorophenyl)-N-phenylcyclopropane-1,1-dicarboxamide

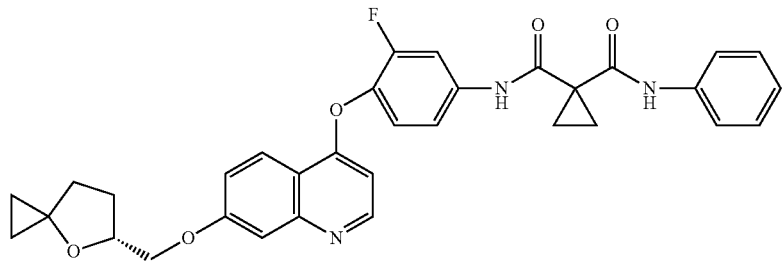 [SMILES: O=C(Nc1ccccc1)C1(C(=O)Nc2ccc(Oc3ccnc4cc(OC[C@H]5CCC6(CC6)O5)ccc34)c(F)c2)CC1]

To a mixture of ((5S)-4-oxaspiro[2.4]heptane-5-yl)methyl methanesulfonate (181.2 mg, 0.877 mmol, from example 2) and N-(4-(7-hydroxyquinolin-4-yloxy)-3-fluorophenyl)-N-phenyl-cyclopropane-1,1-dicarboxamide (300 mg, 0.656 mmol) in 5 mL of N,N-dimethylacetamide was added cesium carbonate (893 mg, 2.74 mmol). After stirring at room temperature for 36 hrs, then the reaction mixture was warmed up to 40° C. and stirred for 8 hrs. The reaction mixture was concentrated in vacuo and the residue was chromatographed with a silica gel column (1:1 (v/v) EtOAc/n-hexane) to give the title compound as a white solid (234 mg, 63%).

MS (ESI, pos. ion) m/z: 568.2 (M+1); LC-MS Rt: 4.364 min;

$^1$H NMR (400 MHz, CDCl$_3$): δ 0.56 (m, 2H), 0.91 (m, 2H), 1.60 (m, 4H), 1.83 (m, 2H), 2.03 (m, 2H), 4.18 (m, 2H), 4.52 (s, 1H), 6.38 (m, 1H), 7.20 (m, 2H), 7.30 (m, 1H), 7.38 (m, 3H), 7.48 (m, 2H), 7.76 (m, 1H), 8.02 (s, 1H), 8.25 (d, J=9.2 Hz, 1H), 8.58 (d, J=5.2 Hz, 1H), 10.18 (s, 1H).

Example 23

N-(4-(7-(3-(1-hydroxycyclopropyl)propoxy)quinolin-4-yloxy)-3-fluorophenyl)-N-phenylcyclopropane-1,1-dicarboxamide

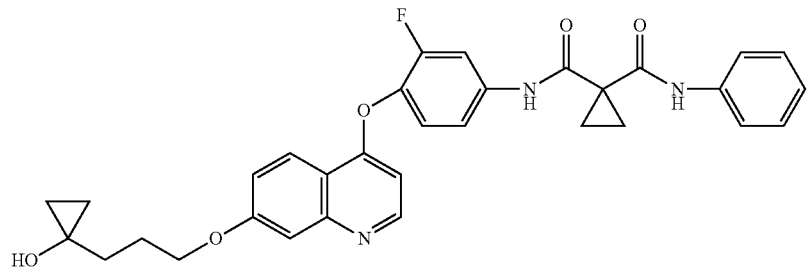 [SMILES: O=C(Nc1ccccc1)C1(C(=O)Nc2ccc(Oc3ccnc4cc(OCCCC5(O)CC5)ccc34)c(F)c2)CC1]

To a mixture of 3-(1-hydroxycyclopropyl)propyl methanesulfonate (170.7 mg, 0.877 mmol, from example 9) and N-(4-(7-hydroxyquinolin-4-yloxy)-3-fluorophenyl)-N-phenylcyclopropane-1,1-dicarboxamide (300 mg, 0.656 mmol) in 5 mL of N,N-dimethylacetamide was added cesium carbonate (893 mg, 2.74 mmol). After stirring at room temperature for 36 hrs, then the reaction mixture was warmed to 40° C. for 8 hrs. The reaction mixture was concentrated in vacuo and the residue was chromatographed with a silica gel column (4:1 (v/v) EtOAc/n-hexane) to afford the title compound as a white solid (364.1 mg, 74%).

MS (ESI, pos. ion) m/z: 556.2 (M+1); LC-MS Rt: 4.110 min;

$^1$H NMR (400 MHz, CDCl$_3$): δ 0.51 (s, 2H), 0.79 (s, 2H), 1.25 (s, 2H), 1.81 (m, 4H), 2.15 (m, 2H), 3.38 (s, 3H), 4.24 (m, 2H), 6.38 (d, J=4.8 Hz, 1H), 7.25 (m, 4H), 7.46 (m, 1H), 7.77 (d, J=12 Hz, 1H), 7.97 (s, 1H), 8.26 (d, J=9.2 Hz, 1H), 8.58 (d, J=4.8 Hz, 1H), 10.18 (s, 1H).

Example 24

N-(5-(7-(4-oxaspiro[2.4]heptane-6-yloxy)quinolin-4-yloxy)pyridin-2-yl)-N-phenylcyclopropane-1,1-dicarboxamide

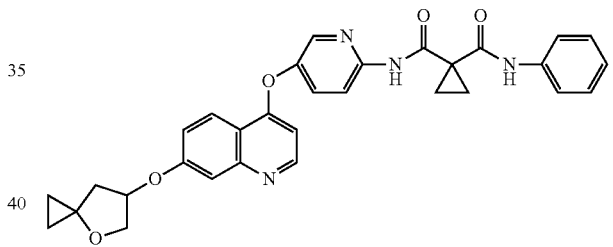

Step 1) N-(5-(7-(benzyloxy)quinolin-4-yloxy)pyridin-2-yl)-N-phenylcyclopropane-1,1-dicarboxamide The title compound was prepared according to the procedure described in Example 21 of step 5 by using 1-(phenylcarbamoyl)cyclopropanecarboxylic acid (1.14 g, 5.6 mmol), HATU (2.11 g, 5.6 mmol), 5-(7-(benzyloxy)quinolin-4-yloxy)pyridin-2-amine (960 mg, 2.8 mmol) and DBU (868 mg, 7.0 mmol) in dry DCM (50 mL). The title compound was obtained as a white solid (1.22 g, 82%).

MS (ESI, pos. ion) m/z: 531.1 (M+1); LC-MS Rt: 4.583 min;

$^1$H NMR (400 MHz, CDCl$_3$): δ 1.67 (m, 2H), 1.80 (m, 2H), 5.24 (s, 2H), 6.43 (d, J=4.8 Hz, 1H), 7.14 (m, 1H), 7.34 (m, 4H), 7.41 (m, 2H), 7.43 (m, 3H), 7.51 (m, 3H), 8.24 (m, 2H), 8.30 (d, J=8.8 Hz, 1H), 8.61 (d, J=5.2 Hz, 1H), 9.10 (s, 1H), 9.44 (s, 1H).

Step 2) N-(5-(7-hydroxyquinolin-4-yloxy)pyridin-2-yl)-N-phenylcyclopropane-1,1-dicarboxamide A solution of N-(5-(7-(benzyloxy)quinolin-4-yloxy)pyridin-2-yl)-N-phenylcyclopropane-1,1-dicarboxamide (1.22 g, 2.3 mmol) and Pd/C (1.2 g) in methanol (30 mL) under H$_2$ was stirred at room temperature for 2 hrs, then the reaction mixture was filtered and washed with methanol (10 mL×3). The combined solvent was concentrated in vacuo to give N-(5-(7-hydroxyquinolin-4-yloxy)pyridin-2-yl)-N-phenylcyclopropane-1,1-dicarboxamide as a white solid (910.8 mg, 90%).

MS (ESI, pos. ion) m/z: 441.2 (M+1); LC-MS Rt: 3.508 min;

$^1$H NMR (400 MHz, CD$_3$OD): δ 1.69 (m, 4H), 6.55 (d, J=5.6 Hz, 1H), 7.14 (m, 1H), 7.30 (m, 4H), 7.56 (m, 2H), 7.74 (m, 1H), 8.29 (m, 3H), 8.55 (d, J=5.6 Hz, 1H).

Step 3) N-(5-(7-(4-oxaspiro[2.4]heptane-6-yloxy)quinolin-4-yloxy)pyridin-2-yl)-N-phenylcyclopropane-1,1-dicarboxamide

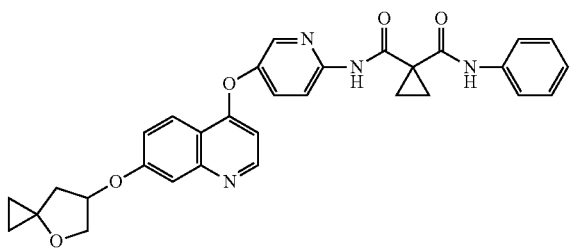 [SMILES: O=C(Nc1ccccc1)C1(C(=O)Nc2ccc(Oc3ccnc4cc(OC5COC6(CC6)C5)ccc34)cn2)CC1]

To a mixture of (4-oxaspiro[2.4]heptane-6-yl)methanesulfonate (168 mg, 0.877 mmol) and N-(5-(7-hydroxyquinolin-4-yloxy)pyridin-2-yl)-N-phenylcyclopropane-1,1-dicarboxamide (300 mg, 0.682 mmol) in 5 mL of N,N-dimethylacetamide was added cesium carbonate (893 mg, 2.74 mmol). After stirring at room temperature for 36 hrs, then the reaction mixture was warmed up to 40° C. for 8 hrs. The reaction mixture was concentrated in vacuo and the residue was chromatographed with a silica gel column (2:1 (v/v) EtOAc/n-hexane) to afford the title compound as a white solid (73 mg, 20%).

MS (ESI, pos. ion) m/z: 537.1 (M+1); LC-MS Rt: 4.429 min;

$^1$H NMR (400 MHz, CDCl$_3$): δ 0.60 (m, 2H), 0.95 (m, 2H), 1.70 (m, 4H), 2.40 (m, 1H), 2.54 (m, 1H), 4.19 (m, 2H), 5.23 (m, 1H), 6.42 (d, J=4.2 Hz, 1H), 7.28 (m, 3H), 7.34 (m, 3H), 7.58 (m, 3H), 8.24 (m, 2H), 8.62 (d, J=5.2 Hz, 1H), 9.10 (s, 1H).

Example 25

N-(5-(7-(3-(1-hydroxycyclopropyl)propoxy)quinolin-4-yloxy)pyridin-2-yl)-N-phenylcyclopropane-1,1-dicarboxamide

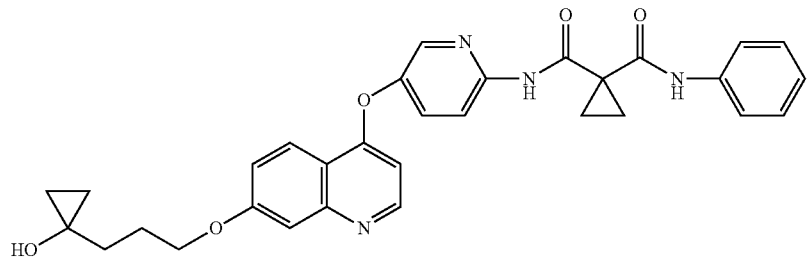 [SMILES: O=C(Nc1ccccc1)C1(C(=O)Nc2ccc(Oc3ccnc4cc(OCCCC5(O)CC5)ccc34)cn2)CC1]

The title compound was prepared according to the procedure described in Example 9 by using N-(5-(7-hydroxyquinolin-4-yloxy)pyridin-2-yl)-N-phenyl-cyclopropane-1,1-dicarboxamide (300 mg, 0.682 mmol), 3-(1-hydroxycyclopropyl)-propyl methanesulfonate (155 mg, 0.80 mmol), and Cs$_2$CO$_3$ (668 mg, 2.05 mmol) in 3 mL of DMA. The residue was purified by a silical gel column chromatography (3:1 (v/v) EtOAc/n-hexane) to give the title compound as a white solid (238.5 mg, 65%).

MS (ESI, pos. ion) m/z: 539.2 (M+1); LC-MS Rt: 4.156 min;

$^1$H NMR (400 MHz, CDCl$_3$): δ 0.51 (m, 2H), 0.81 (m, 2H), 1.69 (m, 2H), 1.82 (m, 4H), 2.15 (m, 2H), 4.25 (m, 2H), 6.42 (d, J=5.2 Hz, 1H), 7.16 (m, 1H), 7.23 (d, J=2.8 Hz, 1H), 7.36 (m, 2H), 7.44 (d, J=2.4 Hz, 1H), 7.58 (m, 3H), 8.24 (m, 2H), 8.31 (d, J=8.8 Hz, 1H), 8.62 (d, J=5.2 Hz, 1H).

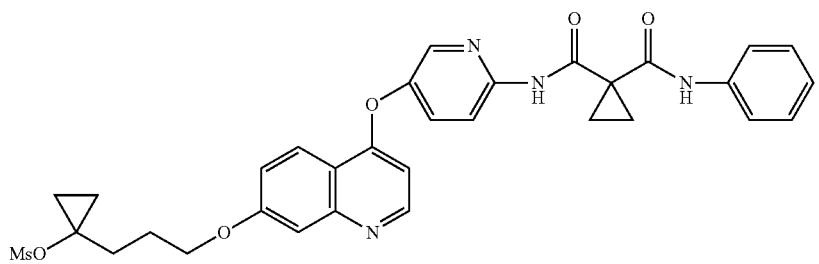 [SMILES: CS(=O)(=O)OC1(CCCOc2ccc3c(Oc4ccc(NC(=O)C5(C(=O)Nc6ccccc6)CC5)nc4)ccnc3c2)CC1]

Chromatography separation also provided N-(5-(7-(3-(1-cyclopropyl methanesulfonate-1-yl)propoxy)quinolin-4-yloxy)pyridin-2-yl)-N-phenylcyclopropane-1,1-dicarboxamide as a pale yellow solid.

MS (ESI, pos. ion) m/z: 617.1 (M+1); LC-MS Rt: 4.491 min;

¹H NMR (400 MHz, CDCl₃): δ0.78 (m, 2H), 1.31 (m, 2H), 1.67 (m, 2H), 1.81 (m, 2H), 2.14 (m, 4H), 3.02 (s, 3H), 4.23 (m, 2H), 6.41 (d, J=5.2 Hz, 1H), 7.14 (m, 1H), 7.22 (m, 2H), 7.35 (m, 2H), 7.41 (d, J=2.4 Hz, 1H), 7.58 (m, 3H), 8.22 (m, 2H), 8.30 (d, J=9.2 Hz, 1H), 8.61 (d, J=5.2 Hz, 1H), 9.09 (s, 1H), 9.43 (s, 1H).

Example 26

N-(4-(7-(4-oxaspiro[2.4]heptane-6-yloxy)-6-methoxyquinolin-4-yloxy)-3-fluorophenyl)-N-phenylcyclopropane-1,1-dicarboxamide

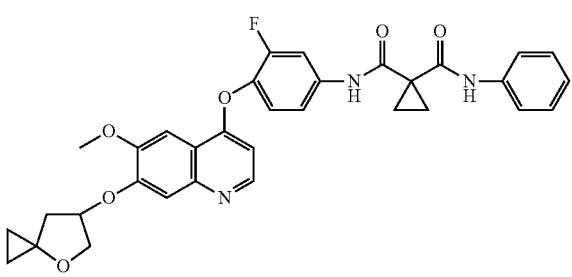 [SMILES: COc1cc2c(Oc3ccc(NC(=O)C4(C(=O)Nc5ccccc5)CC4)cc3F)ccnc2cc1OC1COC2(CC2)C1]

The title compound was prepared according to the procedure described in Example 24 by using (4-oxaspiro[2.4]heptane-6-yl)methanesulfonate (138 mg, 0.72 mmol), N-(4-(7-hydroxy-6-methoxyquinolin-4-yloxy)-3-fluorophenyl)-N-phenylcyclopropane-1,1-dicarboxamide (300 mg, 0.616 mmol), and Cs₂CO₃ (602.5 mg, 1.848 mmol) in 3 mL of DMA. The residue was purified by a silical gel column chromatography (2:1 (v/v) EtOAc/n-hexane). The title compound was obtained as a white solid (186.7 mg, 52%).

MS (ESI, pos. ion) m/z: 583.9 (M+1); LC-MS Rt: 4.432 min;

¹H NMR (400 MHz, CDCl₃): δ0.55 (m, 1H), 0.65 (m, 1H), 0.90 (m, 1H), 1.05 (m, 1H), 1.60 (m, 2H), 1.85 (m, 2H), 4.04 (s, 3H), 4.24 (m, 2H), 5.25 (m, 1H), 6.41 (d, J=4.4 Hz, 1H), 7.20 (m, 2H), 7.25 (m, 1H), 7.30 (m, 2H), 7.40 (m, 1H), 7.50 (m, 2H), 7.60 (s, 1H), 7.80 (m, 2H), 7.95 (m, 1H) 8.50 (d, J=5.2 Hz, 1H), 10.25 (s, 1H).

Example 27

N-(4-(7-(3-(1-hydroxycyclopropyl)propoxy)-6-methoxyquinolin-4-yloxy)-3-fluorophenyl)-N-phenylcyclopropane-1,1-dicarboxamide

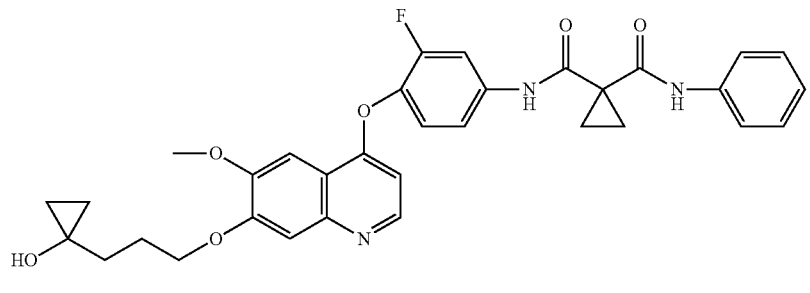 [SMILES: COc1cc2c(Oc3ccc(NC(=O)C4(C(=O)Nc5ccccc5)CC4)cc3F)ccnc2cc1OCCCC1(O)CC1]

The title compound was prepared according to the procedure described in Example 9 by using N-(4-(7-hydroxy-6-methoxyquinolin-4-yloxy)-3-fluorophenyl)-N-phenylcyclopropane-1,1-dicarboxamide (300 mg, 0.616 mmol), 3-(1-hydroxycyclopropyl)propyl methanesulfonate (155 mg, 0.80 mmol), and Cs₂CO₃ (602.5 mg, 1.848 mmol) in 3 mL of DMA. The residue was purified by a silical gel column chromatography (6:1 (v/v) EtOAc/n-hexane). The title compound was obtained as a white solid (263 mg, 73%).

MS (ESI, pos. ion) m/z: 586.2 (M+1); LC-MS Rt: 4.244 min;

¹H NMR (400 MHz, CDCl₃): δ0.46 (s, 2H), 0.76 (m, 2H), 1.61 (m, 2H), 1.84 (m, 4H), 2.22 (t, J=6.4 Hz, 2H), 4.03 (s, 3H), 4.30 (t, J=6 Hz, 2H), 6.41 (m, 1H), 7.21-7.58 (m, 8H), 7.80 (m, 1H), 7.95 (s, 1H), 8.49 (d, J=5.2 Hz, 1H), 10.24 (s, 1H).

N-(4-(7-(3-(1-cyclopropyl methanesulfonate-1-yl)propoxy)-6-methoxyquinolin-4-yloxy)-3-fluorophenyl)-N-phenylcyclopropane-1,1-dicarboxamide was obtained as a pale yellow solid.

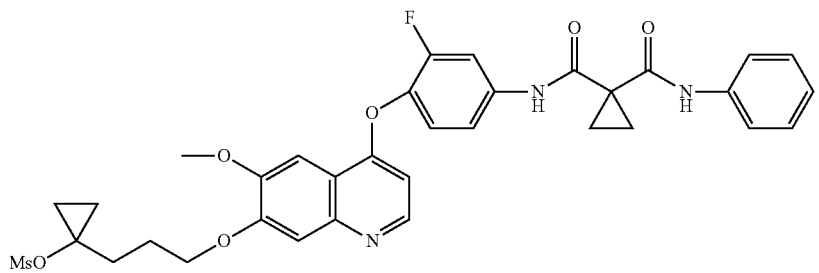 [SMILES: COc1cc2c(Oc3ccc(NC(=O)C4(C(=O)Nc5ccccc5)CC4)cc3F)ccnc2cc1OCCCC1(OS(C)(=O)=O)CC1]

MS (ESI, pos. ion) m/z: 664.2 (M+1); LC-MS Rt: 4.563 min;

$^1$H NMR (400 MHz, CDCl$_3$): δ0.78 (m, 2H), 1.30 (m, 2H), 1.60 (m, 2H), 1.85 (m, 2H), 2.11 (m, 2H), 2.25 (m, 2H), 3.06 (s, 3H), 4.03 (s, 3H), 4.28 (m, 2H), 6.41 (d, J=4.8 Hz, 1H), 7.22 (m, 2H), 7.27 (m, 3H), 7.39 (m, 2H), 7.49 (d, J=8 Hz, 1H), 7.57 (s, 1H), 7.79 (d, J=12 Hz, 1H), 7.94 (s, 1H).

Example 28

N-(4-(7-(3-(1-hydroxycyclopropyl)propoxy)-6-methoxyquinolin-4-yloxy)-3-fluorophenyl)-N-(4-fluorophenyl)cyclopropane-1,1-dicarboxamide

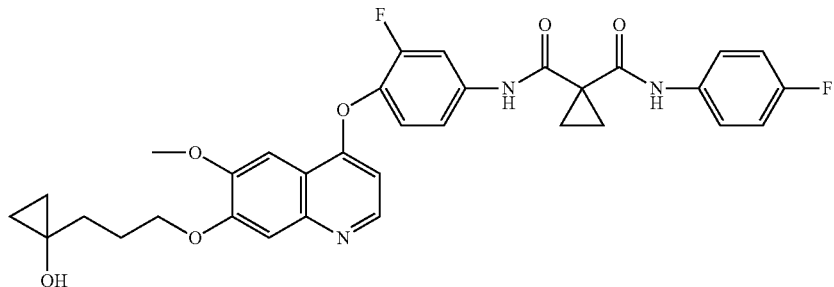 [SMILES: COc1cc2c(Oc3ccc(NC(=O)C4(C(=O)Nc5ccc(F)cc5)CC4)cc3F)ccnc2cc1OCCCC1(O)CC1]

The title compound was prepared according to the procedure described in Example 9 by using N-(4-(7-hydroxy-6-methoxyquinolin-4-yloxy)-3-fluorophenyl)-N-(4-fluorophenyl)cyclopropane-1,1-dicarboxamide (300 mg, 0.594 mmol), 3-(1-hydroxycyclopropyl)propyl methanesulfonate (155 mg, 0.80 mmol), and Cs$_2$CO$_3$ (581 mg, 1.782 mmol) in 3 mL of DMA. The residue was purified by a silical gel column chromatography (6:1 (v/v) EtOAc/n-hexane). The title compound was obtained as a white solid (247 mg, 69%).

MS (ESI, pos. ion) m/z: 604.2 (M+1); Rt: 4.240 min;

$^1$H NMR (400 MHz, CDCl$_3$): δ0.46 (m, 2H), 0.75 (m, 2H), 1.64 (m, 2H), 1.83 (m, 4H), 2.22 (m, 2H), 4.03 (s, 3H), 4.31 (m, 2H), 6.41 (m, 1H), 7.08 (m, 2H), 7.25 (m, 1H), 7.46-7.79 (m, 5H), 8.19 (s, 1H), 8.49 (d, J=5.2 Hz, 1H), 10.00 (s, 1H).

Biological Testing

The efficacy of the compounds of the invention as inhibitors of receptor tyrosine kinases, such as c-Met, KDR and/or IGF 1R related activity and as anti-tumor agents in xenograft animal models can be evaluated as follows.

MTT Cell Assay

Preparation Instructions:

MTT ((3-(4,5-Dimethylthiazol-2-yl)-2,5-diphenyltetrazolium bromide) is soluble in water (10 mg/ml), ethanol (20 mg/ml) and is also soluble in buffered salt solutions and culture media (5 mg/ml).

MTT Solution: 5 mg/ml MTT in PBS. Solution must be filter sterilized after adding MTT.

MTT Solvent: 4 mM HCl, 0.1% Nondet P-40 (NP40) all in isopropanol.

Procedure:

Short 96 well assay: EACH condition was done in triplicate or more.

1. DAY ONE: Trypsinized one T-25 flask and added 5 ml of complete media to trypsinized cells. Centrifuged in a sterile 15 ml falcon tube at 500 rpm in the swinging bucked rotor (~400×g) for 5 min.
2. Removed media and resuspended cells to 1.0 ml with complete media.
3. Counted and recorded cells per ml.
4. Diluted the cells (cv=cv) to 75,000 cells per ml. Used completed media to dilute cells.
5. Added 100 μA of cells (7500 total cells) into each well and incubated overnight.
6. DAY TWO: Treated cells on day two with inhibitors. Final volume was 100 μA per well.
7. DAY THREE: Added 20 μl of 5 mg/ml MTT to each well. Included one set of wells with MTT but no cells (control).
8. Incubated for 3.5 hours at 37° C. in culture hood.
9. Carefully removed media.
10. Added 150 μl MTT solvent.
11. Covered with tinfoil and agitate cells on orbital shaker for 15 min.
12. Read absorbance at 590 nm with a reference filter of 620 nm.

Kinase Assays

Kinase assays can be performed by measurement of incorporation of γ-$^{33}$P ATP into immobilized myelin basic protein (MBP). High binding white 384 well plates (Greiner) are coated with MBP (Sigma #M-1891) by incubation of 60 μl/well of 20 μg/ml MBP in Tris-buffered saline (TBS; 50 mM Tris pH 8.0, 138 mM NaCl, 2.7 mM KCl) for 24 hours at 4° C. Plates are washed 3× with 100 μl TBS. Kinase reactions are carried out in a total volume of 34 μl in kinase buffer (5 mM Hepes pH 7.6, 15 mM NaCl, 0.01% bovine gamma globulin (Sigma #I-5506), 10 mM $MgCl_2$, 1 mM DTT, 0.02% TritonX-100). Compound dilutions are performed in DMSO and added to assay wells to a final DMSO concentration of 1%. Each data point is measured in duplicate, and at least two duplicate assays are performed for each individual compound determination. Enzyme is added to final concentrations of 10 nM or 20 nM, for example. A mixture of unlabeled ATP and $\gamma$-$^{33}$P ATP is added to start the reaction ($2\times10^6$ cpm of $\gamma$-$^{33}$P ATP per well (3000 Ci/mmole) and either 10 μM unlabeled ATP, typically. The reactions are carried out for 1 hour at room temperature with shaking Plates are washed 7× with TBS, followed by the addition of 50 μl/well scintillation fluid (Wallac). Plates are read using a Wallac Trilux counter. This is only one format of such assays, various other formats are possible, as known to one skilled in the art.

The above assay procedure can be used to determine the $IC_{50}$ for inhibition and/or the inhibition constant, $K_i$. The $IC_{50}$ is defined as the concentration of compound required to reduce the enzyme activity by 50% under the condition of the assay. Exemplary compositions have $IC_{50}$'s of, for example, less than about 100 μM, less than about 10 μM, less than about 1 μM, and further for example having $IC_{50}$'s of less than about 100 nM, and still further, for example, less than about 10 nM. The $K_1$ for a compound may be determined from the $IC_{50}$ based on three assumptions. First, only one compound molecule binds to the enzyme and there is no cooperativity. Second, the concentration of active enzyme and the compound tested are known (i.e., there are no significant amounts of impurities or inactive forms in the preparations). Third, the enzymatic rate of the enzyme-inhibitor complex is zero.

Kinase Inhibition and Cellular Assays.

In vitro kinase assays can also be done to establish $IC_{50}$ values against a variety of recombinant receptor and nonreceptor kinases. Optimal enzyme, ATP, and substrate (gastrin peptide) concentrations are established for each enzyme using homogeneous time-resolved fluorescence (HTRF) assays. Compounds are tested in a 10-point dose-response curve for each enzyme using an ATP concentration of two-thirds Km for each. Most assays consist of enzyme mixed with kinase reaction buffer [20 mmol/L Tris-HCl (pH 7.5), 10 mmol/L $MgCl_2$, 5 mmol/L $MnCl_2$, 100 mmol/L NaCl, 1.5 mmol/L EGTA]. A final concentration of 1 mmol/L DTT, 0.2 mmol/L $NaVO_4$, and 20 Ag/mL BSA is added before each assay. For Src, a modified kinase reaction buffer is used that included 20 mmol/L Tris-HCl (pH 7.5), 2.5 mmol/L $MnCl_2$, 100 mmol/L NaCl, and 1.5 mmol/L EGTA. A final concentration of 1 mmol/L DTT, 0.2 mmol/L $NaVO_4$, and 20 Ag/mL BSA is added before each assay. For all assays, 5.75 mg/mL streptavidin-allophycocyanin (ProZyme, San Leandro, Calif.) and 0.1125 nmol/L Eu-PT66 (Perkin-Elmer Corp., Boston, Mass.) are added immediately before the HTRF reaction. Plates are incubated for 30 minutes at room temperature and read on a Discovery instrument (Packard Instrument Co., Downers Grove, Ill.).

c-Met Assay c-Met biochemical activity can be assessed using a Luciferase-Coupled Chemilumineacent Kinase assay (LCCA) format as described above. Again, kinase activity is measured as the percent ATP remaining following the kinase reaction. Remaining ATP is detected by luciferase-luciferin-couple chemiluminescence. Specifically, the reaction is initiated by mixing test compounds, 1 μM ATP, 1 μM poly-EY and 10 nM c-Met (baculovirus expressed human c-Met kinase domain P948-S1343) in a 20 μL assay buffer (20 mM Tris-HCL pH7.5, 10 mM $MgCl_2$, 0.02% Triton X-100, 100 mM DTT, 2 mM $MnCl_2$). The mixture is incubated at ambient temperature for 2 hours after which 20 μL luciferase-luciferin mix is added and the chemiluminescent signal read using a Wallac Victor$^2$ reader. The luciferase-luciferin mix consists of 50 mM HEPES, pH 7.8, 8.5n/mL oxalic acid (pH 7.8), 5 (or 50) mM DTT, 0.4% Triton X-100, 0.25 mg/mL coenzyme A, 63 μM AMP, 28 μg/mL luciferin and 40000 units of light/mL luciferase.

Tumor Xenograft Models

Human glioma tumor cells (U87MG cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Intial statistical analysis is done by repeated measures analysis of variance (RMANOVA), followed by Scheffe post hoc testing for multiple comparisons. Vehicle alone (captisol, or the like) is the negative control.

Human gastric adenocarcinoma tumor cells (MKN45 cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control.

A431 cells were cultured in DMEM (low glucose) with 10% FBS and penicillin/streptomycin/glutamine. Cells are harvested by trypsinization, washed, and adjusted to a concentration of $5\times10^7$/mL in serum-free medium. Animals are challenged s.c. with $1\times10^7$ cells in 0.2 mL over the left flank. Approximately 10 days thereafter, mice are randomized based on initial tumor volume measurements and treated with either vehicle (Ora-Plus) or test compounds. Tumor volumes and body weights are recorded twice weekly and/or on the day of sacrifice. Tumor volume is measured with a Pro-Max electronic digital caliper (Sylvac, Crissier, Switzerland) and calculated using the Formulalength (mm)×width (mm)× height (mm) and expressed in $mm^3$. Data are expressed as mean±SE. Repeated measures ANOVA followed by Scheffe post hoc testing for multiple comparisons was used to evaluate the statistical significance of observed differences.

What is claimed is:

1. A compound of Formula (I):

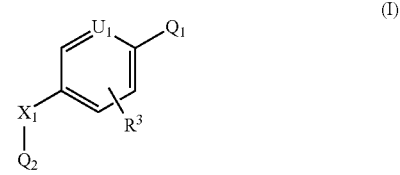

or a stereoisomer, a geometric isomer, a tautomer, an N-oxide, or a pharmaceutically acceptable salt thereof, wherein:

$Q_1$ is formula (IIa):

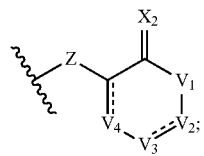
(IIa)

$Q_2$ is formula (III):

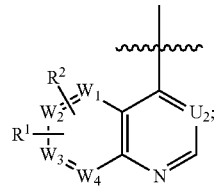
(III)

$R^1$ is hydroxy-substituted cyclopropylalkoxy, $R^5S(=O)_2$ O-substituted cyclopropylalkoxy, spiro bicyclyl, spiro heterobicyclyl, spiro bicyclyl aliphatic, spiro heterobicyclyl aliphatic, spiro bicycloxy, spiro heterobicyclylamino, spiro bicycloxoalkoxy, spiro heterobicycloxoalkoxy, spiro bicyclylaminoalkoxy, spiro heterobicyclylaminoalkoxy, spiro bicyclyl —C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)NR$^5$—, or spiro heterobicyclyl-C(=O)NR$^5$—, or $R^1$ has one of the following structures:

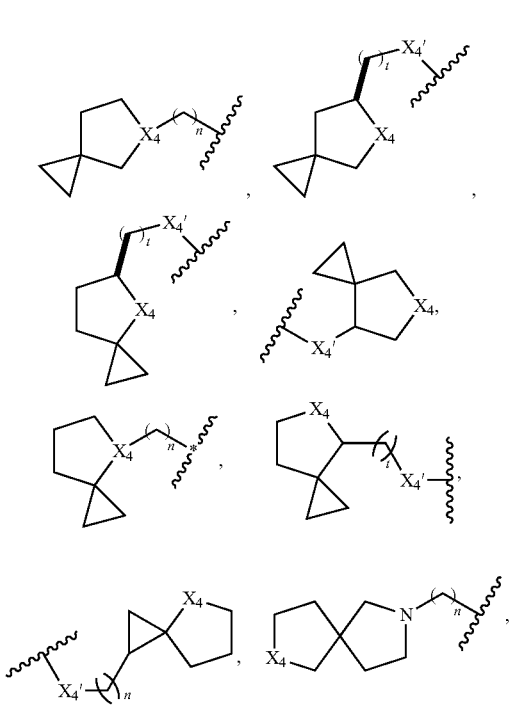

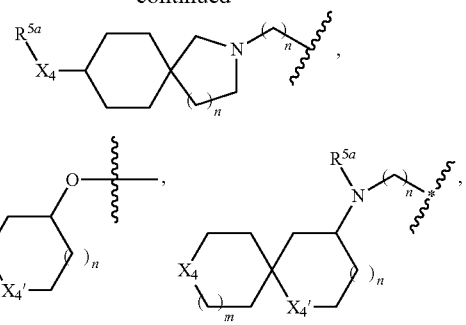

-continued

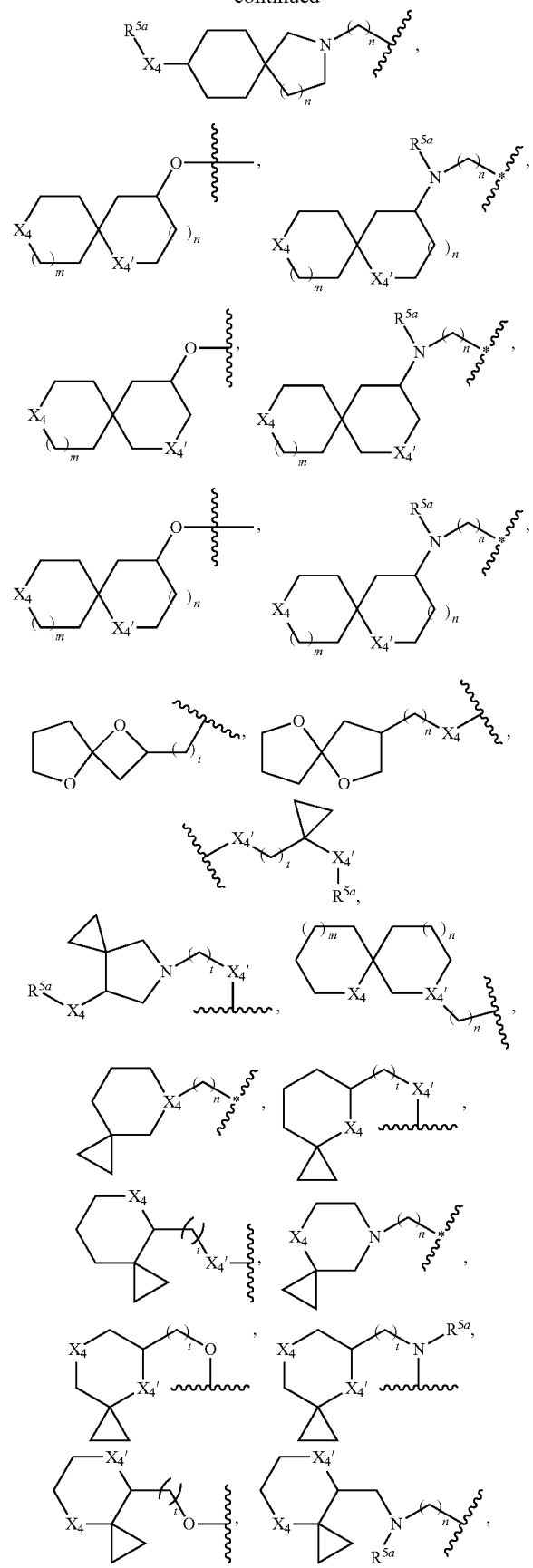

-continued

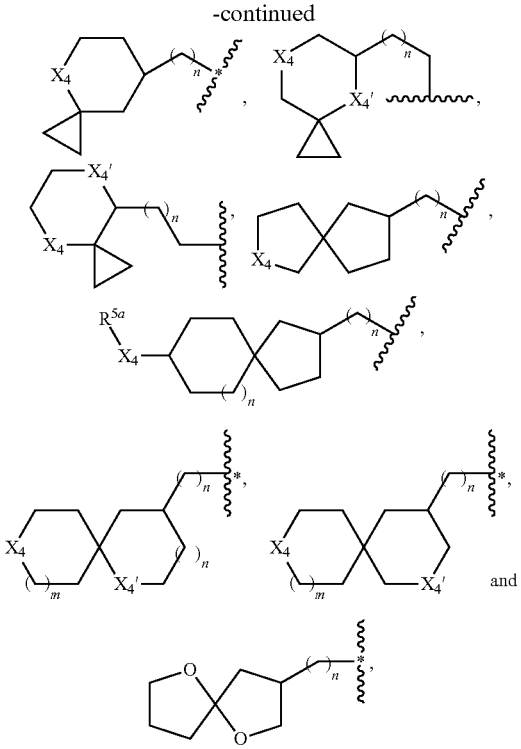

wherein each of X₄ and X₄' is independently $(CR^4R^{4a})_m$, $NR^5$, O, S, S=O or $SO_2$; each of m and n is independently 0, 1 or 2; and t is 1, 2 or 3;

R² is H, halo, cyano, hydroxyl, $R^{5a}R^5N—$, $—C(=O)NR^5R^{5a}$, $—OC(=O)NR^5R^{5a}$, $—OC(=O)OR^5$, $—NR^5C(=O)NR^5R^{5a}$, $—NR^5C(=O)OR^{5a}$, $—NR^5C(=O)—R^{5a}$, $R^5R^{5a}N—O_2S—$, $R^5O_2S—$, $R^5O_2SR^{5a}N—$, $R^{5a}R^5N$-alkyl, $R^5(S=O)$-alkyl, $R^5R^{5a}N$-(C=O)alkyl, $R^{5a}R^5N$-alkoxy, $R^5(S=O)$-alkoxy, $R^5R^{5a}N$-(C=O)-alkoxy, aliphatic, alkoxy, hydroxyalkoxy, aminoalkoxy, hydroxy-substituted aminoalkoxy, haloalkoxy, amino-substituted haloalkoxy, alkylamino haloalkoxy, hydroxy-substituted haloalkoxy, alkylaminoalkoxy, alkoxyalkoxy, arylalkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, aryloxy, heterocyclyloxyalkoxy, carbocyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicycloxoalkoxy, fused heterobicycloxoalkoxy, fused bicyclyl aminoalkoxy, fused heterobicyclyl aminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)NR⁵—, fused heterobicyclyl-C(=O)NR⁵—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicycloxoalkoxy, spiro heterobicycloxoalkoxy, spiro bicyclylaminoalkoxy, spiro heterobicyclylaminoalkoxy, spiro bicyclyl —C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)NR⁵—, or spiro heterobicyclyl-C(=O)NR⁵—, aryl, heteroaryl, arylaliphatic or heteroarylaliphatic, with the proviso that when alkoxy or alkylamino is substituted, each of alkoxy or alkylamino is independently substituted with one or more hydroxy groups, amino groups or substituted amino groups;

R³ is H, F, Cl, Br, I, —CN, hydroxyl, $R^{5a}R^5N—$, aliphatic, alkoxy, haloalkyl, heterocyclyl, heterocyclylalkyl, cycloalkyl, cycloalkyl aliphatic, cycloalkylalkoxy, or heterocyclylalkoxy;

each of U₁ and U₂ is independently $CR^4$ or N;

V₁ is O or $NR^5$;

V₂ is $cR^4R^{4a}$, NRS, $CR^4$ or N, and V₃ and V₄ combine to become $CR^4R^{4a}$, $NR^5$, O, $CR^4$ or N;

each of W₁, W₂, W₃ and W₄ is independently $CR^4R^{4a}$, $NR^5$, $CR^4$ or N;

X₁ is $(CR^4R^{4a})_m$, $NR^5$, O, S, S=O or $SO_2$, where m is 0, 1 or 2;

X₂ is O, S or $NR^5$;

Z is $—NR^5C(=O)—(CR^4R^{4a})_p—$, $—NR^5C(=S)—(CR^4R^{4a})_p—$, $—NR^{5a}—(CR^4R^{4a})_p—$, $—NR^5—(CR^4R^{4a})_pC(=O)—$, $—NR^5—(CR^4R^{4a})_pC(=S)—$, $—NR^5S(=O)_r—$, $—NR^5S(=O)_r(CR^4R^{4a})_p—$, $—C(=O)NR^5(CR^4R^{4a})_p—$ or $—NR^5—(CR^4R^{4a})_nS(=O)_r—$, where p is 0, 1, 2 or 3 and r is 1 or 2;

each of R⁴ and $R^{4a}$ is independently H, F, Cl, Br, I, —CN, hydroxyl, $—NR^{5a}R^5$, alkoxy, cycloalkoxy, heterocycloalkoxy, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl, with the proviso that where R⁴ and $R^{4a}$ are bonded to the same carbon atom, R⁴ and $R^{4a}$, together with the carbon atom they are attached to, optionally form a substituted or unsubstituted 3-8 membered carbocyclic or heterocyclic ring;

each of R⁵ and $R^{5a}$ is independently H, $R^6R^{6a}NC(=O)—$, $R^6OC(=O)—$, $R^6C(=O)—$, $R^6R^{6a}NS(=O)—$, $R^6OS(=O)—$, $R^6S(=O)—$, $R^6R^{6a}NSO_2—$, $R^6OSO_2—$, $R^6SO_2—$, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl, with the proviso that where R⁵ and $R^{5a}$ are bonded to the same nitrogen atom, R⁵ and $R^{5a}$, together with the nitrogen atom they are attached to, optionally form a substituted or unsubstituted 3-8 membered ring, including spiro and fused bicyclic rings;

each of R⁶ and $R^{6a}$ is independently H, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl, or carbocyclyl;

wherein each of $R^{5a}R^5N—$, $—C(=O)NR^5R^{5a}$, $—OC(=O)NR^5R^{5a}$, $—OC(=O)OR^5$, $—NR^5C(=O)NR^5R^{5a}$, $—NR^5C(=O)OR^{5a}$, $—NR^5C(=O)—R^{5a}$, R⁵R⁵N—O₂S—, R⁵O₂S—, R⁵O₂SR⁵ᵃN—, OR⁵, NR⁵, CR⁴R⁴ᵃ, CR⁴, (CR⁴R⁴ᵃ)ₘ, —NR⁵C(=O)—(CR⁴R⁴ᵃ)ₚ—, —NR⁵C(=S)—(CR⁴R⁴ᵃ)ₚ—, —NR⁵ᵃ-(CR⁴R⁴ᵃ)ₚ—, —NR⁵—(CR⁴R⁴ᵃ)ₚC(=O)—, —NR⁵—(CR⁴R⁴ᵃ)ₚC(=S)—, —NR⁵S(=O)ᵣ—, —NR⁵S(=O)(CR⁴R⁴ᵃ)ₚ—, —C(=O)NR⁵—(CR⁴R⁴ᵃ)ₚ—, —NR⁵—(CR⁴R⁴ᵃ)ₚ—S(=O)ᵣ—, R⁵ᵃR⁵N-alkyl, R⁵S(=O)-alkyl, R⁵R⁵N—C(=O)-alkyl, R⁵ᵃR⁵N-alkoxy, R⁵S(=O), alkoxy, R⁵R⁵N—C(=O)-alkoxy, R⁶R⁶ᵃNC(=O)—, R⁶OC(=O)—, R⁶C(=O)—, R⁶R⁶ᵃNS(=O)—, R⁶OS(=O)—, R⁶S(=O)—, R⁶R⁶ᵃNSO₂—, R⁶OSO₂—, R⁶SO₂—, hydroxy-substituted cyclopropylalkoxy, R⁵S(=O)₂O-substituted cyclopropylalkoxy, aliphatic, alkoxy, hydroxyalkoxy, aminoalkoxy, hydroxy-substituted aminoalkoxy, haloalkoxy, amino-substituted haloalkoxy, alkylamino haloalkoxy, hydroxy-substituted haloalkoxy, alkylaminoalkoxy, alkoxyalkoxy, arylalkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, aryloxy, heterocyclyloxyalkoxy, carbocyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicycloxoalkoxy, fused heterobicycloxoalkoxy, fused bicyclyl aminoalkoxy, fused heterobicyclyl aminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)NR⁵—, fused heterobicyclyl-C(=O)NR⁵—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicycloxoalkoxy, spiro heterobicycloxoalkoxy, spiro bicyclylaminoalkoxy, spiro heterobicyclylaminoalkoxy, spiro bicyclyl—C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)NR⁵—, or spiro heterobicyclyl-C(=O)NR⁵—, aryl, heteroaryl, arylaliphatic and heteroarylaliphatic, haloaliphatic, hydroxyaliphatic, aminoaliphatic, alkoxyaliphatic, alkylaminoaliphatic, alkylthioaliphatic, aryloxyaliphatic, heterocyclyloxyaliphatic, cycloalkyloxyaliphatic, arylaminoaliphatic, heterocyclylaminoaliphatic, cycloalkylaminoaliphatic, arylaliphatic, heterocyclylaliphatic, cycloalkylaliphatic, heterocyclyl and carbocyclyl is independently substituted or unsubstituted.

2. The compound according to claim 1, wherein R³ is independently H, F, Cl, Br, —CN, C₁₋₃ aliphatic, C₁₋₃ alkoxy, or C₁₋₃ haloalkyl.

3. The compound according to claim 1, wherein $Q_i$ is

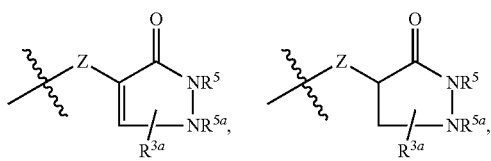

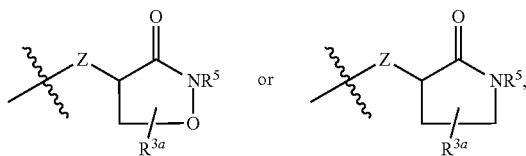

wherein R³ᵃ is H, F, Cl, Br, I, —CN, hydroxyl, R⁵ᵃR⁵N—, R⁵ᵃR⁵N-aliphatic, hydroxyaliphatic, aliphatic, alkoxy, alkoxyaliphatic, haloalkyl, heterocyclyl, heterocyclylalkyl, cycloalkyl, cycloalkoxy aliphatic, heterocycloxy aliphatic, cycloalkylalkoxy, heterocyclylalkoxy, aryloxyalkyl, heteroaryloxy aliphatic, arylaliphatic, heteroaryl aliphatic, aryl, or heteroaryl.

4. The compound according to claim 1, wherein $Q_2$ is

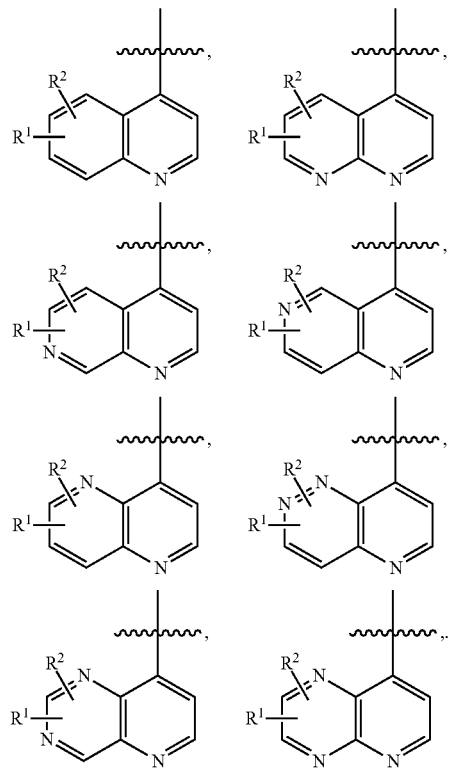

5. The compound according to claim 1, wherein $X_1$ is O or NR⁵.

6. The compound according to claim 1, wherein Z of formula (IIa) is —NHC(=O)—, and the substructure defined by $X_1$, $U_1$ and R³ of Formula I is:

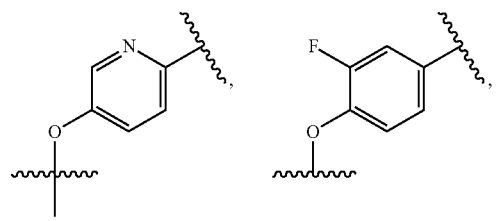

-continued

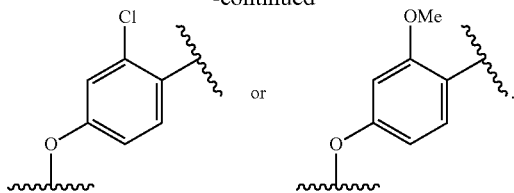

7. The compound according to claim 1, wherein:

$R^1$ is hydroxy-substituted cyclopropyl $C_{1-6}$alkoxy, $R^5S(=O)_2O$-substituted cyclopropyl $C_{1-6}$alkoxy, $C_{5-12}$ spiro bicyclyl, $C_{5-12}$ spiro heterobicyclyl, $C_{5-12}$ spiro bicyclyl $C_{1-6}$ aliphatic, $C_{5-12}$ spiro heterobicyclyl $C_{1-6}$ aliphatic, $C_{5-12}$ spiro heterobicycloxo $C_{1-6}$ alkoxy, $C_{5-12}$ spiro heterobicyclylamino $C_{1-6}$ alkoxy, $C_{5-12}$ spiro bicyclyl —C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)NR$^5$—, or $C_{5-12}$ spiro heterobicyclyl-C(=O)NR$^5$—; and $R^2$ is H, halo, cyano(CN), $R^{5a}R^5N$—$C_{1-6}$ alkoxy, optionally substituted $C_{1-6}$ alkoxy, $C_{1-6}$ hydroxyalkoxy, $C_{1-6}$ aminoalkoxy, $C_{1-6}$ hydroxy-substituted aminoalkoxy, $C_{1-6}$ haloalkoxy, $C_{1-6}$ alkylamino $C_{1-6}$ alkoxy, $C_{1-6}$ alkoxy $C_{1-6}$ alkoxy, $C_{4-10}$ heterocyclyloxy $C_{1-6}$ alkoxy, $C_{5-12}$ fused bicyclyl, $C_{5-12}$ fused bicyclyl $C_{1-6}$ aliphatic, $C_{5-12}$ fused heterobicyclyl $C_{1-6}$ aliphatic, $C_{5-12}$ fused bicycloxy, $C_{5-12}$ fused bicyclylamino, $C_{5-12}$ fused bicycloxo $C_{1-6}$ alkoxy, $C_{5-12}$ fused bicyclylamino $C_{1-6}$ alkoxy, $C_{5-12}$ fused bicyclyl-C(=O)—, $C_{5-12}$ fused bicyclyl-C(=O)O—, $C_{5-12}$ fused heterobicyclyl-C(=O)—, $C_{5-12}$ fused heterobicyclyl-C(=O)O—, $C_{5-12}$ fused bicyclylamino-C(=O)—, $C_{5-12}$ fused heterobicyclylamino-C(=O)—, $C_{5-12}$ fused bicyclyl-C(=O)NR$^5$—, $C_{5-12}$ fused heterobicyclyl-C(=O)NR$^5$—, $C_{5-12}$ spiro bicyclyl, $C_{5-12}$ spiro bicycloxy, $C_{5-12}$ spiro bicyclylamino, $C_{5-12}$ spiro bicycloxo $C_{1-6}$ alkoxy, $C_{5-12}$ spiro bicyclylamino $C_{1-6}$ alkoxy, $C_{5-12}$ fused heterobicyclyl, $C_{5-12}$ fused heterobicycloxy, $C_{5-12}$ fused heterobicyclylamino, $C_{5-12}$ fused heterobicycloxo $C_{1-6}$ alkoxy, $C_{5-12}$ fused heterobicyclylamino $C_{1-6}$ alkoxy, $C_{5-12}$ spiro bicyclyl, $C_{5-12}$ spiro heterobicyclyl, $C_{5-12}$ spiro bicyclyl $C_{1-6}$ aliphatic, $C_{5-12}$ spiro heterobicyclyl $C_{1-6}$ aliphatic, $C_{5-12}$ spiro heterobicycloxo $C_{1-6}$ alkoxy, $C_{5-12}$ spiro heterobicyclylamino $C_{1-6}$ alkoxy, $C_{5-12}$ spiro bicyclyl —C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)NR$^5$—, or $C_{5-12}$ spiro heterobicyclyl-C(=O)NR$^5$—, $C_{6-10}$ aryl, $C_{1-10}$ heteroaryl, $C_{6-10}$ aryl $C_{1-6}$ aliphatic or $C_{1-10}$ heteroaryl $C_{1-6}$ aliphatic.

8. The compound according to claim 1, wherein $R^1$ has one of the following structures:

(46)

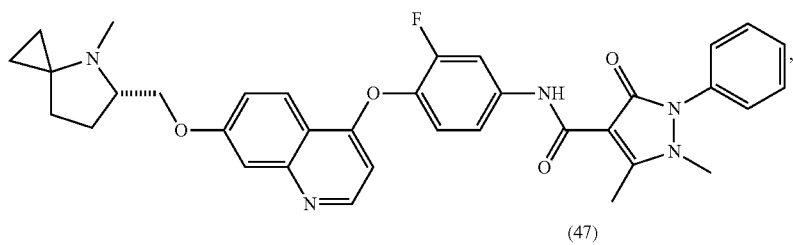

(47) (48)

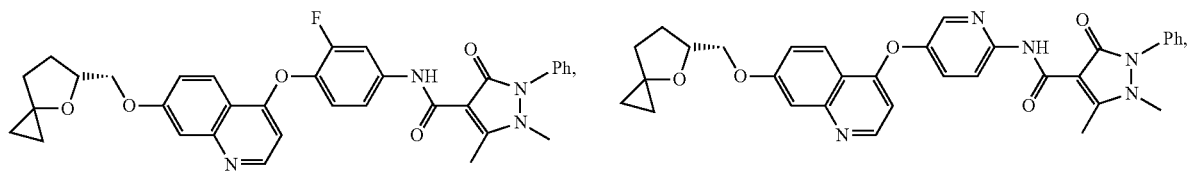

(49)

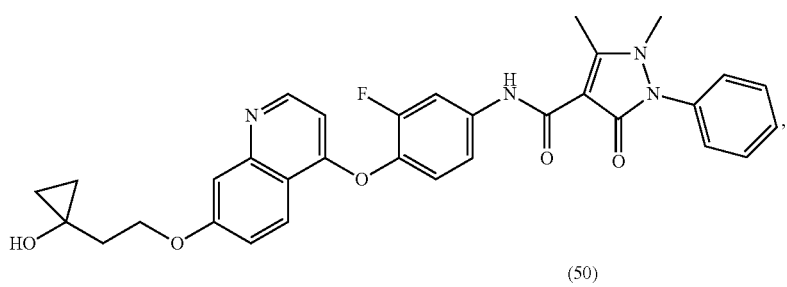

(50) (51)

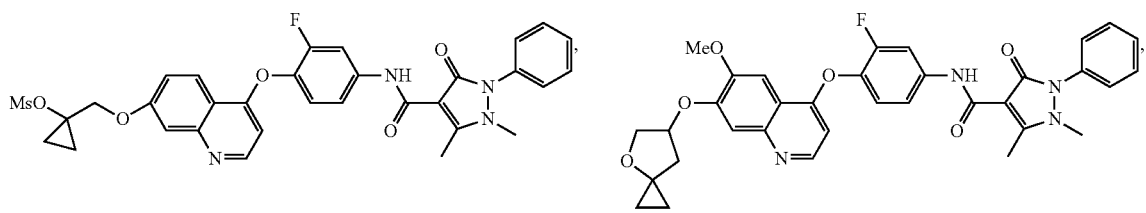

-continued
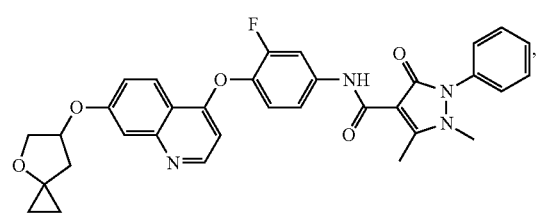
(52)
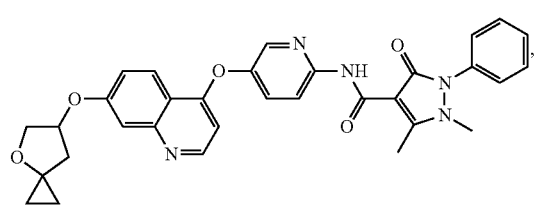
(53)
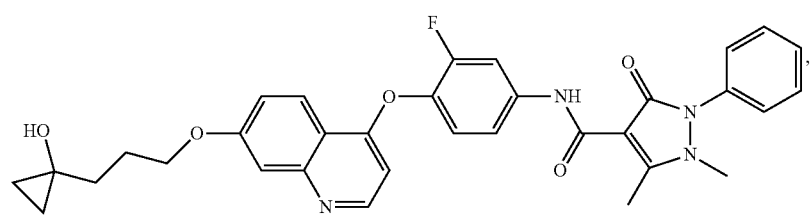
(54)
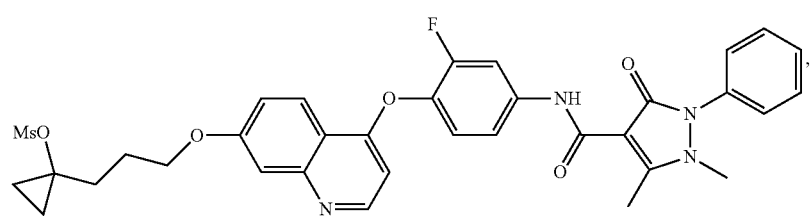
(55)
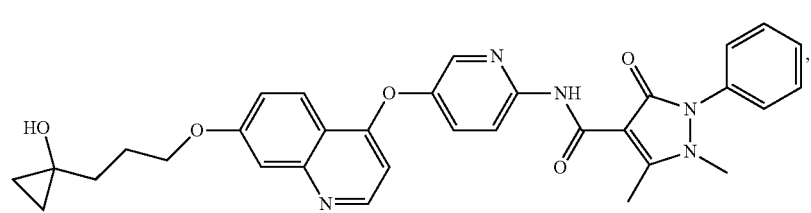
(56)
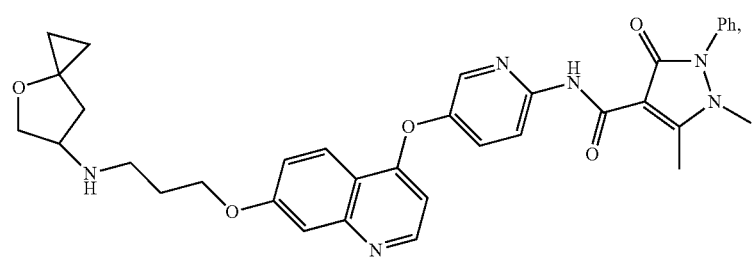
(57)
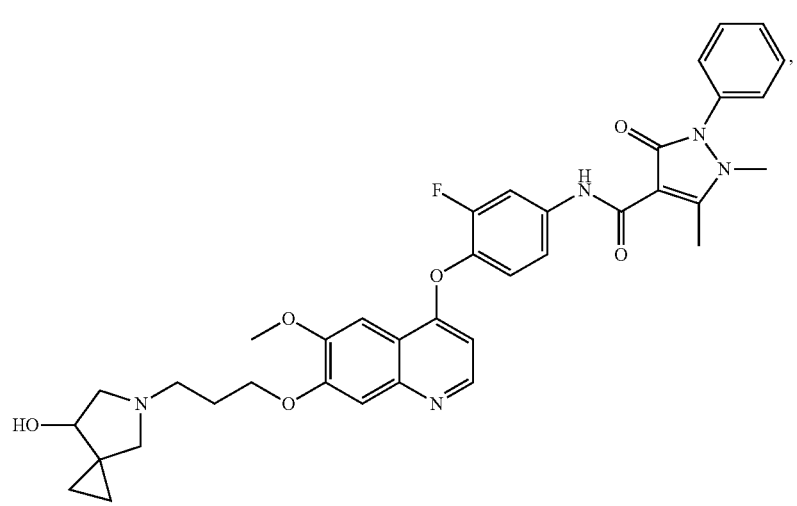
(58)

-continued
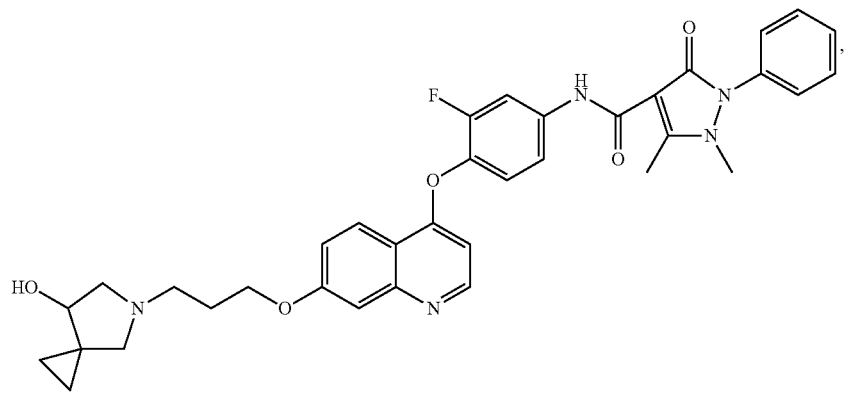
(59)
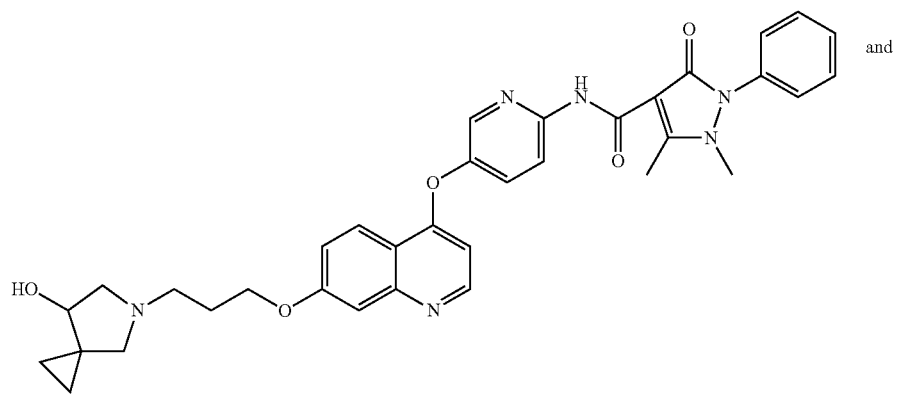
and
(60)
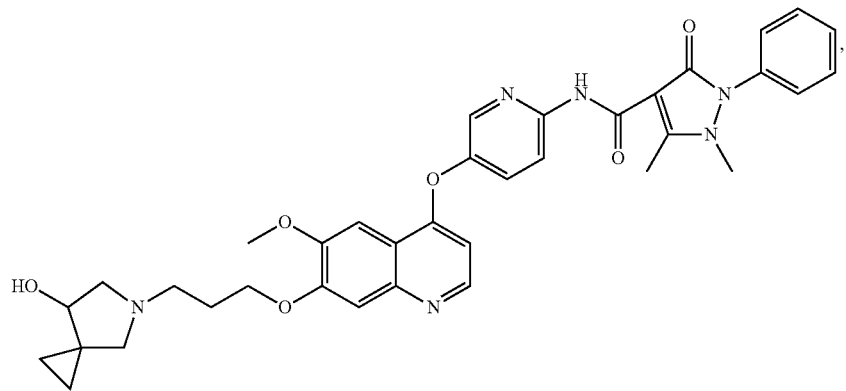
(61)
wherein each of $X_4$ and $X_4'$ is independently $(CR^4R^{4a})_m$, Me, O, S, S=O or $SO_2$; each of m and n is independently 0, 1 or 2; and t is 1, 2 or 3.
9. The compound of claim 1 having one of the following structures:
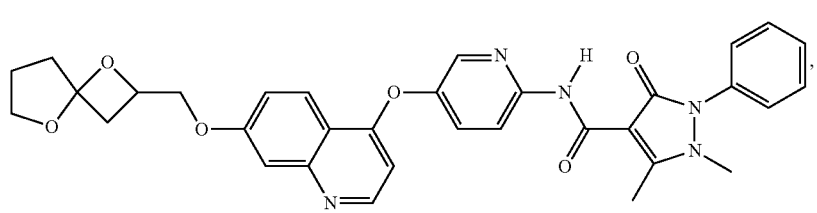
(1)

-continued
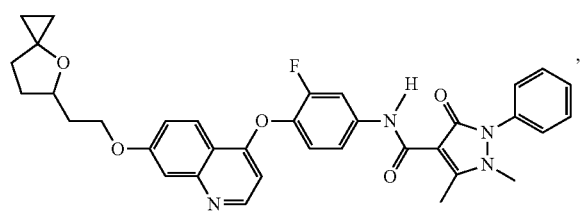 (2)
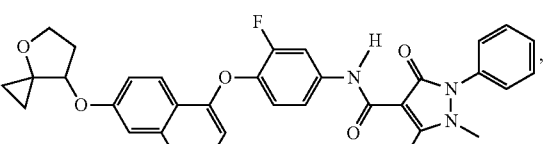 (3)
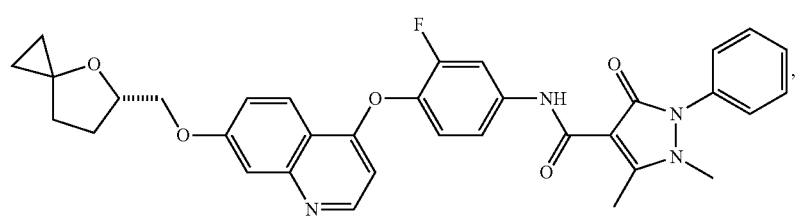 (4)
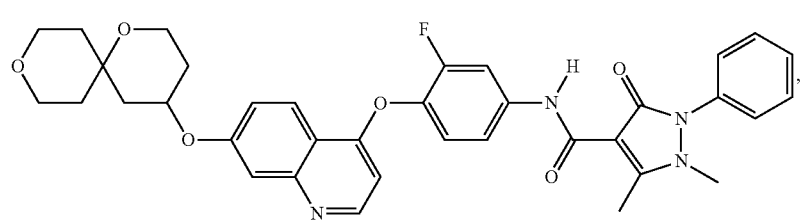 (6)
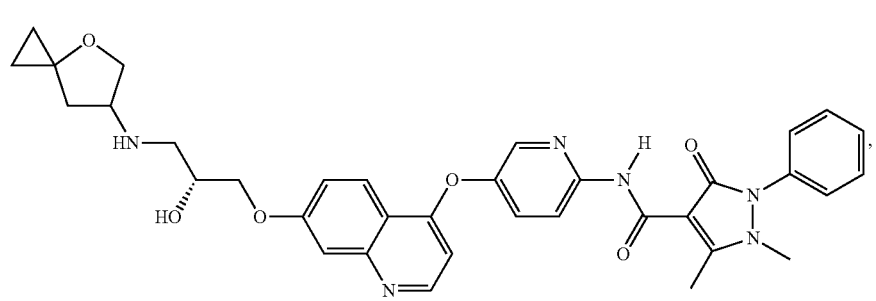 (7)
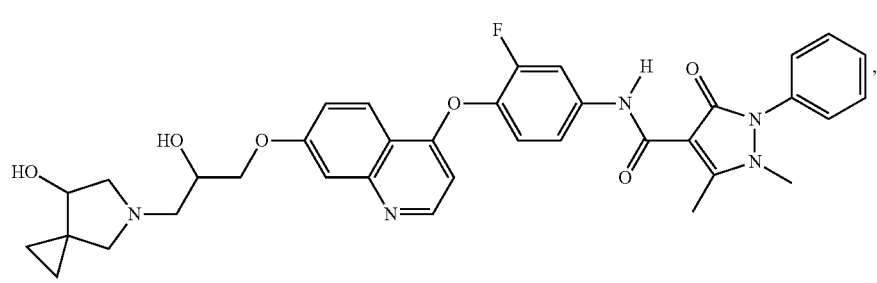 (29)
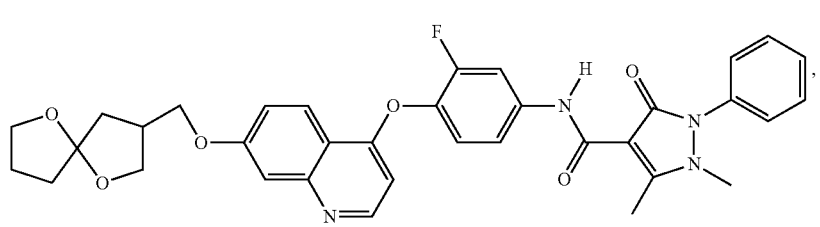 (31)
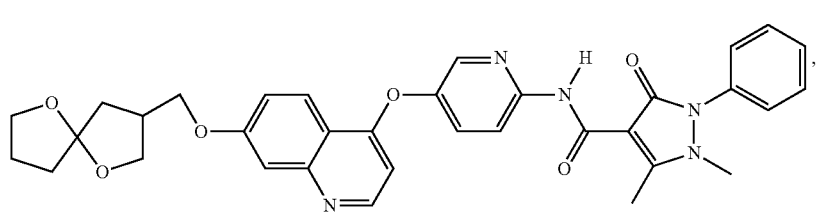 (32)

-continued
(36)
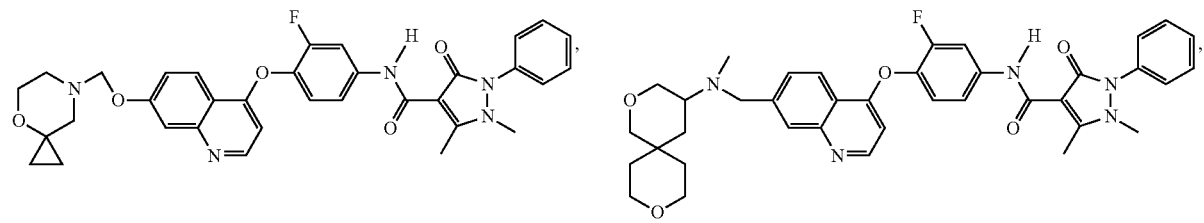
(39)
(44)
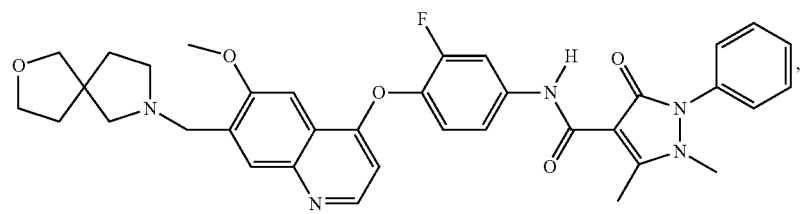
(45)
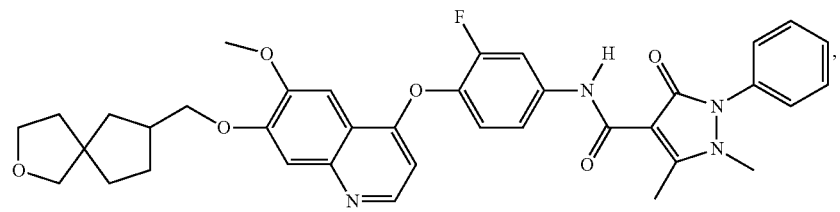
(46)
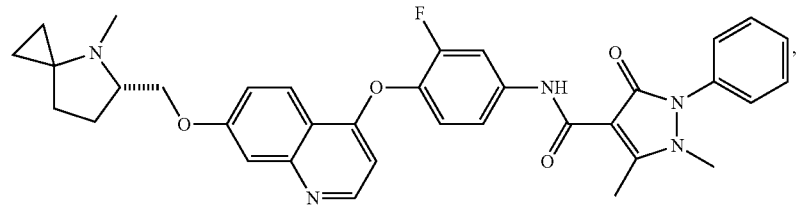
(47)
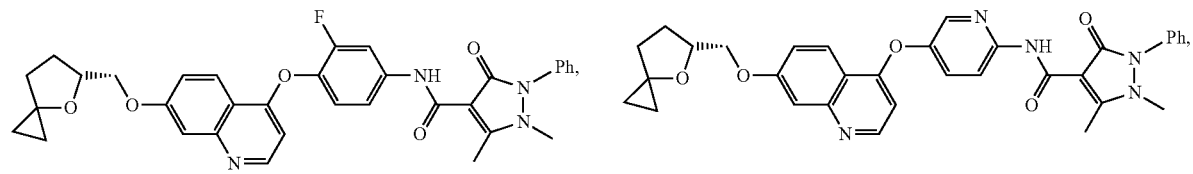
(48)
(49)
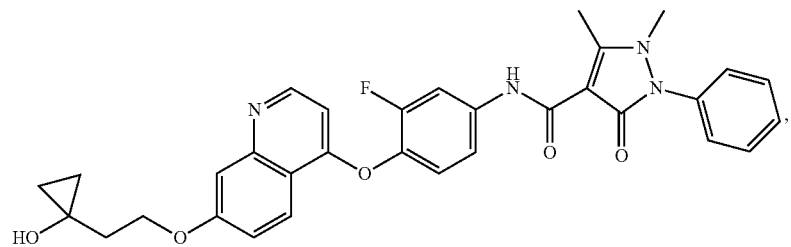
(50)
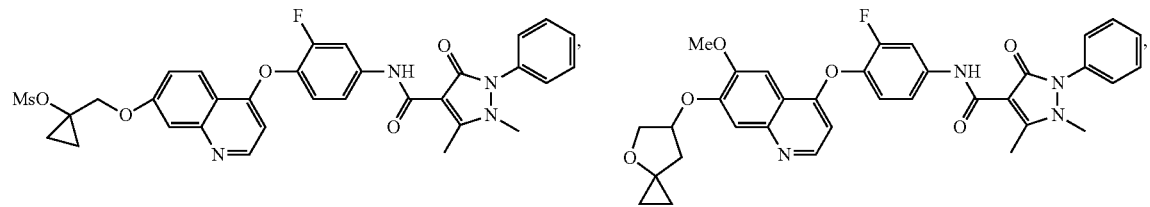
(51)

-continued
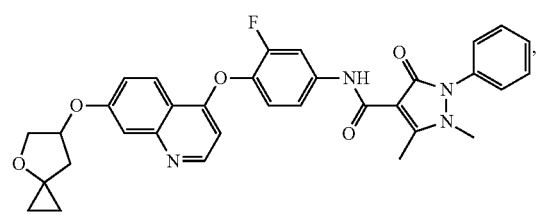
(52)
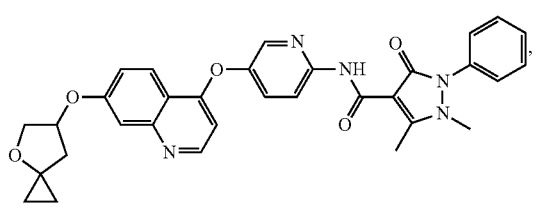
(53)
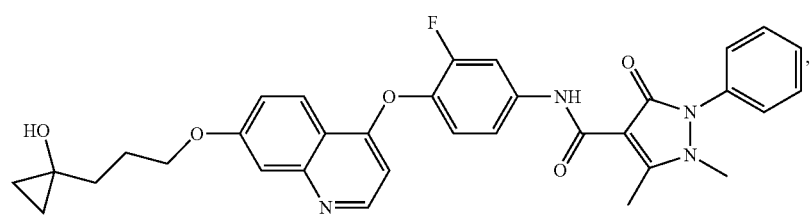
(54)
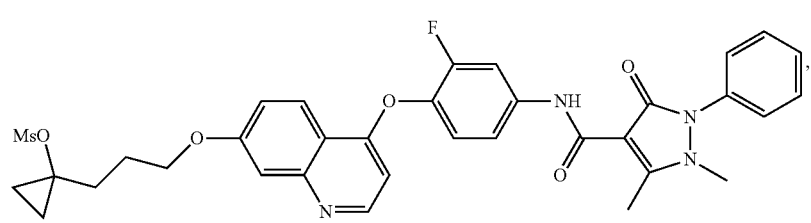
(55)
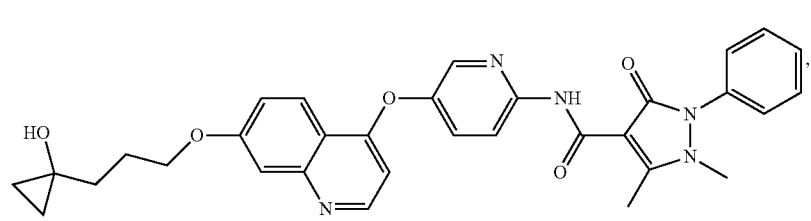
(56)
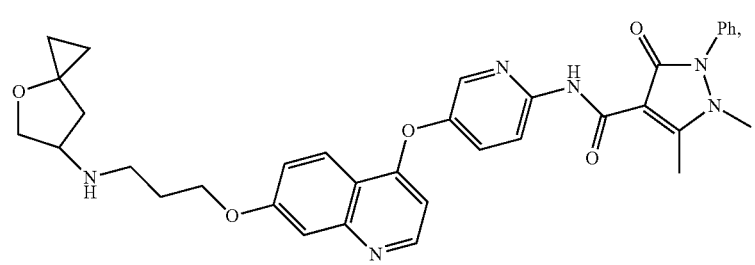
(57)
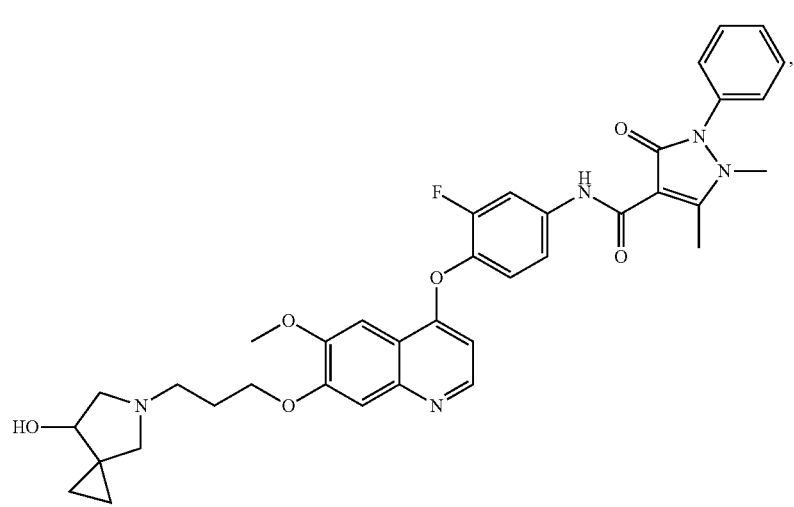
(58)

-continued
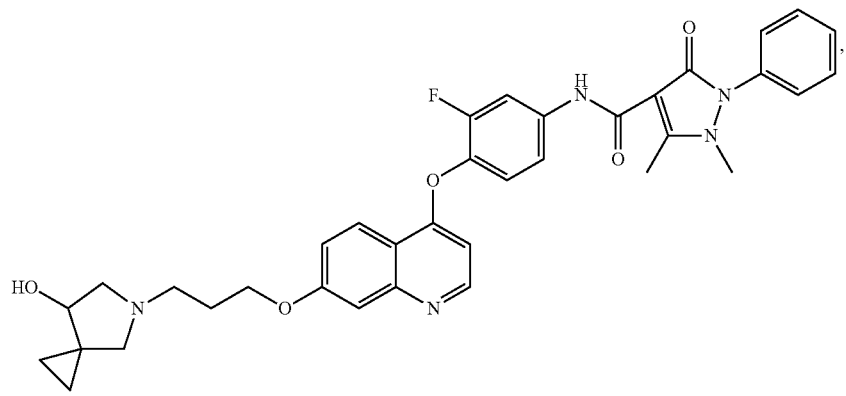
(59)
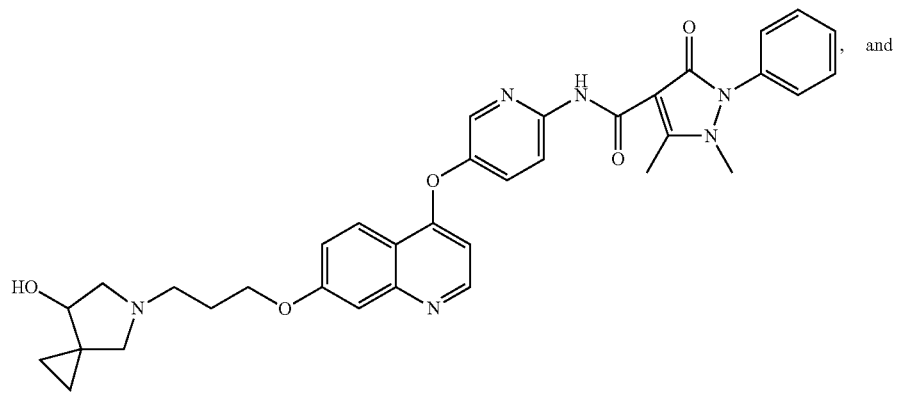
(60)
, and
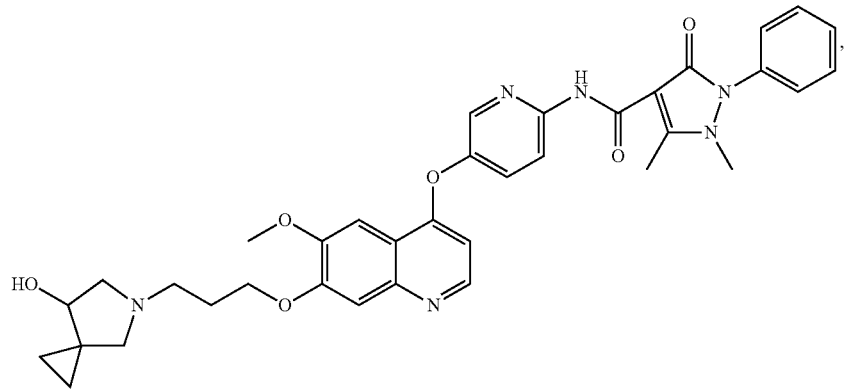
(61)
or a stereoisomer, a geometric isomer, a tautomer, an N-oxide, or a pharmaceutically acceptable salt thereof.
10. A compound of Formula (IV):
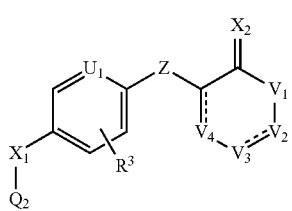
(IV)
or a stereoisomer, a geometric isomer, a tautomer, an N-oxide, or a pharmaceutically acceptable salt thereof, wherein:
$Q_2$ has formula (III):
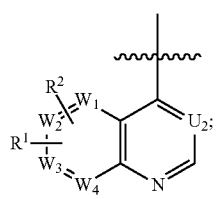
(III)

$R^1$ is one of the following structures:

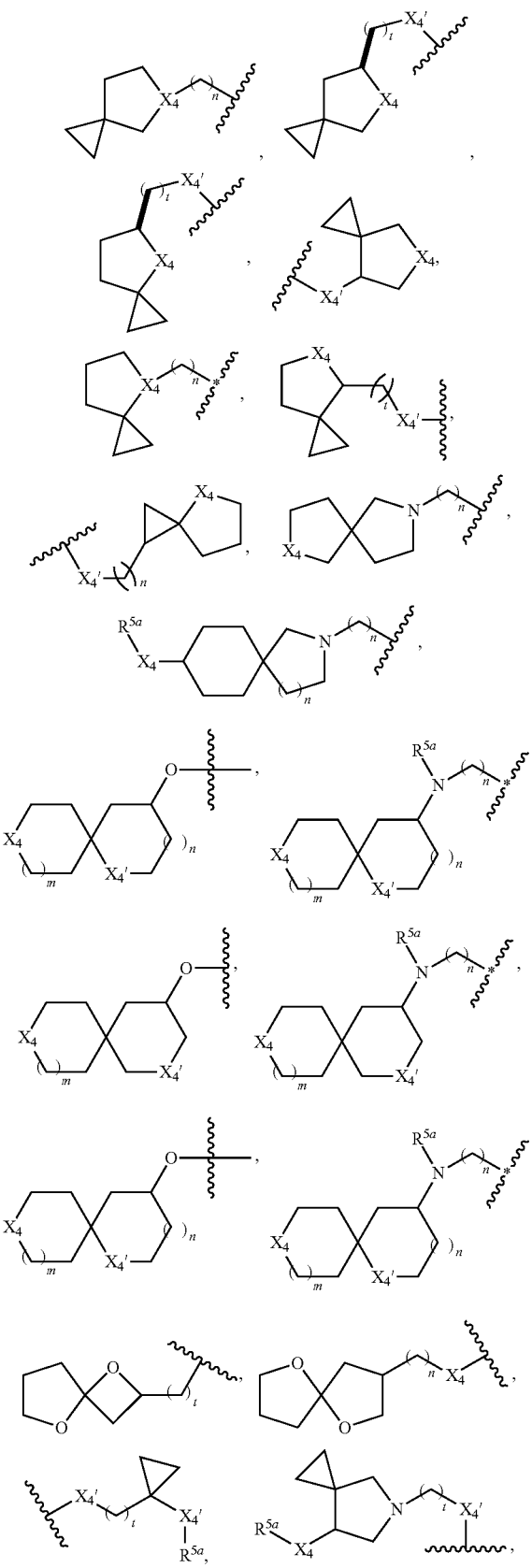
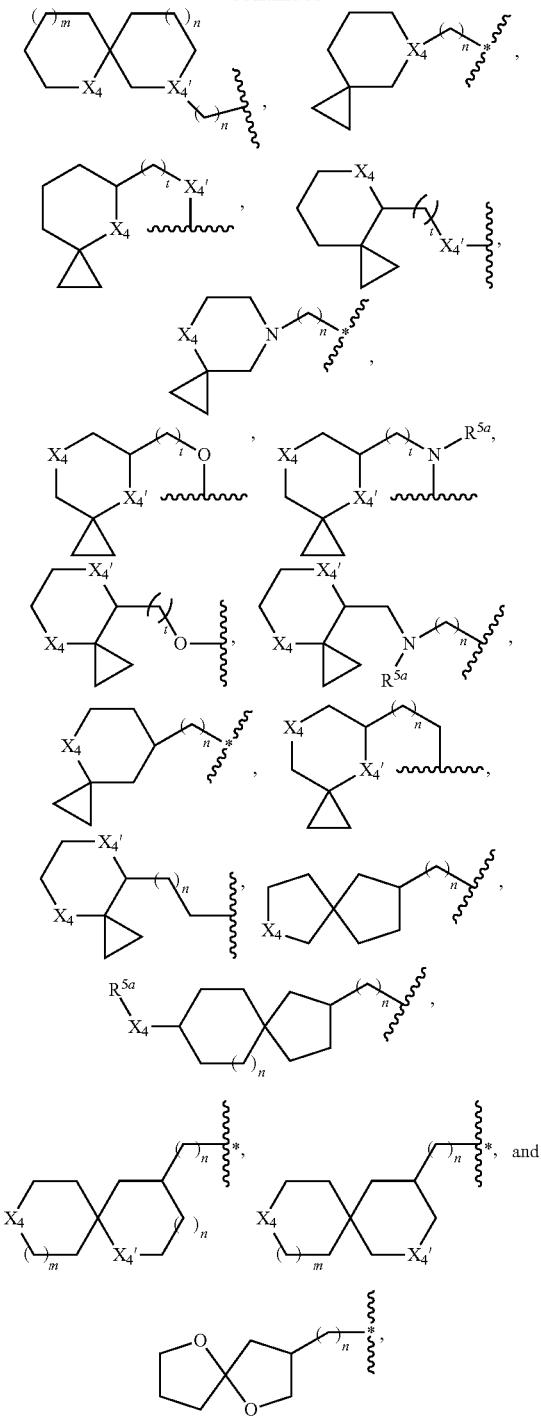

wherein each of $X_4$ and $X_4'$ is independently $(CR^4R^{4a})_m$, $NR^5$, O, S, S=O or $SO_2$; each of m and n is independently 0, 1 or 2; and t is 1, 2 or 3;

$R^2$ is H, halo, cyano, hydroxyl, $R^{5a}R^5N-$, $-C(=O)NR^5R^{5a}$, $-OC(=O)NR^5R^{5a}$, $-OC(=O)OR^5$, $-NR^5C(=O)NR^5R^{5a}$, $-NR^5C(=O)OR^{5a}$, $-NR^5C(=O)-R^{5a}$, $R^5R^{5a}N-O_2S-$, $R^5O_2S-$, $R^5O_2SR^{5a}N-$, $R^{5a}R^5N$-alkyl, $R^5S(=O)$-alkyl, $R^5R^{5a}N-C(=O)$-alkyl, $R^{5a}R^5N$-alkoxy, $R^5S(=O)$-alkoxy, $R^5R^{5a}N-C(=O)$-alkoxy, aliphatic, alkoxy, hydroxyalkoxy, aminoalkoxy, hydroxy-substituted aminoalkoxy, haloalkoxy, amino-substituted haloalkoxy, alkylamino haloalkoxy, hydroxy-substituted haloalkoxy, alkylaminoalkoxy, alkoxyalkoxy, arylalkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, aryloxy, heterocyclyloxyalkoxy, carbocyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicycloxoalkoxy, fused heterobicycloxoalkoxy, fused bicyclyl aminoalkoxy, fused heterobicyclyl aminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)NR$^5$—, fused heterobicyclyl-C(=O)NR$^5$—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicycloxoalkoxy, spiro heterobicycloxoalkoxy, spiro bicyclylaminoalkoxy, spiro heterobicyclylaminoalkoxy, spiro bicyclyl —C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)NR$^5$—, or spiro heterobicyclyl-C(=O)NR$^5$—, aryl, heteroaryl, arylaliphatic or heteroarylaliphatic, with the proviso that when alkoxy or alkylamino is substituted, each of alkoxy or alkylamino is independently substituted with one or more hydroxy groups, amino groups or substituted amino groups;

$R^3$ is H, F, Cl, Br, I, —CN, hydroxyl, $R^{5a}R^5N$—, aliphatic, alkoxy, haloalkyl, heterocyclyl, heterocyclylalkyl, cycloalkyl, cycloalkyl aliphatic, cycloalkylalkoxy, or heterocyclylalkoxy;

each of $U_1$ and $U_2$ is independently $CR^4$ or N;

$V_1$ is O or $NR^5$;

$V_2$ is $CR^4R^{4a}$, $NR^5$, $CR^4$ or N, and $V_3$ and $V_4$ combine to become $CR^4R^{4a}$, $NR^5$, O, $CR^4$ or N;

each of $W_1$, $W_2$, $W_3$ and $W_4$ is independently $CR^4R^{4a}$, $NR^5$, $CR^4$ or N;

$X_1$ is $(CR^4R^{4a})_m$, $NR^5$, O, S, S=O or $SO_2$, where m is 0, 1 or 2;

$X_2$ is independently O, S or $NR^5$;

Z is —$NR^5C(=O)$—$(CR^4R^{4a})_p$—, —$NR^5C(=S)$—$(CR^4R^{4a})_p$—, —$NR^{5a}$—$(CR^4R^{4a})_p$—, —$NR^5$—$(CR^4R^{4a})_p C(=O)$—, —$NR^5$—$(CR^4R^{4a})_p C(=S)$—, —$NR^5 S(=O)_r$—, —$NR^5 S(=O)_r (CR^4R^{4a})_p$—, —$C(=O)NR^5 (CR^4R^{4a})_p$— or —$NR^5 (CR^4R^{4a})_p S(=O)_r$—, where p is 0, 1, 2 or 3; and r is 1 or 2;

each of $R^4$ and $R^{4a}$ is independently H, F, Cl, Br, I, —CN, hydroxyl, —$NR^{5a}R^5$, alkoxy, cycloalkoxy, heterocycloalkoxy, aliphatic, haloaliphatic, hydroxyaliphatic, aminoaliphatic, alkoxyaliphatic, alkylaminoaliphatic, alkylthioaliphatic, aryloxyaliphatic, heterocyclyloxyaliphatic, cycloalkyloxyaliphatic, arylaminoaliphatic, heterocyclylaminoaliphatic, cycloalkylaminoaliphatic, arylaliphatic, heterocyclylaliphatic, cycloalkylaliphatic, aryl, heteroaryl, heterocyclyl or carbocyclyl, with the proviso that where $R^4$ and $R^{4a}$ are bonded to the same carbon atom, $R^4$ and $R^{4a}$, together with the carbon atom they are attached to, optionally form a substituted or unsubstituted 3-8 membered carbocyclic or heterocyclic ring;

each of $R^5$ and $R^{5a}$ is independently H, $R^6R^{6a}NC(=O)$—, $R^6OC(=O)$—, $R^6C(=O)$—, $R^6R^{6a}NS(=O)$—, $R^6OS(=O)$—, $R^6S(=O)$—, $R^6R^{6a}NSO_2$—, $R^6OSO_2$—, $R^6SO_2$—, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl, with the proviso that where $R^5$ and $R^{5a}$ are bonded to the same nitrogen atom, $R^5$ and $R^{5a}$, together with the nitrogen atom they are attached to, optionally form a substituted or unsubstituted 3-8 membered ring, including spiro and fused bicyclic rings;

each of $R^6$ and $R^{6a}$ is independently H, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl, or carbocyclyl;

wherein each of $R^{5a}R^5N$—, —$C(=O)NR^5R^{5a}$, —$OC(=O)NR^5R^{5a}$, —$OC(=O)OR^5$, —$NR^5C(=O)NR^5R^{5a}$, —$NR^5C(=O)OR^{5a}$, —$NR^5C(=O)$—$R^{5a}$, $R^5R^{5a}N$-$O_2S$—, $R^5O_2S$—, $R^5O_2SR^{5a}N$—, $OR^5$, $NR^5$, $CR^4R^{4a}$, $CR^4$, $(CR^4R^{4a})_m$, —$NR^5C(=O)$—$(CR^4R^{4a})_p$—, —$NR^5C(=S)$—$(CR^4R^{4a})_p$—, —$NR^{5a}$-$(CR^4R^{4a})_p$—, —$NR^5$—$(CR^4R^{4a})_p C(=O)$—, —$NR^5$—$(CR^4R^{4a})_p C(=S)$—, —$NR^5 S(=O)_r$—, —$NR^5 S(=O)_r (CR^4R^{4a})_p$—, —$C(=O)NR^5$—$(CR^4R^{4a})_p$—, —$NR^5$—$(CR^4R^{4a})_p$—$S(=O)_r$—, $R^{5a}R^5N$-alkyl, $R^5(S=O)$-alkyl, $R^5R^{5a}N$—$(C=O)$-alkyl, $R^{5a}R^5N$-alkoxy, $R^5(S=O)$-alkoxy, $R^5R^{5a}N$—$(C=O)$-alkoxy, $R^6R^{6a}NC(=O)$—, $R^6OC(=O)$—, $R^6C(=O)$—, $R^6R^{6a}NS(=O)$—, $R^6OS(=O)$—, $R^6S(=O)$—, $R^6R^{6a}NSO_2$—, $R^6OSO_2$—, $R^6SO_2$—, hydroxy-substituted cyclopropylalkoxy, $R^5S(=O)_2O$-substituted cyclopropylalkoxy, aliphatic, alkoxy, hydroxyalkoxy, aminoalkoxy, hydroxy-substituted aminoalkoxy, haloalkoxy, amino-substituted haloalkoxy, alkylamino haloalkoxy, hydroxy-substituted haloalkoxy, alkylaminoalkoxy, alkoxyalkoxy, arylalkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, aryloxy, heterocyclyloxyalkoxy, carbocyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicycloxoalkoxy, fused heterobicycloxoalkoxy, fused bicyclyl aminoalkoxy, fused heterobicyclyl aminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)NR$^5$—, fused heterobicyclyl-C(=O)NR$^5$—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicycloxoalkoxy, spiro heterobicycloxoalkoxy, spiro bicyclylaminoalkoxy, spiro heterobicyclylaminoalkoxy, spiro bicyclyl —C(=O)—, spiro bicyclyl-C(=O)O—, spiro heterobicyclyl-C(=O)—, spiro heterobicyclyl-C(=O)O—, spiro bicyclylamino-C(=O)—, spiro heterobicycly lamino-C(=O)—, spiro bicyclyl-C(=O)NR⁵—, or spiro heterobicyclyl-C(=O)NR⁵—, aryl, heteroaryl, arylaliphatic and heteroarylaliphatic, haloaliphatic, hydroxyaliphatic, aminoaliphatic, alkoxyaliphatic, alkylaminoaliphatic, alkylthioaliphatic, aryloxyaliphatic, heterocyclyloxyaliphatic, cycloalkyloxyaliphatic, arylaminoaliphatic, heterocyclylaminoaliphatic, cycloalkylaminoaliphatic, arylaliphatic, heterocyclylaliphatic, cycloalkylaliphatic, heterocyclyl and carbocyclyl is independently substituted or unsubstituted.

11. The compound according to claim 10, wherein $R^3$ is independently H, F, Cl, Br, —CN, $C_{1-3}$ aliphatic, $C_{1-3}$ alkoxy, or $C_{1-3}$ haloalkyl.

12. The compound according to claim 10, wherein the substructure defined by $X_2, V_1, V_2, V_3, V_4$ and Z of Formula (IV) is

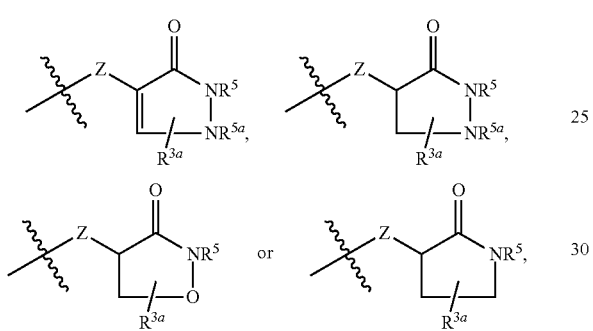

wherein $R^{3a}$ is H, F, Cl, Br, I, —CN, hydroxyl, $R^{5a}R^5N$—, $R^{5a}R^5N$-aliphatic, hydroxyaliphatic, aliphatic, alkoxy, alkoxyaliphatic, haloalkyl, heterocyclyl, heterocyclylalkyl, cycloalkyl, cycloalkoxy aliphatic, heterocycloxy aliphatic, cycloalkylalkoxy, heterocyclylalkoxy, aryloxyalkyl, heteroaryloxy aliphatic, arylaliphatic, heteroaryl aliphatic, aryl, or heteroaryl.

13. The compound according to claim 10 wherein $Q_2$ is

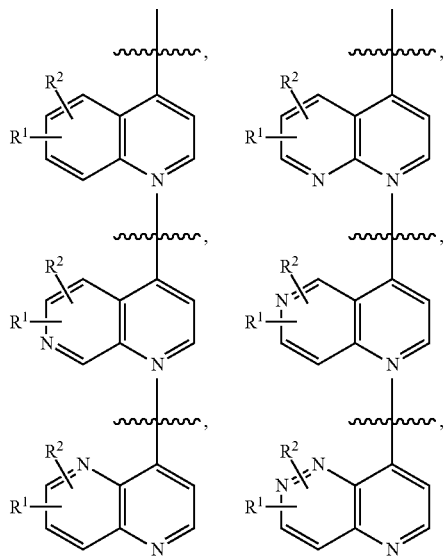

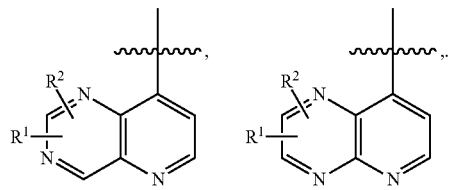

14. The compound according to claim 10, wherein $X_1$ is O or $NR^5$.

15. The compound according to claim 10, wherein Z is —NHC(=O)—.

16. The compound according to claim 10, wherein the substructure defined by $X_1, Z, U_1$ and $R^3$ is

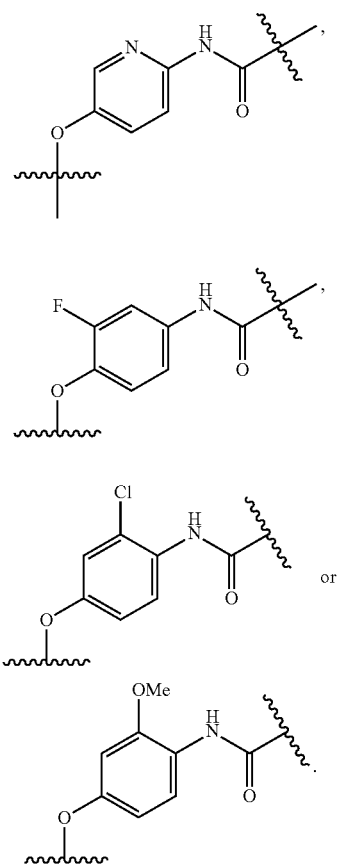

17. The compound according to claim 1, wherein the substructure defined by $X_1, Z, U_1$ and $R^3$ of Formula (IV) is:

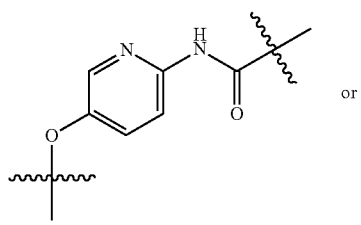

-continued

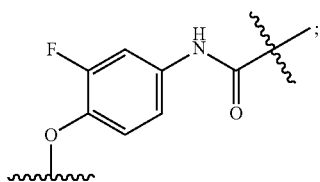

the substructure defined by $X_2$, $V_1$, $V_2$, $V_3$, $V_4$ and Z of Formula (IV) is:

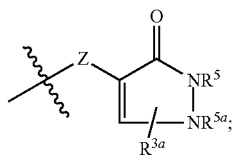

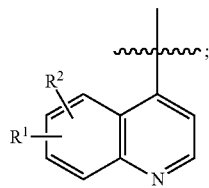

$Q_2$ is

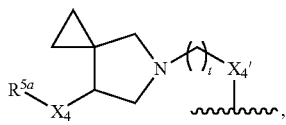

$R^1$ is
wherein each of $X_4$ and $X_4{'}$ is independently O, and t is 3;
$R^2$ is H;
$R^{3a}$ is aliphatic; and
each of $R^5$ and $R^{5a}$ is independently H, aliphatic or aryl.

18. The compound of claim 10 having one of the following structures:
or a stereoisomer, a geometric isomer, a tautomer, an N-oxide, or a pharmaceutically acceptable salt thereof.

19. A pharmaceutical composition comprising a compound according to claim 1 and a pharmaceutically acceptable carrier, excipient, diluent, adjuvant, vehicle or a combination thereof.

20. The composition according to claim 19 further comprising a therapeutic agent selected from a chemotherapeutic agent, an anti-proliferative agent, an agent for treating atherosclerosis, an agent for treating lung fibrosis, and combinations thereof.

21. The composition according to claim 20, wherein the additional therapeutic agent is adriamycin, rapamycin, temsirolimus, everolimus, ixabepilone, gemcitabin, cyclophosphamide, dexamethasone, etoposide, fluorouracil, imatinib mesylate, dasatinib, nilotinib, erlotinib, lapatinib, iressa, sorafenib, sunitinib, an interferon, carboplatin, topotecan, taxol, vinblastine, vincristine, temozolomide, tositumomab, trabecdectin, bevacizumab, panitumumab, or a combination thereof.

\* \* \* \* \*